US012774267B2

(12) United States Patent
Crean et al.

(10) Patent No.: US 12,774,267 B2
(45) Date of Patent: Oct. 27, 2026

(54) PRODRUGS OF Kv7 CHANNEL OPENERS

(71) Applicant: Chatham Biopharma Consulting, LLC, Pittsboro, NC (US)

(72) Inventors: Christopher S. Crean, Pittsboro, NC (US); Edward G. Brown, Cary, NC (US)

(73) Assignee: Xyzagen, Inc., Pittsboro, NC (US)

( * ) Notice: Subject to any disclaimer, the term of this patent is extended or adjusted under 35 U.S.C. 154(b) by 314 days.

(21) Appl. No.: 18/282,943

(22) PCT Filed: Mar. 20, 2022

(86) PCT No.: PCT/US2022/021059

§ 371 (c)(1),
(2) Date: Sep. 19, 2023

(87) PCT Pub. No.: WO2022/198116

PCT Pub. Date: Sep. 22, 2022

(65) Prior Publication Data

US 2024/0208896 A1 Jun. 27, 2024

Related U.S. Application Data

(60) Provisional application No. 63/163,470, filed on Mar. 19, 2021.

(51) Int. Cl.

| | |
|---|---|
| ***C07C 271/28*** | (2006.01) |
| ***A61K 31/216*** | (2006.01) |
| ***A61K 31/27*** | (2006.01) |
| ***A61K 31/44*** | (2006.01) |
| ***C07D 213/28*** | (2006.01) |
| ***C07D 213/74*** | (2006.01) |
| ***C07D 213/75*** | (2006.01) |

(52) U.S. Cl.

CPC .......... *C07C 271/28* (2013.01); *A61K 31/216* (2013.01); *A61K 31/27* (2013.01); *A61K 31/44* (2013.01); *C07D 213/28* (2013.01); *C07D 213/74* (2013.01); *C07D 213/75* (2013.01)

(58) Field of Classification Search

CPC .. C07C 271/28; C07D 213/28; C07D 213/74; C07D 213/75; A61K 31/216; A61K 31/27; A61K 31/44

USPC .......................................................... 514/352

See application file for complete search history.

(56) References Cited

U.S. PATENT DOCUMENTS

| | | | |
|---|---|---|---|
| 5,384,330 | A | 1/1995 | Dieter et al. |
| 7,109,239 | B2 | 9/2006 | Gallop et al. |
| 2006/0004197 | A1 | 1/2006 | Thrash et al. |
| 2014/0336252 | A1 | 11/2014 | Nan et al. |

FOREIGN PATENT DOCUMENTS

| | | | |
|---|---|---|---|
| CN | 102159535 | A | 8/2011 |
| CN | 103073455 | A | 5/2013 |
| CN | 109641836 | A | 4/2019 |
| EP | 2772481 | A1 | 9/2014 |
| EP | 2310357 | B1 | 9/2019 |
| JP | 2004115450 | A | 4/2004 |
| WO | 2006014405 | A2 | 2/2006 |
| WO | 2013179298 | A2 | 12/2013 |
| WO | 2016077724 | A1 | 5/2016 |
| WO | 2017214539 | A1 | 12/2017 |
| WO | 2020047603 | A1 | 3/2020 |

OTHER PUBLICATIONS

Search Report for Chinese Application No. 202280034756.0, dated Jul. 15, 2025.

Aiba, Isamu, and Jeffrey L. Noebels. "Kcnq2/Kv7. 2 controls the threshold and bi-hemispheric symmetry of cortical spreading depolarization." Brain 144.9 (2021): 2863-2878.

Baculis, Brian C. et al. "The role of Kv7 channels in neural plasticity and behavior." Frontiers in physiology 11 (2020): 568667.

Blom, Sigrid Marie, et al. "From pan-reactive KV7 channel opener to subtype selective opener/inhibitor by addition of a methyl group." PloS one 9.6 (2014): e100209.

Brant, Steven R., et al. "Genome-wide association study identifies African-specific susceptibility loci in African Americans with inflammatory bowel disease." Gastroenterology 152.1 (2017): 206-217.

Brown, David A., and Gayle M. Passmore. "Neural KCNQ (kv7) channels." British journal of pharmacology 156.8 (2009): 1185-1195.

(Continued)

*Primary Examiner* — Kahsay Habte

(74) *Attorney, Agent, or Firm* — Barnes & Thornburg LLP

(57) ABSTRACT

Prodrugs of pharmacologically active 1,2,4-triaminobenzene derivatives of the General Formula (I); or pharmaceutically acceptable salts thereof, where the symbols $R^1$, $R^2$, $R^3$, $R^4$, $R^5$ and $R^{6a}$, $R^{6b}$, and $R^{6c}$ and where the symbol Z are defined. Methods for the synthesis, purification, testing and use as prodrugs of pharmacologically-active agents at Kv7 ion channels are provided.

(I)

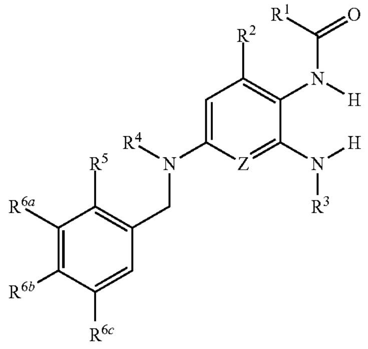

20 Claims, 24 Drawing Sheets

(56) References Cited

OTHER PUBLICATIONS

Chen, Tao, et al. "Brain-derived neurotrophic factor increases synaptic protein levels via the MAPK/Erk signaling pathway and Nrf2/Trx axis following the transplantation of neural stem cells in a rat model of traumatic brain injury." Neurochemical Research 42 (2017): 3073-3083.
Czuczwar, Piotr, et al. "Retigabine: the newer potential antiepileptic drug." Pharmacological Reports 62.2 (2010): 211-219.
De Jong, Inge EM, and Thomas A. Jepps. "Impaired Kv7 channel function in cerebral arteries of a tauopathy mouse model (rT g4510)." Physiological Reports 6.23 (2018): e13920.
Feng, Mengyang, et al. "Reversal of a treatment-resistant, depression-related brain state with the Kv7 channel opener retigabine." Neuroscience 406 (2019): 109-125.
Fosmo, Andreas L., and Øyvind B. Skraastad. "The Kv7 channel and cardiovascular risk factors." Frontiers in cardiovascular medicine 4 (2017): 75.
Garakani, Amir, et al. "Pharmacotherapy of anxiety disorders: current and emerging treatment options." Focus 19.2 (2021): 222-242.
Gilling, Mette, et al. "Dysfunction of the heteromeric KV7. 3/KV7. 5 potassium channel is associated with autism spectrum disorders." Frontiers in genetics 4 (2013): 54.
Greene, Derek L., Anastasia Kosenko, and Naoto Hoshi. "Attenuating M-current suppression in vivo by a mutant Kcnq2 gene knock-in reduces seizure burden and prevents status epilepticus-induced neuronal death and epileptogenesis." Epilepsia 59.10 (2018): 1908-1918.
Guglielmi, Luca, et al. "Update on the implication of potassium channels in autism: K+ channelautism spectrum disorder." Frontiers in cellular neuroscience 9 (2015): 34.
Gunthorpe, Martin J., Charles H. Large, and Raman Sankar. "The mechanism of action of retigabine (ezogabine), a first-in-class K+ channel opener for the treatment of epilepsy." Epilepsia 53.3 (2012): 412-424.
International Preliminary Report on Patentability issued in PCT/US2022/021058, mailed Sep. 12, 2023.
International Search Report issued in PCT/US2022/021058, mailed Jul. 1, 2022.
Kalappa, Bopanna I., et al. "Potent KCNQ2/3-specific channel activator suppresses in vivo epileptic activity and prevents the development of tinnitus." Journal of Neuroscience 35.23 (2015): 8829-8842.
Kasteleijn-Nolst Trenité, Dorotheé GA, et al. "K v7 potassium channel activation with ICA-105665 reduces photoparoxysmal EEG responses in patients with epilepsy." Epilepsia 54.8 (2013): 1437-1443.
Kim, Eung Chang, et al. "Heterozygous loss of epilepsy gene KCNQ2 alters social, repetitive and exploratory behaviors." Genes, Brain and Behavior 19.1 (2020): e12599.
Larsson, Johan E., Damon JA Frampton, and Sara I. Liin. "Polyunsaturated fatty acids as modulators of KV7 channels." Frontiers in physiology 11 (2020): 641.
Lee, Sewon, et al. "Heterogeneity in Kv7 channel function in the cerebral and coronary circulation." Microcirculation 22.2 (2015): 109-121.
Li, Lin, et al. "Activation of KCNQ channels prevents paclitaxel-induced peripheral neuropathy and associated neuropathic pain." The Journal of Pain 20.5 (2019): 528-539.
Linley, John E., et al. "Inhibition of M current in sensory neurons by exogenous proteases: a signaling pathway mediating inflammatory nociception." Journal of Neuroscience 28.44 (2008): 11240-11249.
Maghera, Jasmine, et al. "Familial neonatal seizures caused by the Kv7. 3 selectivity filter mutation T313I." Epilepsia Open 5.4 (2020): 562-573.
Maljevic, Snezana, Thomas V. Wuttke, and Holger Lerche. "Nervous system KV7 disorders: breakdown of a subthreshold brake." The Journal of physiology 586.7 (2008): 1791-1801.
Milh, Mathieu, et al. "A knock-in mouse model for KCNQ2-related epileptic encephalopathy displays spontaneous generalized seizures and cognitive impairment." Epilepsia 61.5 (2020): 868-878.
Milh, Mathieu, et al. "Similar early characteristics but variable neurological outcome of patients with a de novo mutation of KCNQ2." Orphanet journal of rare diseases 8 (2013): 1-8.
Misra, Ravi, and Naila Arebi. "Re: Genome-wide association study identifies African-specific susceptibility loci in African Americans with inflammatory bowel disease." Gastroenterology 152.8 (2017): 2082-2083.
Mondejar-Parreño, Gema, Francisco Perez-Vizcaino, and Angel Cogolludo. "Kv7 channels in lung diseases." Frontiers in Physiology 11 (2020): 634.
Peters, H. Christian, et al. "Conditional transgenic suppression of M channels in mouse brain reveals functions in neuronal excitability, resonance and behavior." Nature neuroscience 8.1 (2005): 51-60.
Ramírez-Barrantes, R., et al. "Perspectives of TRPV1 function on the neurogenesis and neural plasticity." Neural plasticity 2016 (2016).
Ray, Sutirtha, et al. "The paracetamol metabolite N-acetylp-benzoquinone imine reduces excitability in first- and second-order neurons of the pain pathway through actions on KV7 channels." Pain 160.4 (2019): 954.
Redford, Kaitlyn E., et al. "KCNQ5 potassium channel activation underlies vasodilation by tea." Cellular physiology and biochemistry: international journal of experimental cellular physiology, biochemistry, and pharmacology 55.Suppl 3 (2021): 46.
Richter, A., S. E. Sander, and C. Rundfeldt. "Antidystonic effects of Kv7 (KCNQ) channel openers in the dtsz mutant, an animal model of primary paroxysmal dystonia." British journal of pharmacology 149.6 (2006): 747-753.
Soh, Heun, et al. "Conditional deletions of epilepsy-associated KCNQ2 and KCNQ3 channels from cerebral cortex cause differential effects on neuronal excitability." Journal of Neuroscience 34.15 (2014): 5311-5321.
Sotty, Florence, et al. "Antipsychotic-like effect of retigabine [N-(2-Amino-4-(fluorobenzylamino)-phenyl) carbamic acid ester], a KCNQ potassium channel opener, via modulation of mesolimbic dopaminergic neurotransmission." Journal of Pharmacology and Experimental Therapeutics 328.3 (2009): 951-962.
Sun, Bo, et al. "Reciprocal regulation of Th2 and Th17 cells by PAD2-mediated citrullination." JCI insight 4.22 (2019).
Teng, Bo-chuan, et al. "Activation of neuronal Kv7/KCNQ/M-channels by the opener QO58-lysine and its anti-nociceptive effects on inflammatory pain in rodents." Acta Pharmacologica Sinica 37.8 (2016): 1054-1062.
Vanhoof-Villalba, Stephanie L., et al. "Pharmacogenetics of KCNQ channel activation in 2 potassium channelopathy mouse models of epilepsy." Epilepsia 59.2 (2018): 358-368.
Vigil, Fabio A., Chase M. Carver, and Mark S. Shapiro. "Pharmacological manipulation of K v 7 channels as a new therapeutic tool for multiple brain disorders." Frontiers in Physiology 11 (2020): 688.
Wainger, Brian J., et al. "Effect of ezogabine on cortical and spinal motor neuron excitability in amyotrophic lateral sclerosis: a randomized clinical trial." JAMA neurology 78.2 (2021): 186-196.
Watanabe, Hirotaka, et al. "Disruption of the epilepsy KCNQ2 gene results in neural hyperexcitability." Journal of neurochemistry 75.1 (2000): 28-33.
Weckhuysen, Sarah, et al. "KCNQ2 encephalopathy: emerging phenotype of a neonatal epileptic encephalopathy." Annals of neurology 71.1 (2012): 15-25.
Yadav, Monu, et al. "Anesthetic management of craniopagus conjoined twins in a remote location." Saudi Journal of Anaesthesia 11.4 (2017): 516.
Zhang, XiChun, et al. "Ezogabine (KCNQ2/3 channel opener) prevents delayed activation of meningeal nociceptors if given before but not after the occurrence of cortical spreading depression." Epilepsy & Behavior 28.2 (2013): 243-248.

(56) References Cited

OTHER PUBLICATIONS

Wu, Zizhen, et al. "Enhancing KCNQ channel activity improves neurobehavioral recovery after spinal cord injury." Journal of Pharmacology and Experimental Therapeutics 373.1 (2020): 72-80.
Blackburn-Munro, G., et al. "Retigabine: chemical synthesis to clinical application." CNS drug reviews 11.1 (2005): 1-20.
Extended European Search Report for European Application No. 22772333.5 dated Mar. 18, 2025.
Simplício, Ana L., John M. Clancy, and John F. Gilmer. "Prodrugs for amines." Molecules 13.3 (2008): 519-547.
Soldovieri, Maria Virginia, Francesco Miceli, and Maurizio Taglialatela. "Driving with No. brakes: molecular pathophysiology of Kv7 potassium channels." Physiology 26.5 (2011): 365-376.

Compound 3 Stability, Solubility over 3 to 7 Days

Linear and Semilog Plot of Compound 1 and Compound 4 after administration of Compound 4 SC at 100 mg/kg in male mice.

Linear and Semilog Plot of Compound 1 and Compound 4 after administration of Compound 4 SC at 100 mg/kg in male mice.

Semilog Plot of Compound 1 after administration of either Compound 1 at 20 mg/kg, Compound 3 at 30 mg/kg or Compound 4 at 30 mg/kg in male mice by the oral route

Semilog Plot of N-acetyl metabolite after administration of either Compound 1 at 20 mg/kg, Compound 3 at 30 mg/kg or Compound 4 at 30 mg/kg in male mice by the oral route.

Semilog Plot of Compound 1 and Compound 4 after administration of Compound 4 IM at 75 mg/kg in male rat Semilog Plot of Compound 1 after administration of either Compound 1 at 20 mg/kg, Compound 3 at 30 mg/kg or Compound 4 at 30 mg/kg in male Sprague Dawley Rat by oral route.

Semilog Plot of N-acetyl metabolite after administration of either Compound 1 at 20 mg/kg, Compound 3 at 30 mg/kg or Compound 4 at 30 mg/kg in male mice by the oral route.

In vitro Screen of Kv7.2/7.3 Voltage Gated Potassium Channels

| Gram Force Withdrawal, Ipsilateral paw | | | | | | | | |
|---|---|---|---|---|---|---|---|---|
| | Dose | | | | | | | |
| | Baseline (g) | Vehicle | 40 mg/kg | 20 mg/kg | 10 mg/kg | 5 mg/kg | 1 mg/kg | Baseline (end) |
| Mean | 26.4 | 18.2 | 37.5 | 46.4 | 38.6 | 37.5 | 30.8 | 29.1 |
| SD | 10.4 | 8.2 | 14.3 | 15.1 | 13.9 | 14.4 | 14.5 | 7.9 |
| % contralateral | 37.1 | 28.8 | 57.5 | 74.4 | 60.8 | 58.7 | 49.1 | 45.6 |
| Gram Force Withdrawal, contralateral paw | | | | | | | | |
| Mean | 71.1 | 63.3 | 65.2 | 62.3 | 63.6 | 63.9 | 62.8 | 63.9 |
| SD | 6.2 | 14.7 | 16.4 | 9.3 | 13.3 | 13.3 | 12.0 | 9.2 |
| Seconds of Withdrawal, Ipsilateral paw | | | | | | | | |
| Dose | | | | | | | | |
| Animal No. | Baseline (g) | Vehicle | 40 mg/kg | 20 mg/kg | 10 mg/kg | 5 mg/kg | 1 mg/kg | Baseline (end) |
| Mean | 10.8 | 10.9 | 1.6 | 4.5 | 4.5 | 5.5 | 7.8 | 11.9 |
| SD | 3.5 | 3.8 | 1.3 | 4.8 | 2.1 | 4.1 | 3.7 | 3.3 |
| Fold dif contra | 21.5 | 34.8 | 2.8 | 8.0 | 14.8 | 12.6 | 15.5 | 15.8 |
| Seconds of Withdrawal, Contralateral paw | | | | | | | | |
| Mean | 0.5 | 0.3 | 0.6 | 0.6 | 0.3 | 0.4 | 0.5 | 0.8 |
| SD | 0.0 | 0.3 | 0.3 | 0.2 | 0.3 | 0.2 | 0.4 | 0.5 |

FIG. 15

Concentration (ng/mL) of Compound 28, Ezogabine and Pregabalin at 0.5 h post 24 mg/kg dose

PRODRUGS OF Kv7 CHANNEL OPENERS

CROSS-REFERENCE TO RELATED APPLICATION

This application is a U.S. National Stage application of PCT/US2022/021059, filed Mar. 20, 2022, which claims the benefit of U.S. Provisional Application No. 63/163,470, filed Mar. 19, 2021, the contents of each are hereby incorporated by reference.

FIELD OF THE DISCLOSURE

This disclosure relates to the field of prodrugs for pharmacologically-active drugs, and especially relates to the field of prodrugs of drugs active at Kv7 potassium ion channels. The prodrugs of this disclosure comprise one or more hydrolysable bonds between a pharmacologically-active drug or compound such as ezogabine, flupirtine, or other chemicals which are active at Kv7 potassium ion channels, and a carbonyl-containing prodrug side group, such as from an amino acid; or from a carbonyl-containing side group such as found in various acetal diester derivatives or ketal diester derivatives like the prodrug side group exemplified in gabapentin enacarbil that in of themselves are not active on Kv7 potassium ion channels. The hydrolysable bonds of the prodrugs of the disclosure are cleaved within the body of a mammal to generate the pharmacologically-active drugs.

BACKGROUND OF THE DISCLOSURE

Prodrugs:

Prodrugs are bioreversible derivatives of drug molecules that must undergo an enzymatic and/or chemical transformation in vivo to release the active parent drug, which can then exert its desired pharmacological effect.

In general, prodrugs are biologically inactive compounds that are activated post-administration to their pharmacologically active forms. Often prodrugs are formulated to overcome pharmacokinetic barriers such as poor solubility and absorption, extensive first-pass metabolism, lack of brain penetration, or rapid excretion, and physiochemical barriers such as poor stability, unwanted degradant products, or impurities and pharmacodynamic barriers such as toxicity, tolerability, side effects, and poor efficacy. The activation of prodrugs is usually via either enzymatic processes such as that by cytochrome enzymes, esterases and amidases or chemical processes (inter or intra-molecular) such as hydrolysis and oxidation.

The development of prodrugs is presently well established as a strategy for improving the physicochemical, biopharmaceutical or pharmacokinetic properties of pharmacologically potent compounds and thereby overcoming barriers to a drug's developability and usefulness.

Compounds Active at Kv7 Potassium Ion Channels:

Voltage-gated Kv7 (or KCNQ) channels play a pivotal role in controlling membrane excitability. The Kv7 subfamily of voltage-gated potassium channels consists of 5 members (Kv7.1-5) each showing characteristic tissue distribution and physiological roles. Given their functional heterogeneity, Kv7 channels represent important pharmacological targets for the development of new drugs for neuronal, neuromuscular, cardiovascular and metabolic diseases. Like typical voltage-gated ion channels, Kv7 channels undergo a closed-to-open transition by sensing changes in transmembrane potential, and thereby mediate inhibitory K(+) currents to reduce membrane excitability. Reduction of Kv7 channel activity as a result of genetic mutation is responsible for various human diseases due to membrane hyperexcitability, including epilepsy, arrhythmia and deafness. As a result, the discovery of small compounds that activate voltage-gated ion channels is an important strategy for clinical intervention in such disorders. Because ligand binding can induce a conformational change leading to subthreshold channel opening, there is considerable interest in understanding the molecular basis of these 'gain-of-function' molecules. Although small-molecule activators of cation channels are rare, several novel compounds that activate Kv7 voltage-gated channels have been identified.

Ezogabine (USAN, or retigabine [INN]) and flupirtine are two examples of compounds which are active at Kv7 $K^+$ channels and which have been developed into drugs but are no longer on the market as therapeutics.

Ezogabine is used along with other medications to control partial onset seizures (seizures that involve only one part of the brain) and focal seizures in adults and works by reducing neuronal hyperexcitability in the peripheral and central nervous system. Overall, the most frequently reported adverse reactions in patients receiving ezogabine provided under the brand name POTIGA®, a registered trademark of Valeant Pharmaceuticals North America, (≥4% and occurring at approximately twice the placebo rate) were dizziness (23%), somnolence (22%), fatigue (15%), confusional state (9%), vertigo (8%), tremor (8%), abnormal coordination (7%), diplopia (7%), disturbance in attention (6%), memory impairment (6%), asthenia (5%), blurred vision (5%), gait disturbance (4%), aphasia (4%), dysarthria (4%), and balance disorder (4%). In most cases the reactions were of mild or moderate intensity (Potiga label, revised May, 2016).

Ezogabine has exhibited effects in a range of cells, tissues, animal models and clinical trials related to the locations of these targets. In addition to blocking seizures, ezogabine has demonstrated pharmacological properties consistent with use as an analgesic, a neuroprotectant, in treatment of auditory disorders, a treatment of status epilepticus associated with organophosphate poisoning (Barker 2021, Neuroscience), and treatment of demyelinating diseases such as multiple sclerosis and amyotrophic lateral sclerosis. Ezogabine is providing important information and clues regarding novel mechanistic approaches to the treatment of a range of clinical conditions involving hyper-excitability of neurons.

Flupirtine has been used as a centrally-acting analgesic in patients with a range of acute and persistent pain conditions without the adverse effects characteristic of opioids and non-steroidal anti-inflammatory drugs and is well tolerated by the large majority of the patient population. The pharmacological profile exhibited by flupirtine involves actions on several cellular targets, including Kv7 channels, G-protein-regulated inwardly rectifying K channels and γ-aminobutyric acid type A receptors, but also there is evidence of additional as yet unidentified mechanisms of action involved in the effects of flupirtine.

Flupirtine has exhibited effects in a range of cells and tissues related to the locations of these targets. In additional to analgesia, flupirtine has demonstrated pharmacological properties consistent with use as an anticonvulsant, a neuroprotectant, skeletal and smooth muscle relaxant, in treatment of auditory and visual disorders, and treatment of memory and cognitive impairment. Flupirtine is providing important information and clues regarding novel mechanistic approaches to the treatment of a range of clinical conditions involving hyper-excitability of cells. However, flupirtine does have some unwanted side effects including nausea, vomiting, dizziness, itching, rash formation, abdominal pain, bloating, tremor, dry mouth, idiopathic hepatic toxicity, and fatigue.

Pharmacologically-active compounds which, more specifically, interact with Kv7.2 channel subtypes have also been studied (https://www.ncbi.nlm.nih.gov/pmc/articles/PMC2932606/) and may be useful as compounds which may be developed into drugs at a future date but to date only two drugs, ezogabine and flupirtine have been administered to humans as approved medical treatments.

Kv7 channels present interesting targets for new therapeutic approaches to diseases caused by neuronal hyperexcitability, such as epilepsy, neuropathic pain, and migraine. The molecular mechanism of Kv7 activation by retigabine, has been elucidated as a stabilization of the open conformation by binding to the pore region of Kv7 channels (J Physiol, Maljevic. 2008).

Literature research has demonstrated that Kv7 channel openers, such as retigabine, or pharmacological action that enhances the open state of Kv72-5 subtypes, have demonstrated, or are potentially effective, in treating, ameliorating, or preventing the progress of a disease or a disorder selected from the group diseases associated with neurological indications and pain. In one example, channel opening has demonstrated to be affected in affection the basal M-currents that set the resting membrane threshold. Enhancing the membrane threshold consisting of seizures Neurons from Kv7.2(S559A) knock-in mice showed normal basal M-currents. Knock-in mice displayed reduced M-current suppression when challenged by a muscarinic agonist, oxotremorine-M. Kv7.2(S559A) mice were resistant to chemoconvulsant-induced seizures with no mortality. Administration of XE991, a Kv7.2 blocker, transiently exacerbated seizures in knock-in mice equivalent to those of wildtype mice. After experiencing status epilepticus, Kv7.2 (S559A) knock-in mice did not show seizure-induced cell death nor spontaneous recurring seizures. (L Greene, Epilepsia 2018) This example presents how channel opening blocks seizures and neuroprotection. ICA-105665, a Kv7.2 channel opener reduced the SPR in patients at single doses of 100 (one of four), 400 (two of four), and 500 mg (four of six). This is the first assessment of the effects of activation of Kv7 potassium channels in the photosensitivity proof of concept model. The reduction of SPR in this patient population provides evidence of central nervous system (CNS) penetration by ICA-105665, and preliminary evidence that engagement with neuronal Kv7 potassium channels has antiseizure effects. (Epilepsia, Trenite, 2013).

In a model of pain, more specifically neuropathic pain, and chronic headache, Paclitaxel-induced peripheral neuropathy and associated neuropathic pain are severe and resistant to intervention. The results of a rodent model demonstrated that retigabine/ezogabine can be used to attenuate the development of paclitaxel-induced peripheral neuropathy. (J Pain, Li. 2019).

Several drugs including flupirtine and retigabine enhance neural Kv7/M-channel activity, principally through a hyperpolarizing shift in their voltage gating. In consequence they reduce neural excitability and can inhibit nociceptive stimulation and transmission. Flupirtine was one of the best selling non-opioid analgesics in Europe that work as a central analgesic before being removed from the market; retigabine is an analog of flupirtine and approved as adjunctive therapy in partial onset seizures and is a broad-spectrum anticonvulsant in animals and is an effective analgesic in animal models of chronic inflammatory and neuropathic pain central pain, pain related to diabetic neuropathy, to postherpetic neuralgia and to peripheral nerve injury (Brown Br J Pharmacology, 2009).

Czuzcwar has additionally summarized preclinical data that indicate that retigabine/ezogabine may possibly be applied in patients with neuropathic pain and affective disorders, such as drug addiction and affective disorders. Initial clinical data suggest that retigabine may be also effective in Alzheimer's disease or stroke. (Czuzcwar, Pharmacological Reports 2010).

There have been a number of articles that indicate that Kv7 channel opening can be effective in a number of neurological therapeutic targets, such as but not limited to, anxiety, CNS damage caused by neurodegenerative illness or diseases or injury, cognitive deficits, compulsive behavior, dementia, depressions, Huntington's disease, dystonia, mania. Since retigabine/ezogaibine and flupirtine are well tolerated in humans, the present finding of pronounced antidystonic efficacy in the dtsz mutant mice suggests that neuronal Kv7 channel activators are interesting candidates for the treatment of dystonia-associated dyskinesias and probably of other types of dystonias. The established analgesic effects of Kv7 channel openers might contribute to improvement of these disorders which are often accompanied by painful muscle spasms (Richter, Br J Pharmacology 2006).

In a recent article, retigabine could delay spreading depolarization onset following submaximal OGD stimulation. (Aiba, Brain 2021). Interestingly, Kv7.2 activators are neuroprotective in experimental ischemia and brain trauma studies and the anti-spreading depolarization properties of the activator may contribute to these neuroprotective effects. Further review of recent studies support the emerging roles of Kv7 channels in intrinsic and synaptic plasticity, and their contributions to cognition and behavior. The voltage-gated potassium channels of the KV7 family (KV7.2-5) play important roles in controlling neuronal excitability and are therefore attractive targets for treatment of CNS disorders linked to hyperexcitability and such diseases associated with hyperexcitability such as cognitive disorders, memory impairment, memory disorders, memory dysfunction. (See, for example, Boehm, Pain 2019; Maghera, Epilepsia 2020; De Jong, Physiological Reports 2018; Jakubowski, Epilepsy Behav 2013; Zizhen Wu, J Pharmacol Exp Ther 2020; J E Larsson, In Physiology 2020; Yadav, Saudi J Anaesth 2017; Garakani, Front Psychiatry 2020; Maljevic, J Physiol 2008; R. Brant, Gastroenterology 2017; Hui Sun, JCI Insight 2019; R Brant, Gastroenterology 2017; Ravi Misra, Gastroenterology 2017; Parreno, Front Physiol 2020; Blom, PLoS One. 2014) (Feng Neuroscience 2019) (E Redford, Physiol Biochem 2021) (J Gunthrope, Epilepsia 2012; Epilepsia, Villalba. 2018) (Frontal Physiol, Baculis. 2020; Frontal Physoil, Vigil. 2020).

Considering that Kv7 channels are critical for development and inhibition of neonatal brain (Peters et al., 2005; Soh et al., 2014), the memory impairment in these genetic models could be attributed to abnormal hippocampal morphology and/or hyperexcitability (Peters et al., 2005; Milh et al., 2020). Kv7 channels also regulate multiple behaviors. Behavioral phenotyping of the global or conditional homozygous KCNQ2 knock-out mice has not been possible due to their early postnatal lethality or premature death, respectively (Watanabe et al., 2000; Soh et al., 2014). However, heterozygous KCNQ2 knock-out mice are viable and display increased locomotor activity and exploratory behavior (Kim et al., 2020), consistent with behavioral hyperactivity induced by transgenic suppression of Kv7 currents (Peters et al., 2005) and amphetamine and XE991 (Sotty et al., 2009). These mice also show decreased sociability and increased repetitive and compulsive behavior (Kim et al., 2020), reminiscent of autism seen in some EE patients with dominant KCNQ2 mutations (Weckhuysen et al., 2012, 2013; Milh et al., 2013).

Recent animal research indicates that enhancing the M current (Kv7 opening) to be a therapeutic target for multiple brain disorders, including those with no current treatments, such as TBI and psychostimulant addiction and motion disorders, (Lee, J Neurophysio 2017), motor disorders, neurodegenerative diseases, Parkinson's disease, Parkinson-like motor disorders, (Jama Neurol, Wainger. 2021; Neurosci Bull, chen. 2017; Neural Plast, Ramirez. 2015) phobias, Pick's disease, psychosis, and bipolar disorder, (Frontal Physoil, Vigil. 2020).

Spinal cord damage can potential be treated with reducing the activity of neurons by opening KCNQ/Kv7 channels to protect spinal neurons and axons from degeneration after spinal cord injury, thereby promoting recovery of motor and sensory function. One study by We et al. demonstrated repeated application of retigabine to open these channels in the acute stage of injury promotes neurobehavioral recovery after spinal cord injury (Wu, J Pharmacol 2020).

Because of their important role in physiology, dysfunctional Kv7 channels are often linked to disorders characterized by abnormal potassium ion conductance, including cardiac arrhythmia, hearing impairment, epilepsy, pain, and hypertension Front Physiol, Iarsson. 2020; J Physoil, Maljevic. 2008).

In a study by Lee et al. provides evidence that mouse Kv7 channels may contribute differently to regulating the functional properties of cerebral and coronary arteries. Such heterogeneity has important implications for developing novel therapeutics for cardiovascular dysfunction. (Lee, Microcirculation, 2015).

Finally, Kv7 channels present interesting targets for new therapeutic approaches to diseases caused by neuronal hyperexcitability, such as epilepsy, neuropathic pain, and migraine. The molecular mechanism of Kv7 activation by retigabine has been recently elucidated as a stabilization of the open conformation by binding to the pore region which may be critical in the treatment of migraine and tension headache. (J Physoil, Maljevic. 2008).

Further experiments demonstrated that M current inhibition required concurrent rises in cytosolic Ca2+ concentration and depletion of membrane phosphatidylinositol 4,5-bisphosphate (PIP2). It's possible that PLC- and Ca 2/PIP2-mediated inhibition of M current in sensory neurons may represent one of the general mechanisms underlying pain produced by inflammatory mediators, and may therefore open up a new therapeutic window for treatment of this major clinical problem in bowel disorders, an inflammatory disease, such as ulcerative colitis, Crohn's disease and Creutzfeid-Jacobs disease (J Neurosci, Linley. 2008).

Additional Kv7 channel openers, such as QO58 can specifically activate Kv7.2/7.3/M-channels. Oral or intraperitoneal administration of QO58, can reverse inflammatory pain in rodent animal models (Acta Pharmacol Sin, Teng. 2016) and may be effective in peripheral hypertension.

Published data suggest that by stabilizing the KCNQ4-mediated conductance (Kv7.4) in cells associate with hearing, chemical channel openers can protect against degeneration and progression of hearing loss in DFNA2 mouse model which may be useful in progressive hearing loss or tinnitus (J Physoil, Maljevic. 2008).

Behavioral studies demonstrated that SF0034 was a more potent and less toxic anticonvulsant than retigabine in rodents. Furthermore, SF0034 prevented the development of tinnitus in mice. We propose that SF0034 provides, not only a powerful tool for investigating ion channel properties, but, most importantly, it provides a clinical candidate for treating epilepsy and preventing tinnitus (Br J Pharmacol, Leithner. 2014; J Neurosci, Kalappa. 2015).

The functional role of Kv7 channels may vary depending on the cell type. Several studies have demonstrated that the impairment of Kv7 channel has a strong impact on pulmonary physiology contributing to the pathophysiology of different respiratory diseases such as cystic fibrosis, asthma, chronic obstructive pulmonary disease, chronic coughing, lung cancer, and pulmonary hypertension. Kv7 channels are now recognized as playing relevant physiological roles in many tissues, which have encouraged the search for Kv7 channel modulators with potential therapeutic use in many diseases including those affecting the lung. Modulation of Kv7 channels has been proposed to provide beneficial effects in a number of lung conditions. Therefore, Kv7 channel openers/enhancers or drugs acting partly through these channels have been proposed as bronchodilators, expectorants, antitussives, chemotherapeutics and pulmonary vasodilators (Front Physiol, Mondejar-Parreno. 2020), and obesity, and disease associated hypertension (Front Cardivasc Med, Fosmo. 2017).

Further research into autism, autism spectrum disorders may suggest that administering a compound that has the potential to positively modulate Kv7 channels may be effective in these neurological diseases. Data suggest that dysfunction of the heteromeric KV7.3/5 channel is implicated in the pathogenesis of some forms of autism spectrum disorders, epilepsy, and possibly other psychiatric disorders and therefore, KCNQ3 and KCNQ5 are suggested as candidate genes for these disorders (Gilling, Front Genet. 2013; Guglielmi, Front Cell Neurosci. 2015).

The several background references are hereby incorporated by reference with regard to such teaching.

There is a need to more effectively deliver these compounds that are capable of interacting with Kv7.2 channel subtypes, specifically as prodrugs with improved properties at one or more of physicochemical, biopharmaceutical, or pharmacokinetic characteristics of pharmacologically potent compounds.

BRIEF SUMMARY OF THE DISCLOSURE

The present disclosure provides compounds which, inter alia, are useful in the treatment of diseases through the modulation of potassium ion flux through voltage-dependent potassium channels. More particularly, the disclosure provides prodrugs of compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, dysmenorrhea, vulvodynia, dysperunia, pain associated with endometriosis, multiple sclerosis, amyotrophic lateral sclerosis, spasticity, spasms, autism, Alzheimer's disease, age-related memory loss, learning deficiencies, anxiety and motor neuron diseases, organophosphate exposure, central and peripheral neuropathic pain conditions), and as neuroprotective agents (e.g., to prevent stroke, spinal and brain injury, retinal degeneration and the like). Compounds of the disclosure have use as prodrug agents for treating convulsive states, for example those following grand mal, petit mal, psychomotor epilepsy or focal seizure. The prodrug compounds of the disclosure are also useful in treating disease states such as restless leg syndrome, postherpetic neuralgia when metabolized or changed into the active compounds.

Moreover, compounds of the disclosure are useful as prodrugs in the treatment of pain, for example, neuropathic pain, diabetic pain, inflammatory pain, cancer pain, migraine pain, vulvar pain, abdominal pain and musculoskeletal pain. The compounds are also prodrugs which are metabolized to produce, in vivo, active compounds useful to treat conditions, which may themselves be the origin of pain, for example, inflammatory conditions, including arthritic conditions (e.g., rheumatoid arthritis, rheumatoid spondylitis, osteoarthritis and gouty arthritis) and non-articular inflammatory conditions (e.g., herniated, ruptured and prolapsed disc syndrome, bursitis, tendonitis, tenosynovitis, fibromyalgia syndrome, and other conditions associated with ligamentous sprain and regional musculoskeletal strain) and pain associated with neuronal demyelinating diseases. Particularly preferred compounds of the disclosure may exhibit lower central nervous system side effects, such as dizziness and somnolence, due to a more controlled release of the active drug. Furthermore, the compounds of the disclosure are prodrugs which metabolize in vivo into compounds useful in treating conditions and pain associated with abnormally raised skeletal muscle tone.

The compounds of the disclosure are also prodrugs of compounds of use in treating anxiety (e.g. anxiety disorders) and depression. These disorders include separation anxiety disorder, selective mutism, specific phobia, social anxiety disorder (social phobia), panic disorder, agoraphobia, generalized anxiety disorder, substance/medication-induced anxiety disorder, and anxiety disorder due to another medical condition.

Anxiety also occurs as a symptom associated with other psychiatric disorders, for example, obsessive compulsive disorder, post-traumatic stress disorder, schizophrenia, mood disorders and major depressive disorders, and with organic clinical conditions including, but not limited to, Parkinson's disease, multiple sclerosis, and other physically incapacitating disorders.

In view of the above-noted discovery, the present disclosure provides prodrugs of compounds, as well as compositions comprising these prodrugs of compounds, and methods for increasing ion flux in voltage-dependent potassium channels, particularly those channels responsible for the M-current. As used herein, the term "M-current," "channels responsible for the M-current" and the like, refers to a slowly activating, non-inactivating, slowly deactivating voltage-gated $K^+$ channel. M-current is active at voltages close to the threshold for action potential generation in a wide variety of neuronal cells, and thus, is an important regulator of neuronal excitability.

Members of the voltage-dependent potassium channel family have been shown to be directly involved in diseases of the central or peripheral nervous system. The prodrugs of compounds provided herein are now shown to be metabolized and release compounds which act as potassium channel modulators, particularly openers, for KCNQ2 and KCNQ3, KCNQ4, and KCNQ5 as well as the heteromultimer channels such as KCNQ2/3, KCNQ3/5 or the M-current.

One embodiment of the present disclosure includes a compound of Formula I:

Formula I

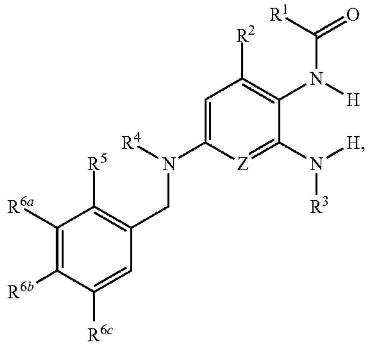

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is N or CH;

$R^3$ is "Pro" wherein "Pro" is selected from the group consisting of $C(O)R^{10}$;

$R^{10}$ is a hydrolysable prodrug moiety of the structure $C(O)OL^1OC(O)R^{11}$, where $R^{11}$ is unsubstituted or substituted $C_1$-$C_{10}$ alkyl, aryl, $C_1$-$C_{10}$ aralkyl;

$L^1$ is $C_1$-$C_{10}$ alkylene, wherein the two oxygen atoms depicted as attached to $L^1$ are on the same carbon atom within $L^1$;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, or a pharmaceutically acceptable salt thereof.

One embodiment of the present disclosure includes a compound of Formula II

Formula II

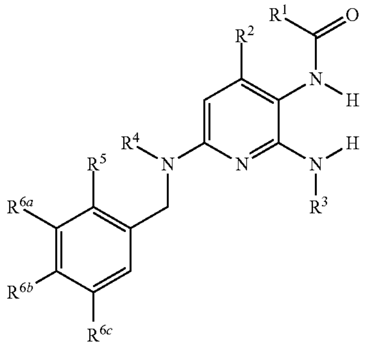

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

$R^3$ is "Pro" wherein "Pro" is selected from the group consisting of $C(O)R^{10}$;

$R^{10}$ is a hydrolysable prodrug moiety of the structure $C(O)OL^1OC(O)R^{11}$, where $R^{11}$ is unsubstituted or substituted $C_1$-$C_{10}$ alkyl, aryl, $C_1$-$C_{10}$ aralkyl;

$L^1$ is $C_1$-$C_{10}$ alkylene, wherein the two oxygen atoms depicted as attached to $L^1$ are on the same carbon atom within $L^1$;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, or a pharmaceutically acceptable salt thereof.

One embodiment of the present disclosure includes a compound of Formula III:

Formula III

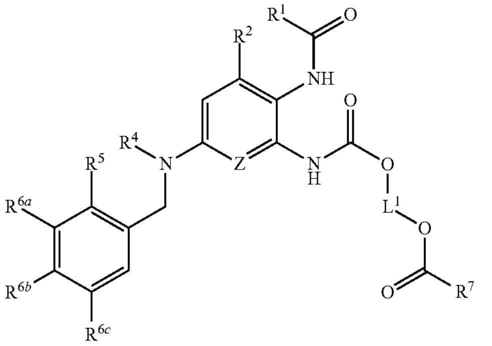

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is N or CH;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, $R^7$ is $C_{1-6}$ alkyl, phenyl, or $C_{1-2}$ alkyl-phenyl, or a pharmaceutically acceptable salt thereof.

One embodiment of the present disclosure includes a compound of claim 3, wherein the compound is of Formula III-A:

Formula III-A

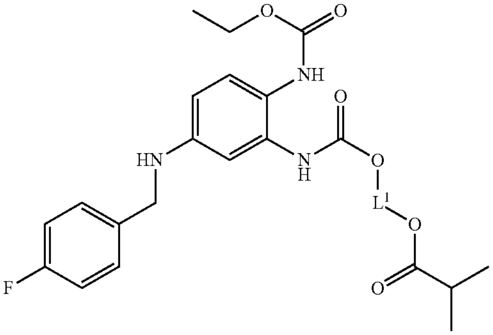

wherein $L^1$ is $C_1$-$C_{10}$ alkylene wherein the two depicted oxygen atoms on $L^1$ are on the same carbon atom within $L^1$, or a pharmaceutically acceptable salt thereof.

One embodiment of the present disclosure includes a compound or a pharmaceutically acceptable salt thereof:

Compound 3

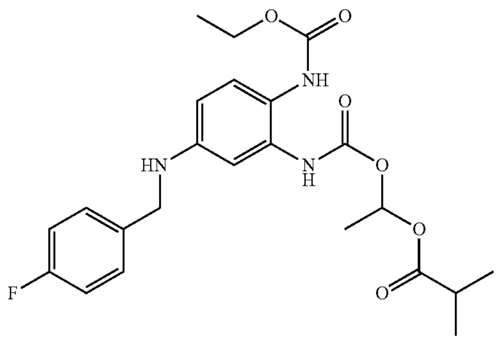

One embodiment of the present disclosure includes a compound of Formula IV:

Formula IV

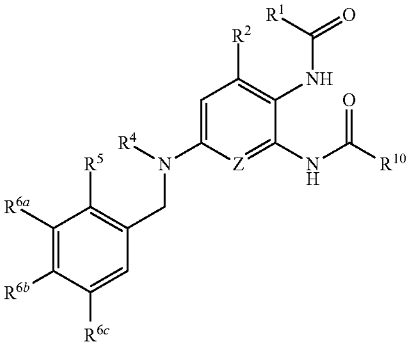

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is N or CH;

$R^{10}$ is a hydrolysable prodrug moiety of the structure $C(O)OL^1OC(O)R^{11}$, where $R^{11}$ is unsubstituted or substituted $C_1$-$C_{10}$ alkyl, aryl, $C_1$-$C_{10}$ aralkyl;

$L^1$ is $C_1$-$C_{10}$ alkylene, wherein the two oxygen atoms depicted as attached to $L^1$ are on the same carbon atom within $L^1$;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, or a pharmaceutically acceptable salt thereof.

One embodiment of the present disclosure includes a pharmaceutical composition comprising a compound of the present disclosure and one or more pharmaceutically acceptable excipient.

One embodiment of the present disclosure includes a method of eliciting one or more of an anti-epileptic, muscle relaxing, fever reducing, peripherally analgesic, or anticonvulsive effect in a patient in need thereof comprising administering an effective amount of a compound of the present disclosure.

One embodiment of the present disclosure includes a method of treating one or more of depression, including depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including agoraphobia, social phobia or simple phobias; eating disorders, including anorexia nervosa or bulimia nervosa; chemical dependencies, including addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, including dementia in Parkinson's disease, neuroleptic-induced parkinsonism or tardive dyskinesias; headache, including headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease, comprising administering a compound of the present disclosure.

One embodiment of the present disclosure includes a method of treating, ameliorating, or preventing the progress of a disease or a disorder selected from the group consisting of seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorders, phobias, Pick's disease, psychosis, a bipolar disorder, Schizophrenia, schizophrenia subtypes being the catatonic-subtype, the paranoid-subtype, the disorganized subtype or the residual subtype, Spinal cord damage, cardiomyopathia, cardiac arrhythmia, long QTSyndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, or meta Static tumor growth, a pneumoconiosis, Such as aluminosis, anthracosis, asbestosis, chalicosis, ptilosis, Siderosis, Silicosis, tabacosis and by Sinosis, and a chronic obstructive pulmonary disease (COPD), and obesity and disease associated hypertension, comprising administering a compound of the present disclosure.

One embodiment of the present disclosure includes a method of treating one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, autism spectrum disorders, comprising administering a compound of the present disclosure.

One embodiment of the present disclosure includes a method of delivering a broad spectrum Kv7.2-7.5 active molecule to systemic circulation and releasing said active Kv channel opener in an effective concentration at therapeutic concentrations to treat one or more susceptible disease or disorder comprising administering a compound of the present disclosure. In one aspect, release of the active molecule is provided under one or more of:

enhanced by increased absorption by the clinical route of administration;

delayed in the time to onset to improve treatment emergent adverse events; and increase the half-life or residence time through delayed circulation and release, thus negating the need for development of a modified, sustained, delayed, or extended release formulation.

One embodiment of the present disclosure includes a method of enhancing chemical stability and reduction of impurities and degradants in the manufacturing of drug substance and drug product thus improving the use and tolerability of the drug.

One embodiment of the present disclosure includes use of a compound of the present disclosure for the manufacture of a medicament to elicit one or more of an anti-epileptic, muscle relaxing, fever reducing, peripherally analgesic, or anticonvulsive effect in a patient in need thereof.

One embodiment of the present disclosure includes use of a compound of the present disclosure for the manufacture of a medicament to treat one or more of depression, including depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including agoraphobia, social phobia or simple phobias; eating disorders, including anorexia nervosa or bulimia nervosa; chemical dependencies, including addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, including dementia in Parkinson's disease, neuroleptic-induced parkinsonism or tardive dyskinesias; headache, including headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

One embodiment of the present disclosure includes use of a compound of the present disclosure for the manufacture of a medicament to treat, ameliorate, or prevent the progress of a disease or a disorder selected from the group consisting of seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorders, phobias, Pick's disease, psychosis, a bipolar disorder, Schizophrenia, schizophrenia subtypes being the catatonic-subtype, the paranoid-subtype, the disorganized subtype or the residual subtype, Spinal cord damage, cardiomyopathia, cardiac arrhythmia, long QTSyndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, or meta Static tumor growth, a pneumoconiosis, Such as aluminosis, anthracosis, asbestosis, chalicosis, ptilosis, Siderosis, Silicosis, tabacosis and by Sinosis, and a chronic obstructive pulmonary disease (COPD), and obesity and disease associated hypertension.

One embodiment of the present disclosure includes use of a compound of the present disclosure for the manufacture of a medicament to treat one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, autism spectrum disorders.

One embodiment of the present disclosure includes a use of a compound of the present disclosure for the manufacture of a medicament to deliver a broad spectrum Kv7.2-7.5 active molecule to systemic circulation and releasing said active Kv channel opener in an effective concentration at therapeutic concentrations to treat one or more susceptible disease or disorder. In one aspect, release of the active molecule is provided under one or more of:

enhanced by increased absorption;

delayed in the time to onset to improve treatment emergent adverse events; and increase the half-life or residence time through delayed circulation and release, thus negating the need for development of a modified, sustained, delayed, or extended release formulation.

One embodiment of the present disclosure includes a compound of the present disclosure for use in eliciting one or more of an anti-epileptic, muscle relaxing, fever reducing, peripherally analgesic, or anticonvulsive effect in a patient in need thereof.

One embodiment of the present disclosure includes a compound of the present disclosure for use in treating one or more of depression, including depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including agoraphobia, social phobia or simple phobias; eating disorders, including anorexia nervosa or bulimia nervosa; chemical dependencies, including addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, including dementia in Parkinson's disease, neuroleptic-induced parkinsonism or tardive dyskinesias; headache, including headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

One embodiment of the present disclosure includes a compound of the present disclosure for use in treating, ameliorating, or preventing the progress of a disease or a disorder selected from the group consisting of seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorders, phobias, Pick's disease, psychosis, a bipolar disorder, Schizophrenia, schizophrenia subtypes being the catatonic-subtype, the paranoid-subtype, the disorganized subtype or the residual subtype, Spinal cord damage, cardiomyopathia, cardiac arrhythmia, long QTSyndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, or meta Static tumor growth, a pneumoconiosis, Such as aluminosis, anthracosis, asbestosis, chalicosis, ptilosis, Siderosis, Silicosis, tabacosis and by Sinosis, and a chronic obstructive pulmonary disease (COPD), and obesity and disease associated hypertension.

One embodiment of the present disclosure includes a compound of the present disclosure for use in treating one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, autism spectrum disorders.

One embodiment of the present disclosure includes a compound of the present disclosure for use in delivering a broad spectrum Kv7.2-7.5 active molecule to systemic circulation and releasing said active Kv channel opener in an effective concentration at therapeutic concentrations to treat one or more susceptible disease or disorder. In one aspect, release of the active molecule is provided under one or more of:

- enhanced by increased absorption;
- delayed in the time to onset to improve treatment emergent adverse events; and increase the half-life or residence time through delayed circulation and release,
- thus negating the need for development of a modified, sustained, delayed, or extended release formulation.

One or more aspects and embodiments may be incorporated in a different embodiment although not specifically described. That is, all aspects and embodiments may be combined in any way or combination.

Figure 5A:
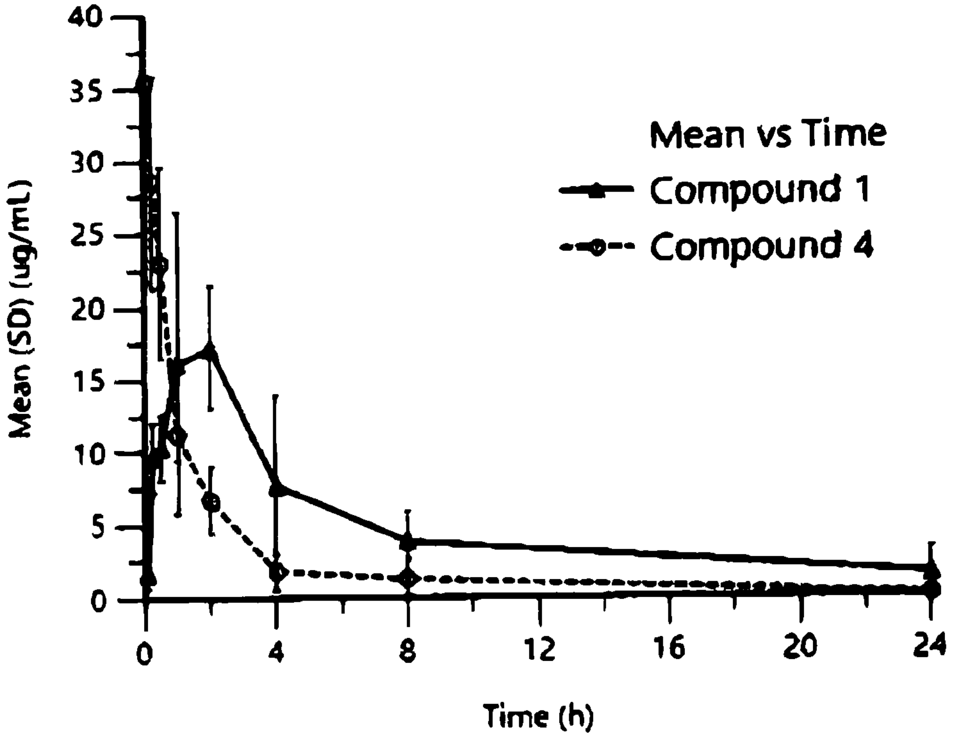
Figure 5B:
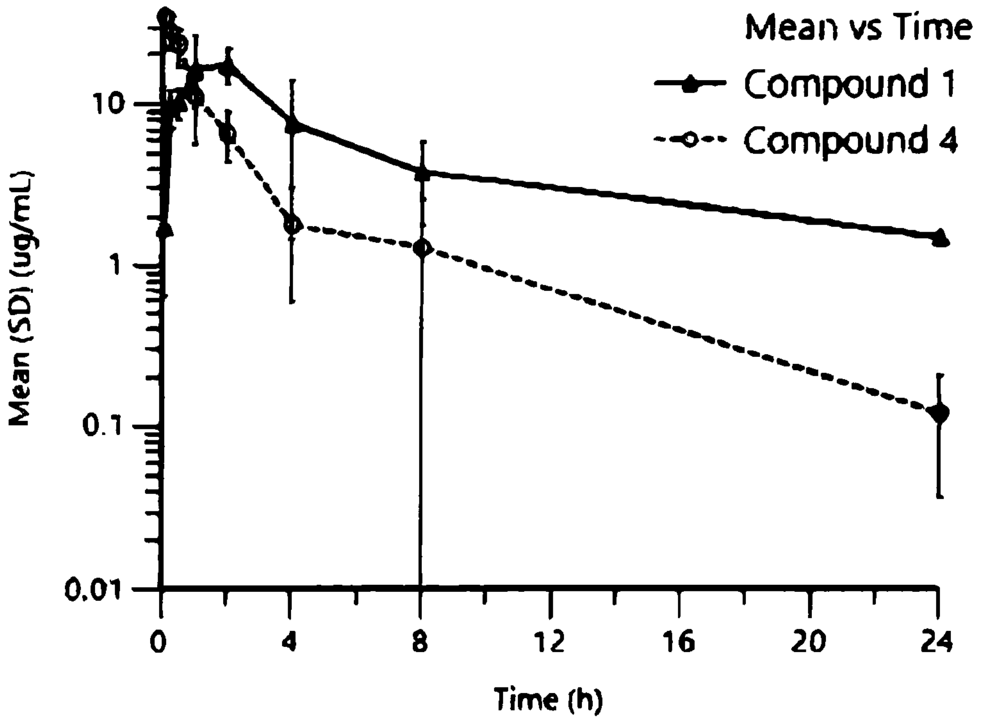

Each of FIGS. 5A and 5B is a graphical illustration of Linear and Semilog Plots, respectively, of Compound 1 and Compound 4 after administration of Compound 4 SC at 100 mg/kg in male mice.

Figure 6:
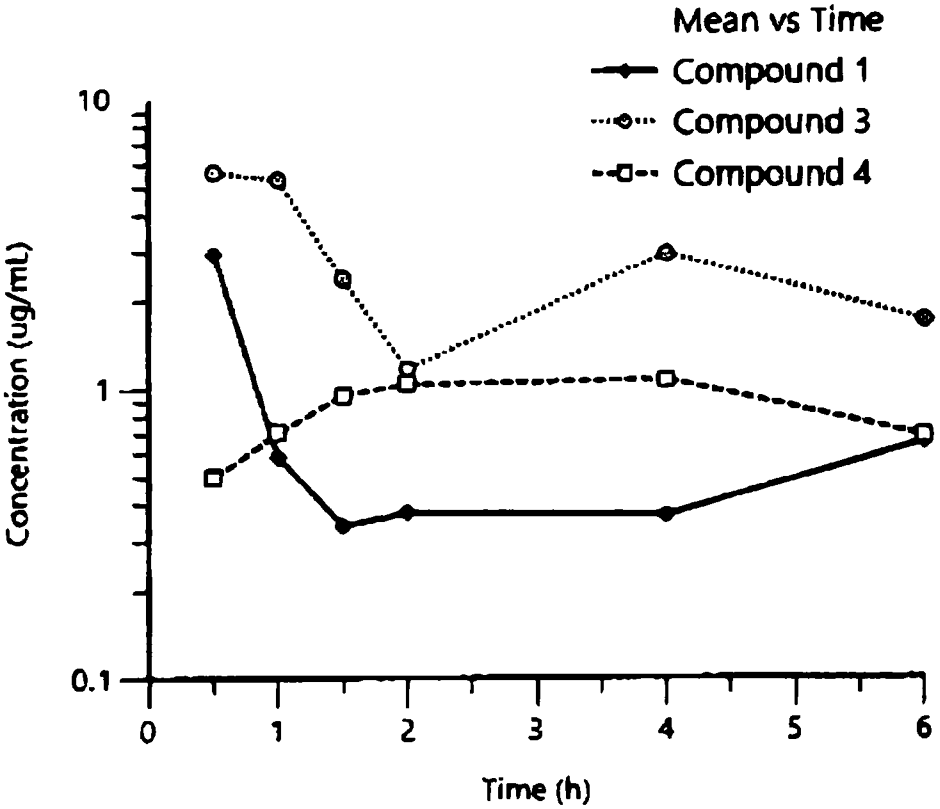

FIG. 6 is a graphical illustration of Semilog Plot of Compound 1 after administration of either Compound 1 at 20 mg/kg, Compound 3 at 30 mg/kg or Compound 4 at 30 mg/kg in male mice by the oral route.

Figure 7:
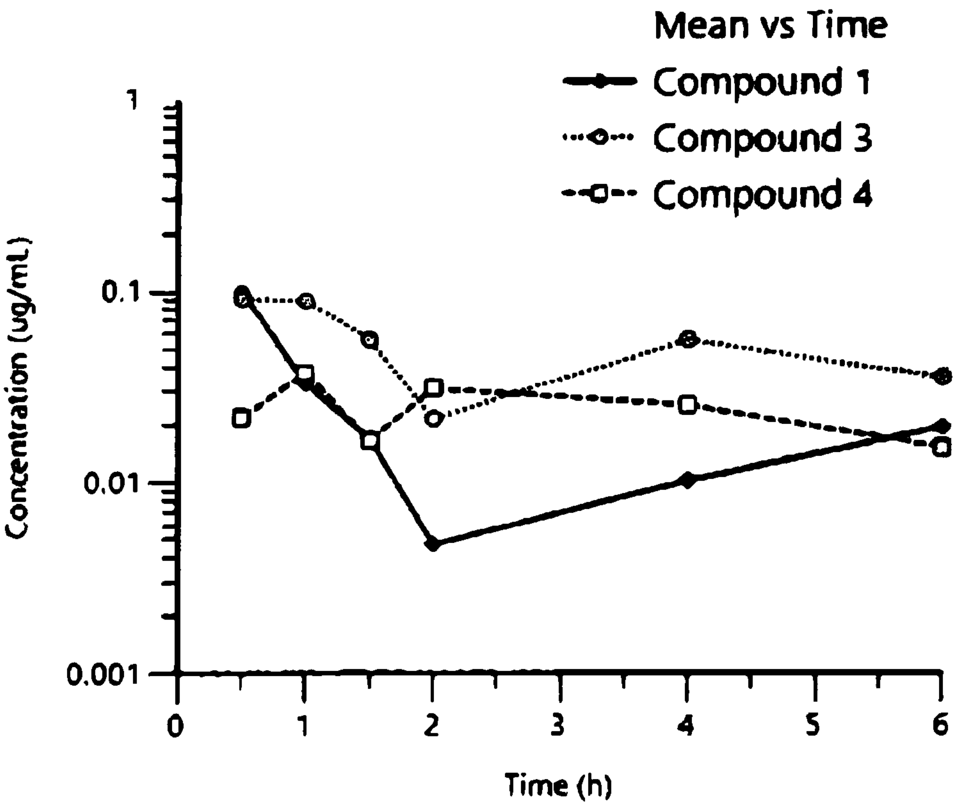

FIG. 7 is a graphical illustration of Semilog Plot of N-acetyl metabolite after administration of either Compound 1 at 20 mg/kg, Compound 3 at 30 mg/kg or Compound 4 at 30 mg/kg in male mice by the oral route.

Figure 8:
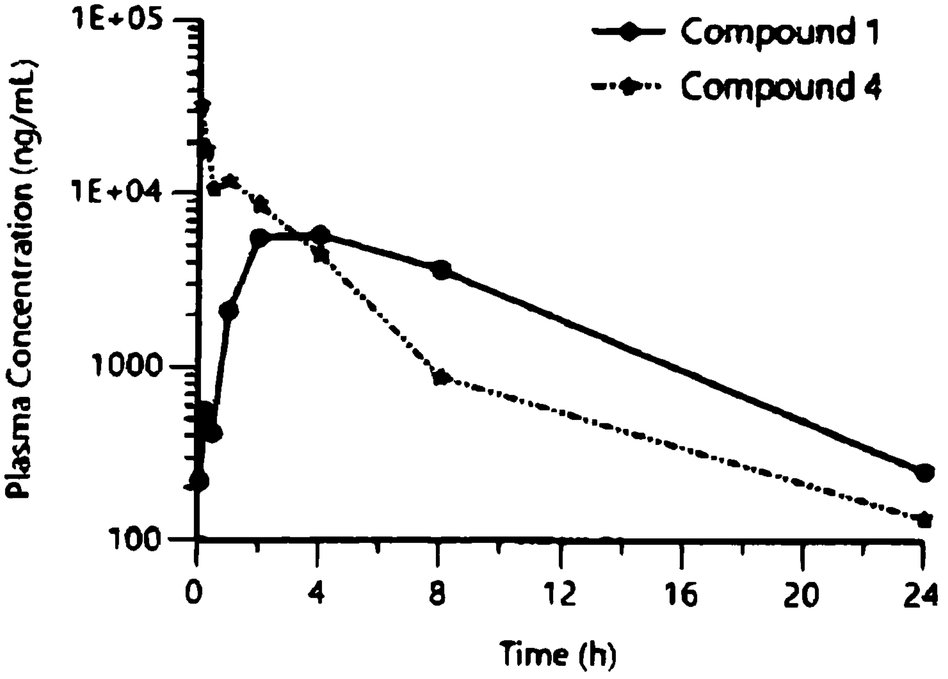

FIG. 8 is a graphical illustration of Semilog Plot of Compound 1 and Compound 4 after administration of Compound 4 IM at 75 mg/kg in male rat.

Figure 9:
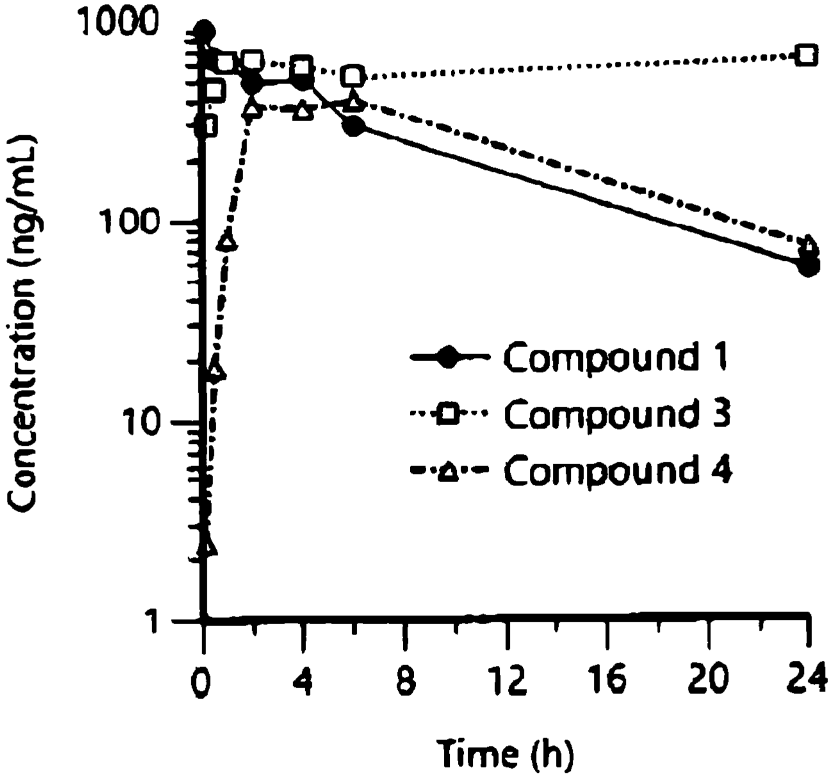

FIG. 9 is a graphical illustration of Semilog Plot of Compound 1 after administration of either Compound 1 at 20 mg/kg, Compound 3 at 30 mg/kg or Compound 4 at 30 mg/kg in male Sprague Dawley Rat by the oral route.

Figure 10:
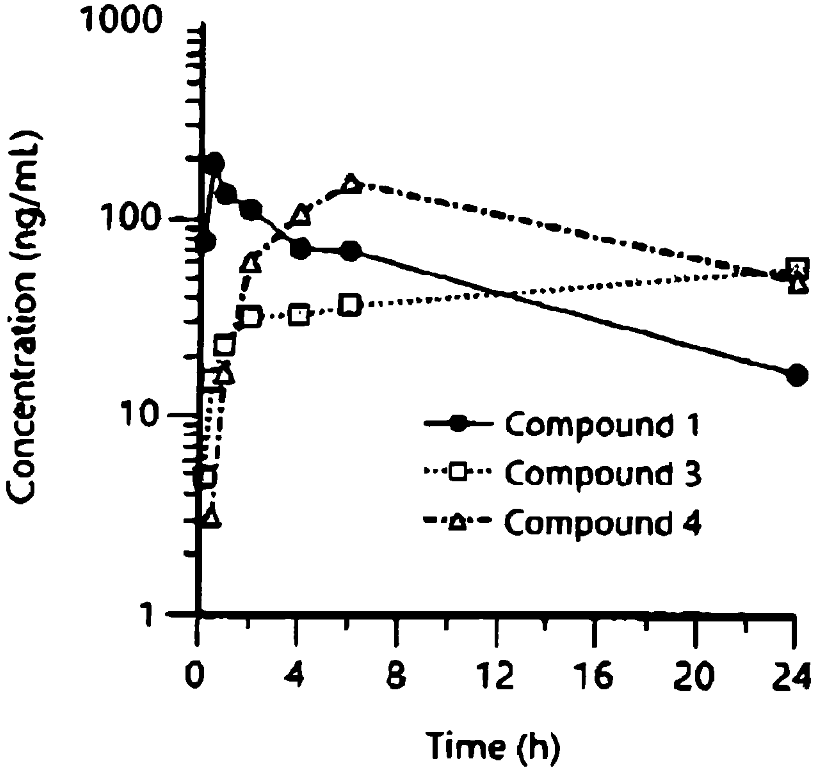

FIG. 10 is a graphical illustration of Semilog Plot of N-acetyl metabolite after administration of either Compound 1 at 20 mg/kg, Compound 3 at 30 mg/kg or Compound 4 at 30 mg/kg in male mice by the oral route.

Figure 11:
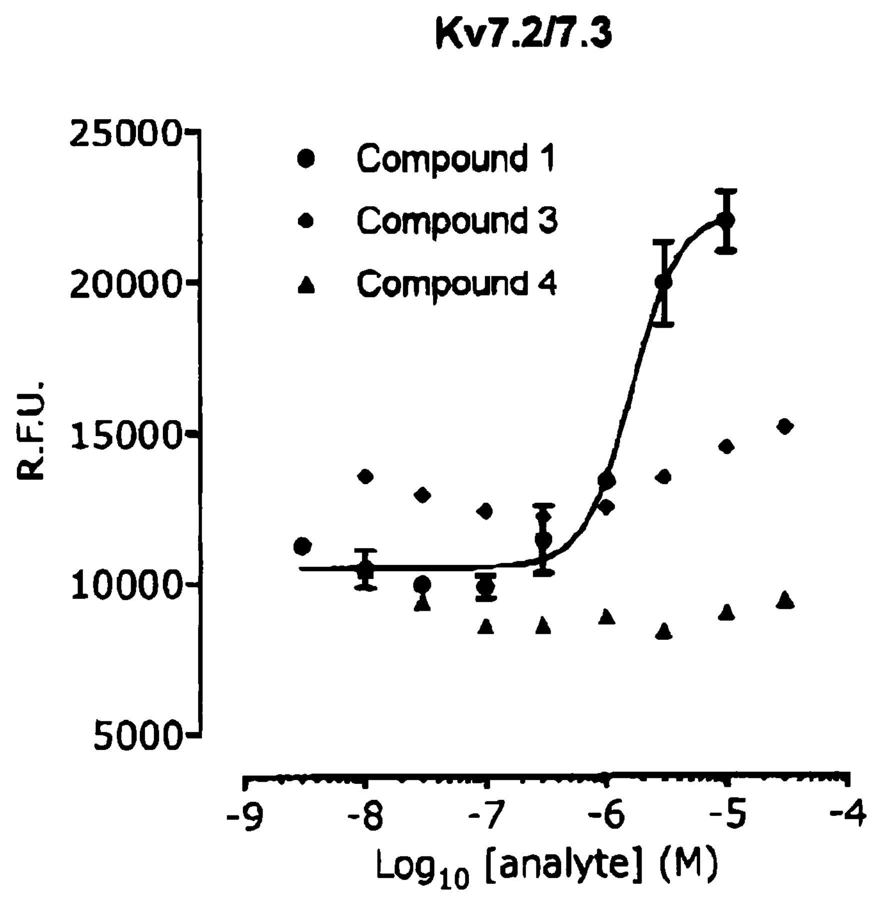

FIG. 11 is a graphical illustration of an In vitro Screen of Kv7.2/7.3 Voltage Gated Potassium Channels.

Figure 12:
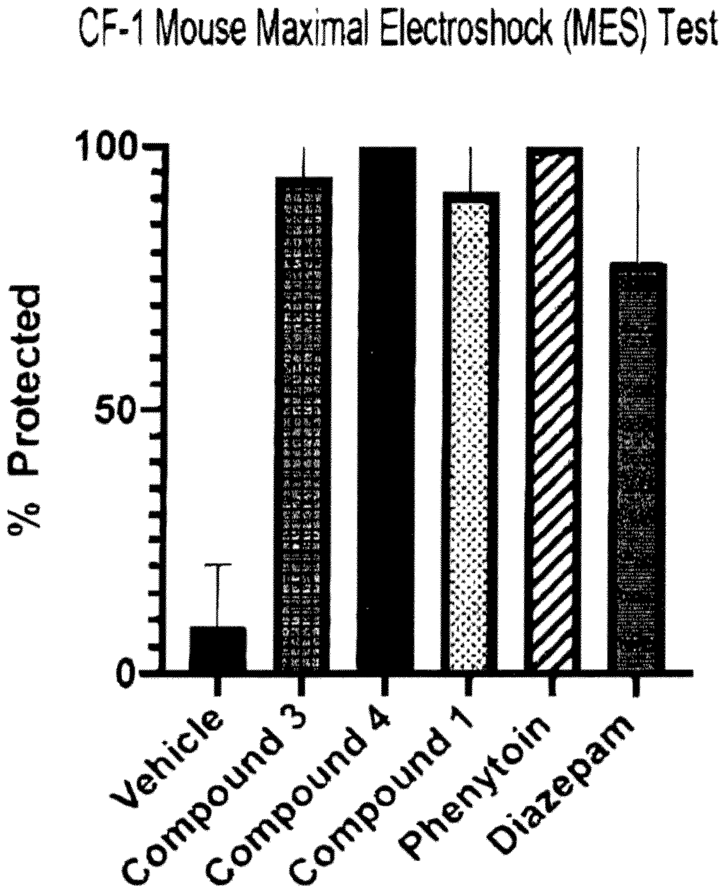

FIG. 12 is a graphical illustration of testing within a CF-1 Mouse Maximal Electroshock (MES) Test.

Figure 13:
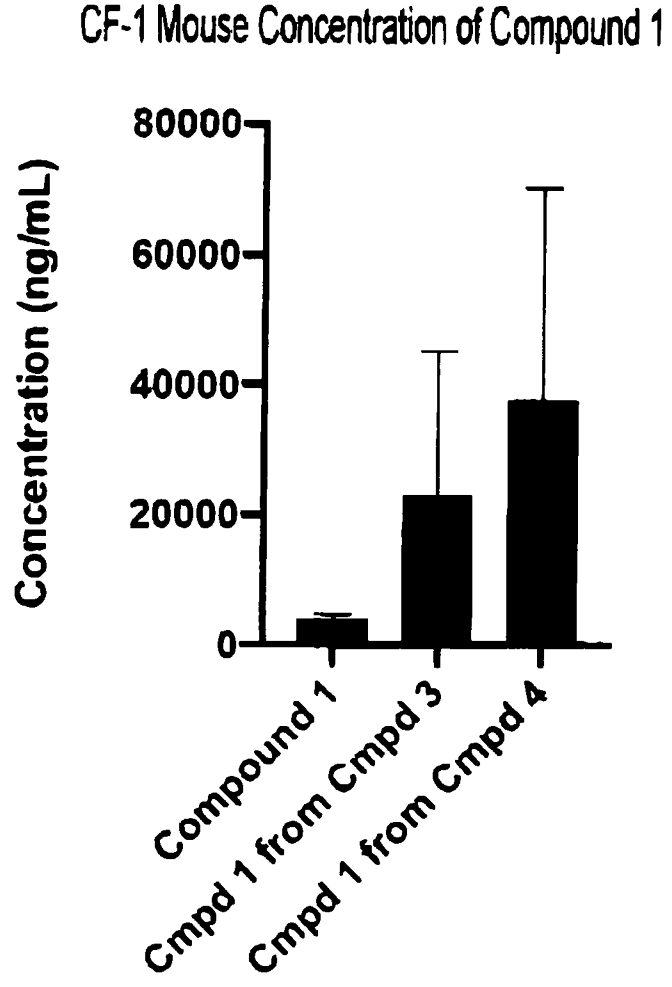

FIG. 13 is a graphical illustration of CF-1 Mouse Concentration of Compound 1.

Figure 14:
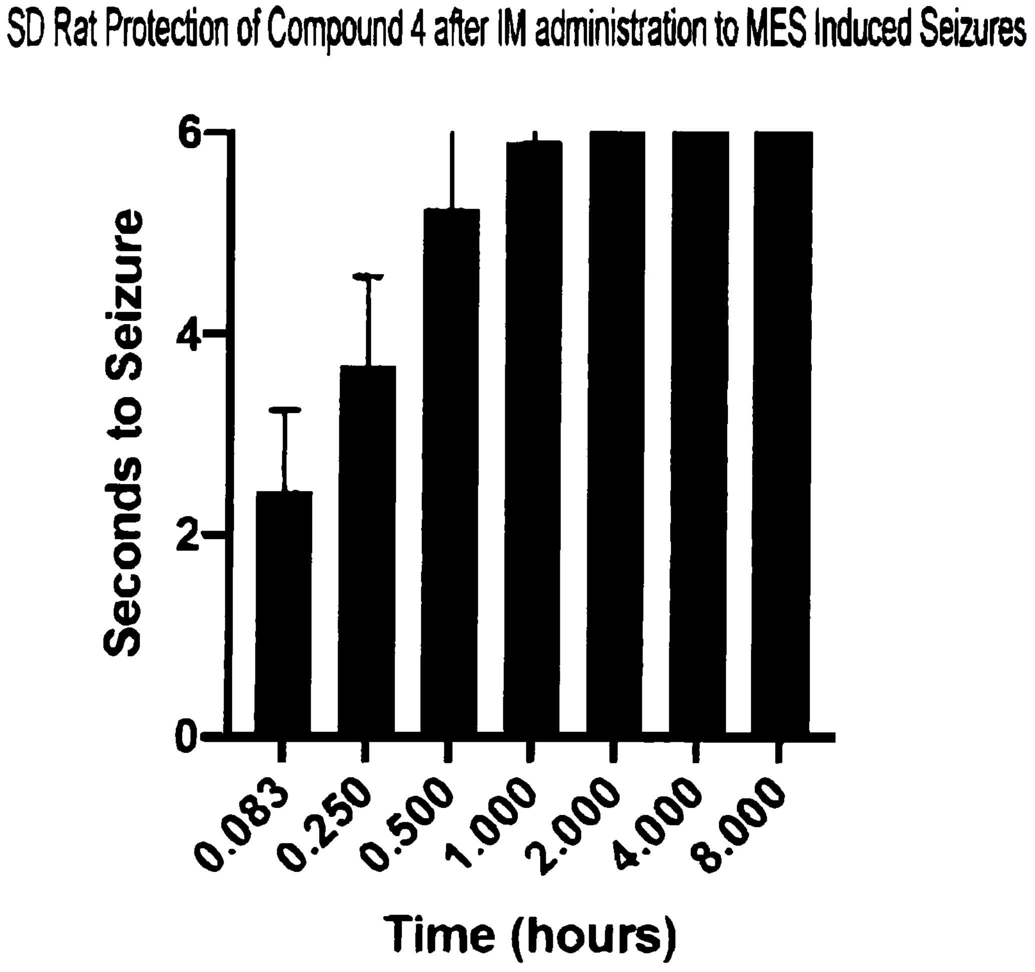

FIG. 14 is a graphical illustration of SD Rat Protection of Compound 4 after IM administration to MES Induced Seizures.

Figure 16:
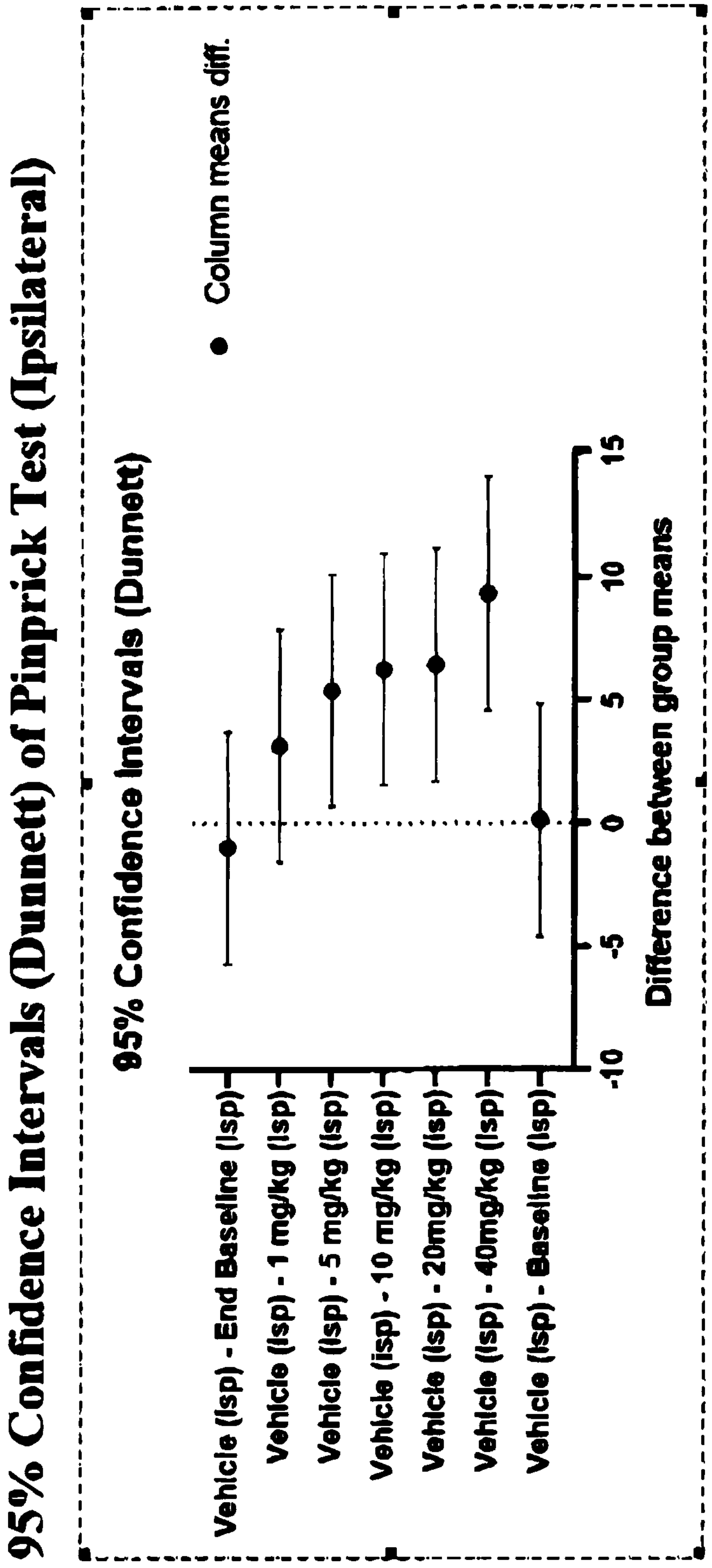

FIG. 15 is a table presenting dose related responses for XYZ-203/Compound 3 from a CCI model of neuropathic pain FIG. 16 is a graphic illustration of the results for XYZ-203 (Compound 3) from a CCI model of neuropathic pain.

Figure 17:
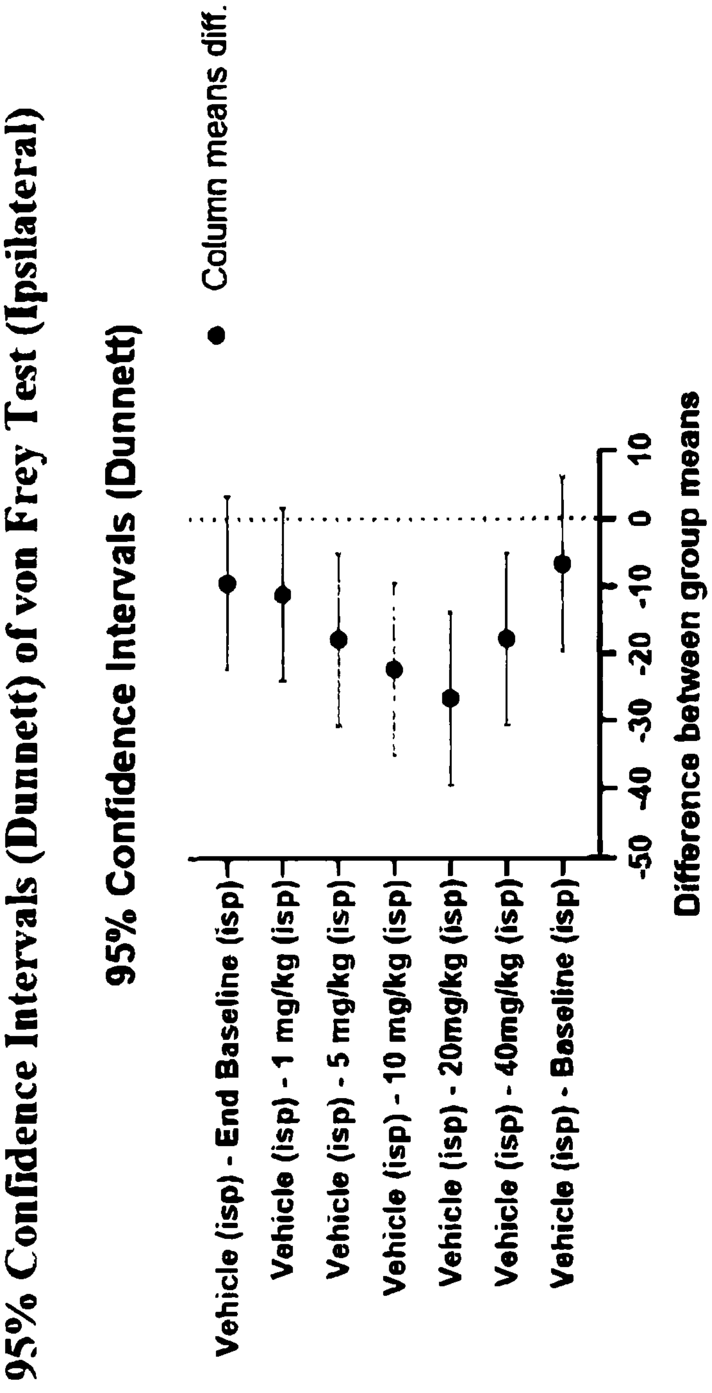

FIG. 17 is a graphic illustration of the results for XYZ-203 (Compound 3) from a CCI model of neuropathic pain.

Figure 18:
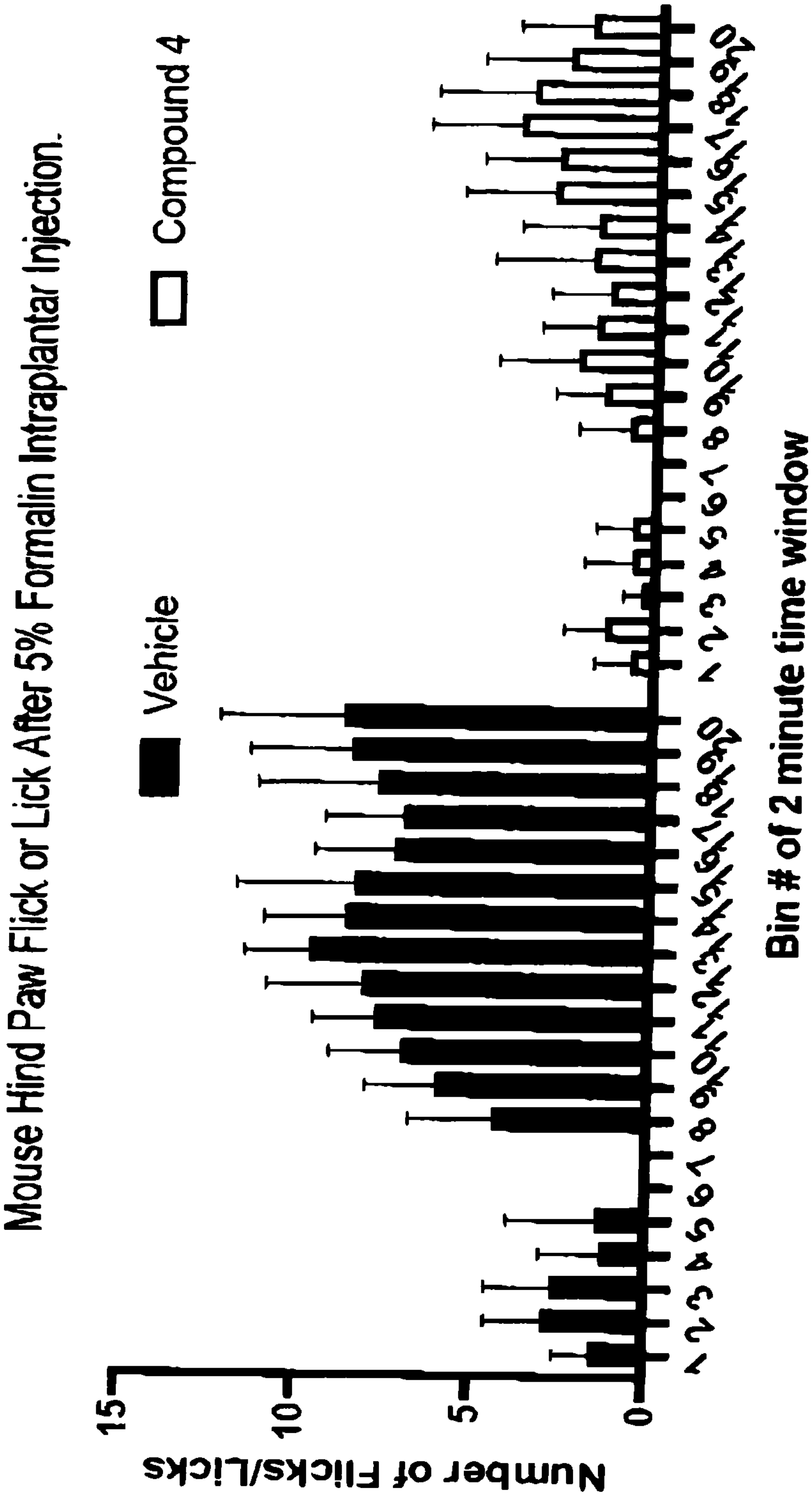

FIG. 18 is a graphical illustration of Mouse Hind Paw Flick or Lick After 5% Formalin Intraplantar Injection.

Figure 19:
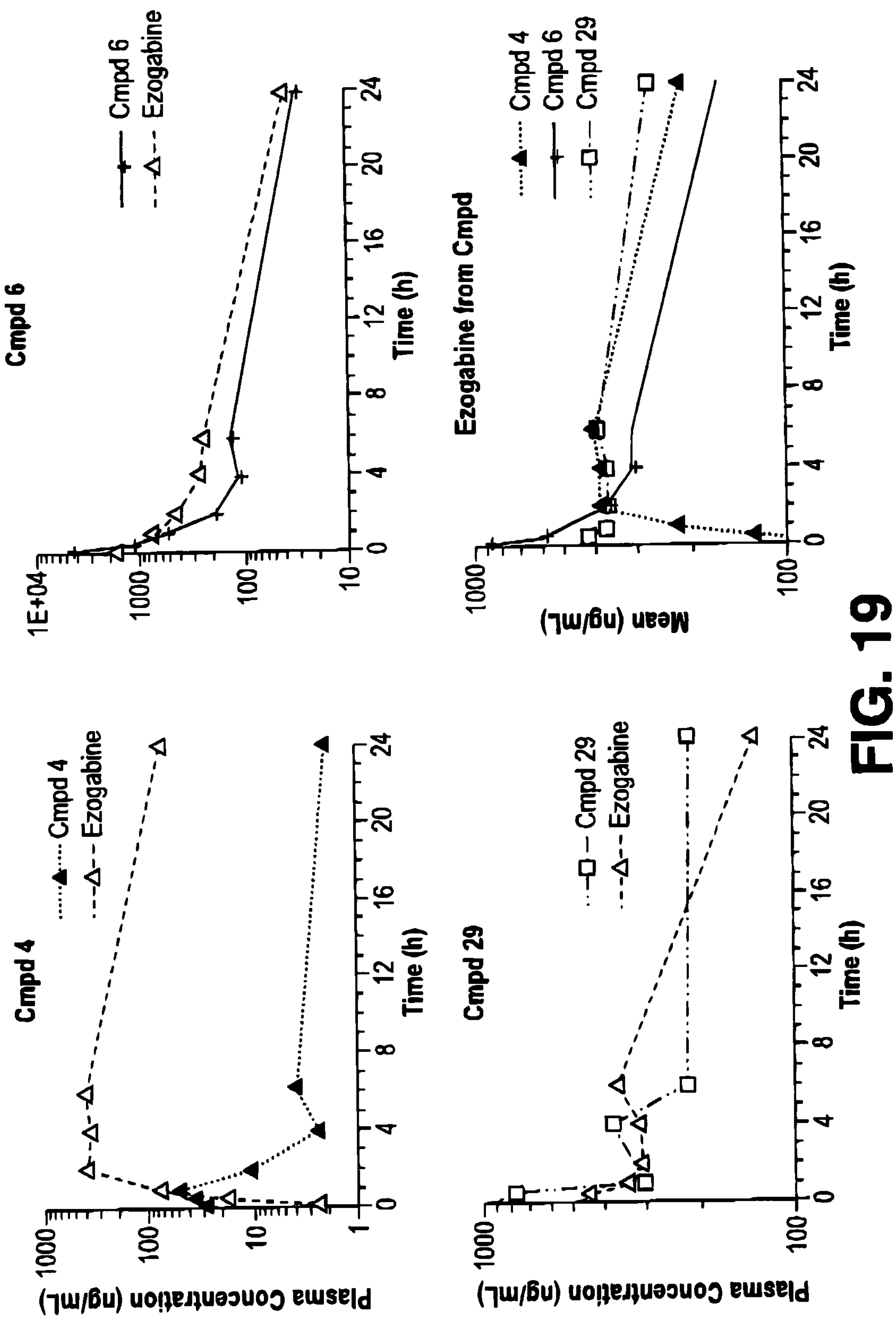

FIG. 19 is a graphical illustration of Compounds 4, 6 and 2 dosed at an equimolar dose to Ezogabine (20 mg/kg) with the same formulation (0.5% methylcellulose in water) in male jugular vein cannulated rats.

Figure 20:
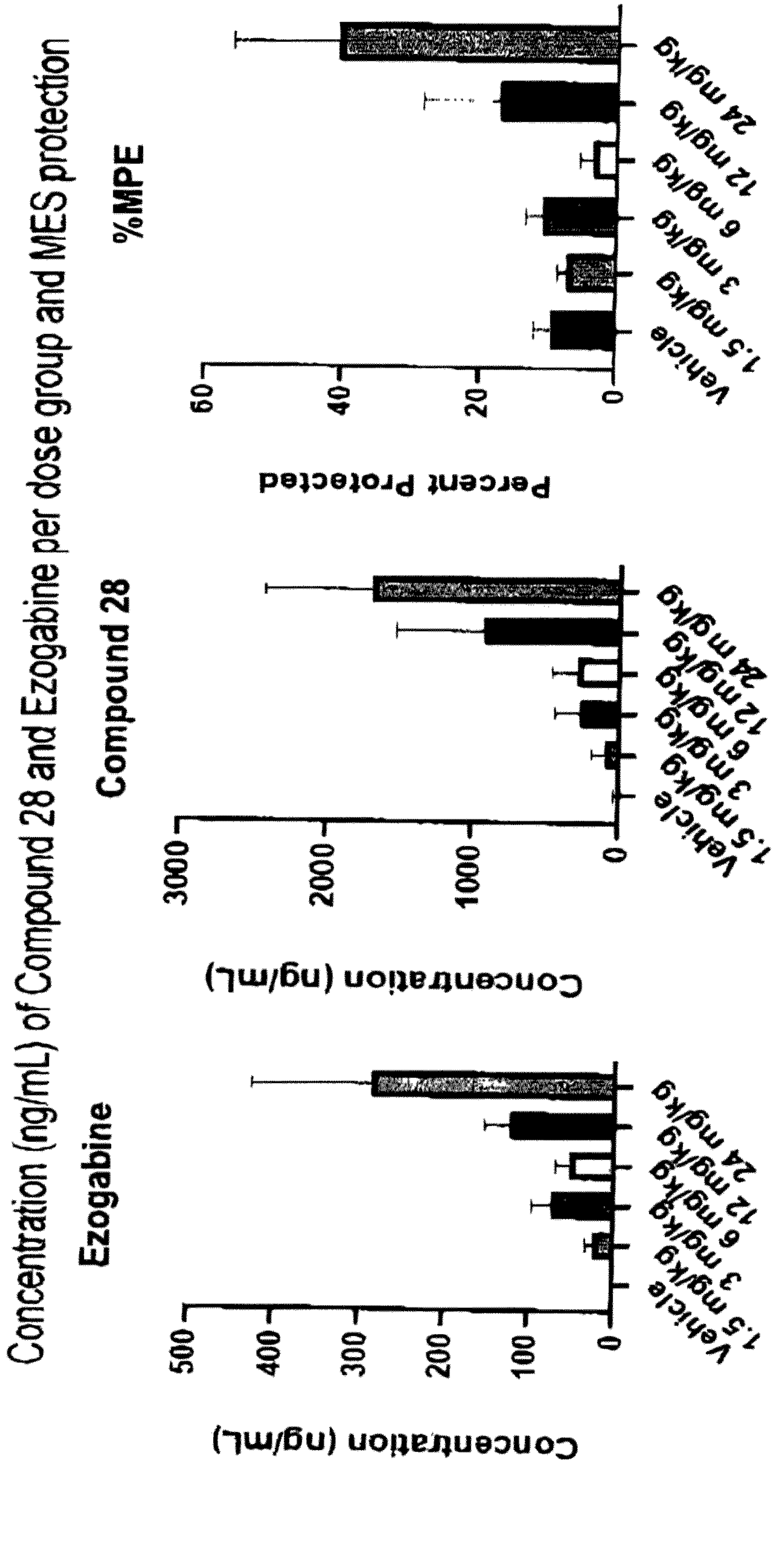

FIG. 20 is a graphical description of the concentration (ng/mL) of Compound 28 and Ezogabine per dose group and MES protection.

Figure 21:
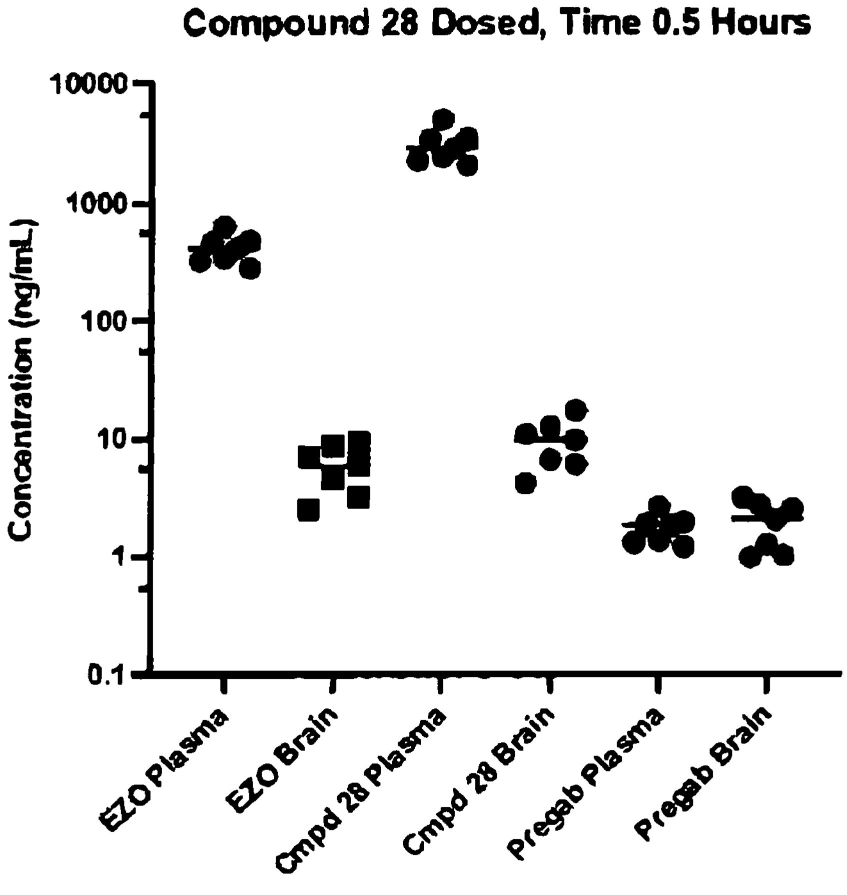
Figure 22:
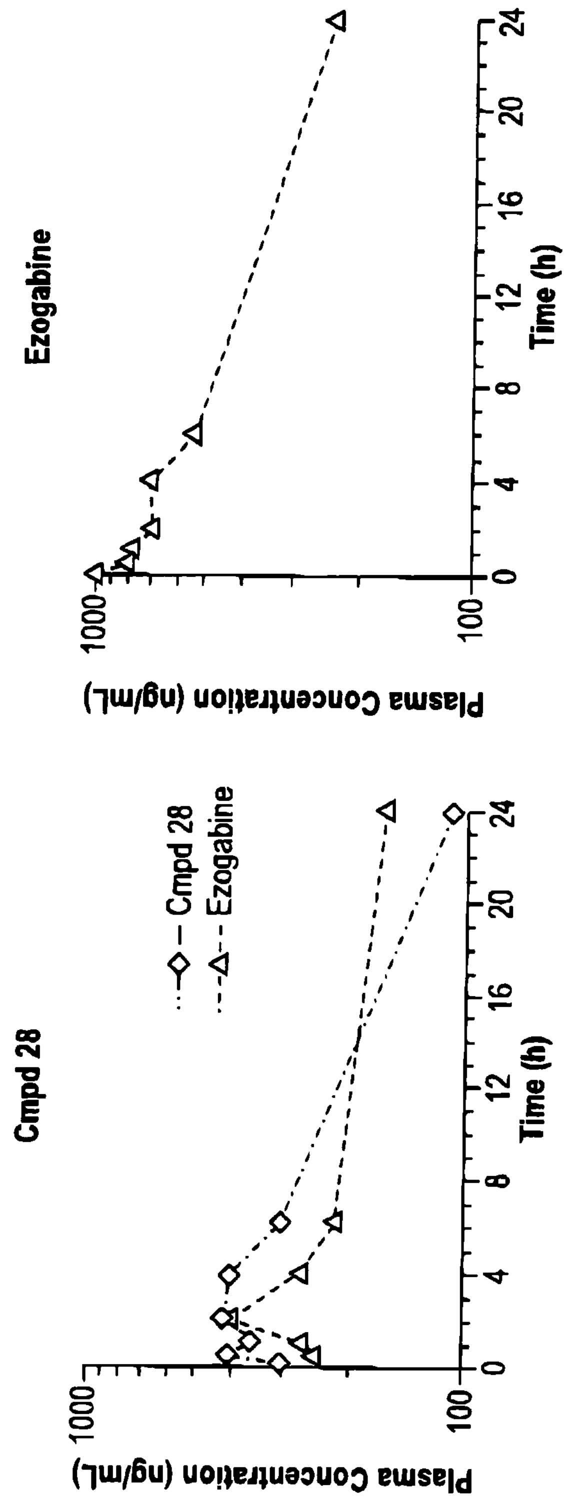
Figure 23:
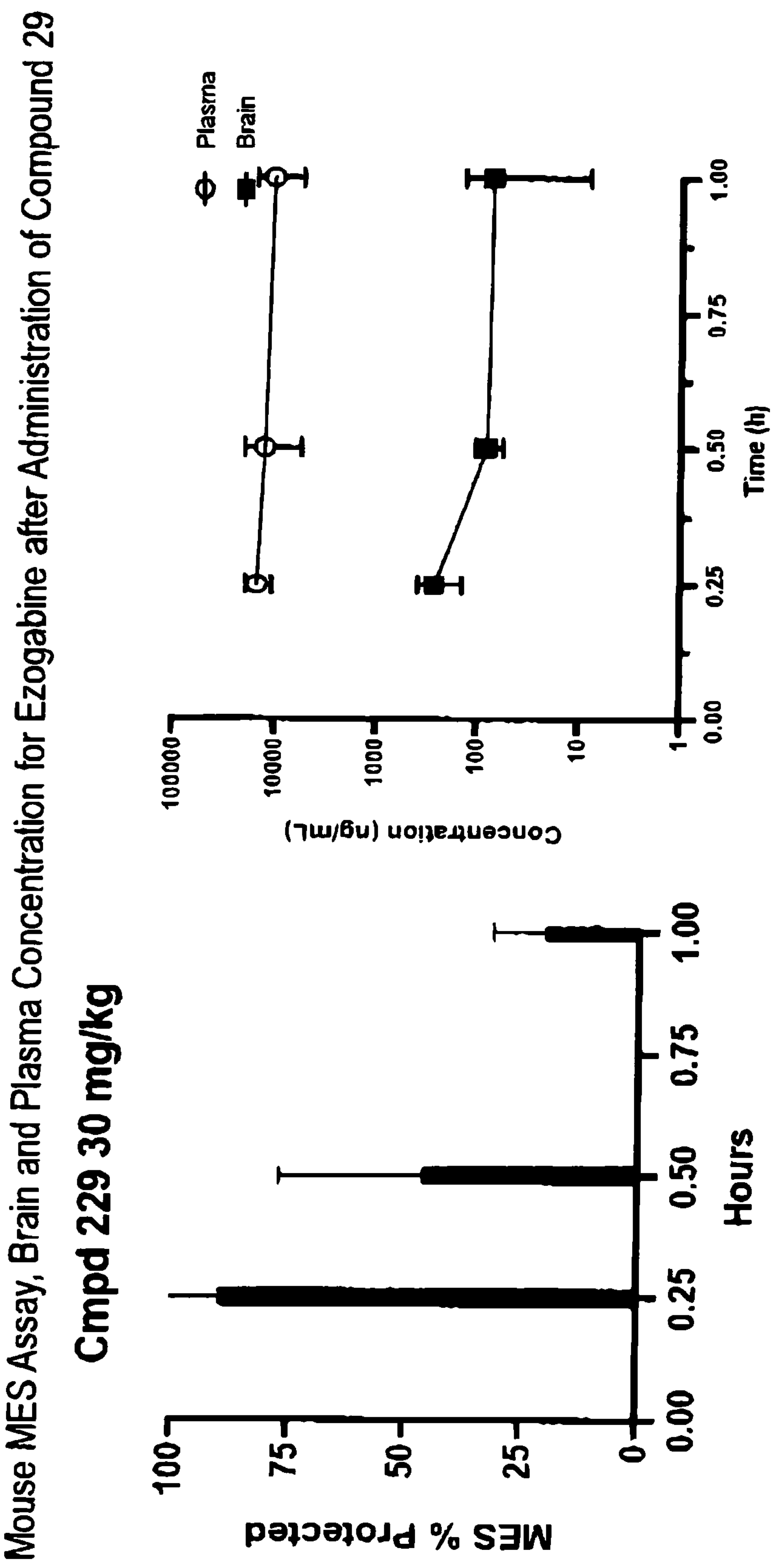

FIG. 21 is a graphical description of the concentration (ng/mL) of Compound 28, Ezogabine and Pregabalin at 0.5 h post 24 mg/kg dose FIG. 22 is a graphical description of the concentration (ng/mL) of Compound 28 and Ezogabine over 24 hours FIG. 23 is a graphical illustration of Mouse MES Assay, Brain and Plasma Concentration for Ezogabine after Administration of Compound 29.

DETAILED DESCRIPTION OF THE DISCLOSURE

As used herein, "alkyl" refers to monovalent saturated aliphatic hydrocarbon groups having from 1 to 20 carbon atoms, preferably 1-8 carbon atoms, preferably 1-6 carbon atoms. The hydrocarbon chain may be either straight-chained or branched. Illustrative alkyl groups include methyl, ethyl, n-propyl, iso-propyl, n-butyl, iso-butyl, sec-butyl and tert-butyl. Similarly, an "alkenyl" group refers to an alkyl group having one or more double bonds present in the chain, and an "alkynyl" group refers to an alkyl group having one or more triple bonds present in the chain.

As used herein "halogen" or "halo" refers to a halogen. In some embodiments, the halogen is preferably Br, Cl, or F.

As used herein, "haloalkyl" refers to monovalent saturated aliphatic hydrocarbon groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain, and a "haloalkynyl" group refers to a haloalkyl group having one or more triple bonds present in the chain. Moreover, an "alkylene" linker group refers to a divalent alkyl group, namely $(CH_2)_x$, where x is 1 to 20, preferably 1 to 8, preferably 1 to 6, and more preferably 1 to 3.

The term "haloalkyloxy" refers to O-haloalkyl.

As used herein, "alkoxy" refers to an O-alkyl group having the specified number of carbon atoms.

An "alkylene," group is an alkyl group, as defined hereinabove, that is positioned between and serves to connect two other chemical groups. Exemplary alkylene groups include, without limitation, methylene, ethylene, propylene, and butylene.

The term "heteroalkyl" refers to an alkyl group, as defined hereinabove, wherein one or more carbon atoms in the chain are replaced by a heteroatom selected from the group consisting of O, S, and N, such as NH or NR', where R' is a general indicator for a non-hydrogen group.

As used herein, "hydroxyalkyl" refers to an alkyl group as herein defined substituted with one or more —OH group. Similarly, a "hydroxyalkenyl" group refers to a hydroxyalkyl group having one or more double bonds present in the chain, and a "hydroxyalkynyl" group refers to a hydroxyalkyl group having one or more triple bonds present in the chain. Likewise, a "dihydroxyalkyl" group provides two —OH substituents.

The term "alkylaminyl" refers to $NR^x$-alkyl, wherein $R^x$ is hydrogen.

The term "dialkylaminyl" refers to $N(R^y)_2$, wherein each $R^y$ is independently $C_1$-$C_3$ alkyl.

The term "alkylaminylalkyl" refers to alkyl-$NR^x$-alkyl, wherein $R^x$ is hydrogen.

The term "dialkylaminylalkyl" refers to alkyl-$N(R^y)_2$, wherein each $R^y$ is independently $C_1$-$C_4$ alkyl, wherein the alkyl of the alkyl-$N(R^y)_2$ is an alkyl group as defined hereinabove and may be optionally substituted with hydroxy or hydroxyalkyl.

As used herein, "aryl" refers to a substituted or unsubstituted carbocyclic aromatic ring system, either pendent or fused, such as phenyl, naphthyl, anthracenyl, phenanthryl, tetrahydronaphthyl, indane, or biphenyl. A preferred aryl group is phenyl.

An "aralkyl" or "arylalkyl" group comprises an aryl group covalently linked to an alkyl group as defined herein above, either of which may independently be optionally substituted or unsubstituted. An example of an aralkyl group is $(C_1$-$C_6)$ alkyl$(C_6$-$C_{10})$aryl, including, without limitation, benzyl, phenethyl, and naphthylmethyl. An example of a substituted aralkyl is wherein the alkyl group is substituted with hydroxyalkyl.

As used herein, "cycloalkyl" refers to an unsaturated or partially saturated hydrocarbon ring, containing from 3 to 15 ring atoms. Illustrative cycloalkyl groups include cyclopropyl, cyclobutyl, cyclopentyl, cyclohexyl, as well as partially saturated versions thereof, such as cyclohexenyl, and cyclohexadienyl. Moreover, bridged rings, such as adamantane, are included within the definition of "cycloalkyl."

As used herein, the term "heterocyclyl" refers to an unsaturated or partially saturated hydrocarbon ring, containing from 3 to 15 ring atoms, wherein one or more carbon atom is replaced with a heteroatom selected from O, N, or S, where each N, S, or Si may be oxidized, and where each N may be quarternized. A heterocyclyl group may be attached to the remainder of the molecule through a heteroatom. Heterocyclyl does not include heteroaryl.

The term "heterocyclylalkyl" refers to a heterocyclyl group as defined herein covalently linked to an alkyl group as defined hereinabove wherein the radical is on the alkyl group, wherein the alkyl group of the heterocyclylalkyl may be optionally substituted with hydroxy or hydroxyalkyl.

As used herein, the term "heteroaryl" or "heteroaromatic" refers to aromatic ring groups having 5 to 14 ring atoms selected from carbon and at least one (typically 1-4, more typically 1 or 2) heteroatom (e.g., oxygen, nitrogen, sulfur, or silicon). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteroaryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The terms "arylalkyl," "heteroarylalkyl," and "heterocyclylalkyl" refers to those radicals in which an aryl, heteroaryl, or heterocyclyl group is linked through an alkyl group. Examples includes benzyl, phenethyl, pyridylmethyl, and the like. The terms also include alkyl linking groups in which a carbon atom, for example, a methylene group, has been replaced by, for example, an oxygen atom. Examples include phenoxymethyl, pyrid-2-yloxymethyl, 3-(naphth-1-yloxy)propyl, and the like. Similarly, the term "benzyl" as used herein is a radical in which a phenyl group is attached to a $CH_2$ group, thus, a $CH_2Ph$ group. Benzyl groups may be substituted or unsubstituted. The term substituted benzyl refers to radicals in which the phenyl group or $CH_2$ contains one or more substituents. In one embodiment, the phenyl group may have 1 to 5 substituents, or in another embodiment 2 to 3 substituents.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein "optionally substituted" refers to a substitution of a hydrogen atom, which would otherwise be present for the substituent. When discussing ring systems, the optional substitution is typically with 1, 2, or 3 substituents replacing the normally-present hydrogen. When referencing straight and branched moieties, however, the number of substitutions may be more, occurring wherever hydrogen is present. The substitutions may be the same or different.

Illustrative substituents, which with multiple substituents can be the same or different, include halogen, haloalkyl, R', OR', OH, SH, SR', $NO_2$, CN, C(O)R', C(O)(alkyl substituted with one or more of halogen, haloalkyl, $NH_2$, OH, SH, CN, and $NO_2$), C(O)OR', OC(O)R', $CON(R')_2$, $OC(O)N(R')_2$, $NH_2$, NHR', $N(R')_2$, NHCOR', NHCOH, $NHCONH_2$, NHCONHR', $NHCON(R')_2$, NRCOR', NRCOH, $NHCO_2H$, $NHCO_2R'$, $NHC(S)NH_2$, NHC(S)NHR', $NHC(S)N(R')_2$, $CO_2R'$, $CO_2H$, CHO, $CONH_2$, CONHR', $CON(R')_2$, $S(O)_2H$, $S(O)_2R'$, $SO_2NH_2$, S(O)H, S(O)R', $SO_2NHR'$, $SO_2N(R')_2$, $NHS(O)_2H$, $NR'S(O)_2H$, $NHS(O)_2R'$, $NR'S(O)_2R'$, $Si(R')_3$, where each of the preceding may be linked through a divalent alkylene linker, $(CH_2)_x$, where x is 1, 2, or 3. In embodiments where a saturated carbon atom is optionally substituted with one or more substituent groups, the substituents may be the same or different and also include =O, =S, =NNHR', $=NNH_2$, $=NN(R')_2$, =N—OR', =N—OH, =NNHCOR', =NNHCOH, $=NNHCO_2R'$, $=NNHCO_2H$, $=NNHSO_2R'$, $=NNHSO_2H$, =N—CN, =NH, or =NR'. For each of the preceding, each may be linked through an alkylene linker, $(CH_2)_x$, where x is 1, 2, or 3, Each occurrence of R' is the same or different and represents hydrogen, alkyl, alkenyl, alkynyl, cycloalkyl, aryl, heterocyclyl, or heteroaryl, or when two R' are each attached to a nitrogen atom, they may form a saturated or unsaturated heterocyclic ring containing from 4 to 6 ring atoms.

As used herein, "an effective amount" of a compound is an amount that is sufficient to negatively modulate or inhibit the activity of the target. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of the target. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of the inhibitor detailed herein or a pharmaceutically acceptable salt thereof, or the length of treatment time described herein) means that the parameter may vary by as much as 25%, 20%, 15%, 10%, or 5% below or above the stated numerical value for that parameter. For example, a dose of about 5 mg/kg may vary between 3.75 mg/kg and 6.25 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

As used herein, a salt refers to any salt of a compound disclosed herein which retains its biological properties and which is not toxic or otherwise undesirable for pharmaceutical use.

Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that may be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that may be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

The base may be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that may be used in accordance with the present disclosure include choline hydroxide, trimethylethylammonium hydroxide, tetramethylammonium hydroxide, and is preferably choline hydroxide. An alkylamine base may be substituted or unsubstituted. Non-limiting examples of unsubstituted alkylamine bases that may be used in accordance with the present disclosure include methylamine, ethylamine, diethylamine, and triethylamine. A substituted alkylamine base may be substituted with one or more hydroxyl groups, and preferably one to three hydroxyl groups. Non-limiting examples of substituted alkylamine bases that may be used in accordance with the present disclosure include 2-(diethylamino)ethanol, N,N-dimethylethanolamine (deanol), tromethamine, ethanolamine, and diolamine.

In certain cases, the depicted substituents may contribute to optical isomers and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. A molecule with at least one stereocenter may be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or may be characterized by the manner in which the molecule rotates the plane of polarized light and is designated dextrorotatory or levorotatory (namely, as (+)- or (−)-isomers, respectively). A chiral compound may exist as either an individual enantiomer or as a mixture thereof. A mixture containing equal proportions of enantiomers is called a "racemic mixture".

In certain embodiments, the compounds disclosed herein may possess one or more asymmetric centers, and such compounds may therefore be produced as a racemic mixture, an enantiomerically enriched mixture, or as an individual enantiomer. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skilled in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" may be used interchangeably herein. In one embodiment, the subject is a human. In one embodiment, the subject is a companion animal such as a dog or cat. In a further embodiment, the subject is an animal such as a sheep, cow, horse, goat, fish, pig, or domestic fowl (e.g., chicken, turkey, duck, or goose). In another embodiment, the subject is a primate such as a monkey such as a cynomolgus monkey or a chimpanzee.

I. Modulators of Voltage-Dependent Potassium Channels

Compound 1 is a potassium ion channel modulator

Compound 1

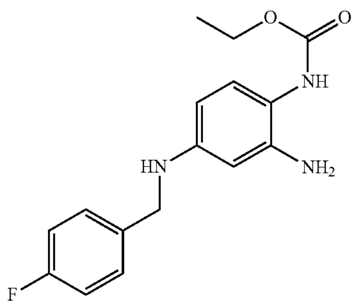

The present disclosure provides novel prodrugs which are metabolized in vivo to release potassium ion channel modulators, such as the one presented as compound 1; particularly novel prodrugs which release compounds effective at modulating KCNQ, are according to Formulae of the present disclosure.

Embodiments of the present disclosure include:

Formula I

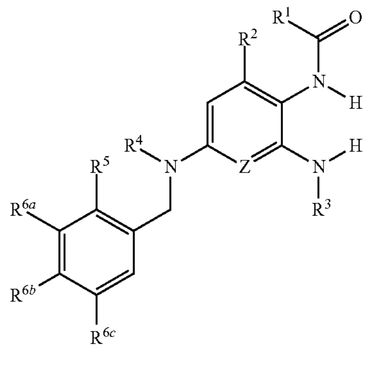

-continued

Formula II

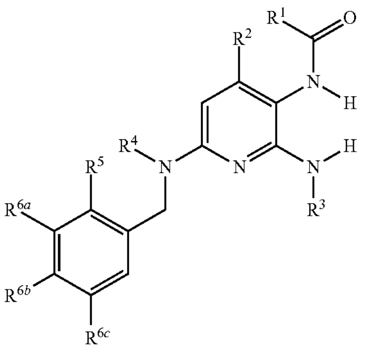

$R^1$ is $C_{1-6}$ alkyl, $C_{1-6}$ alkoxy, $C_{1-6}$ alkyl-$C_{3-6}$ cycloalkyl;
$R^2$ is H, $C_{1-3}$ alkyl, $C_{1-3}$ alkoxy, halogen, $C_{1-3}$ haloalkoxy;
$R^3$ is "Pro," a prodrug moiety, as herein described;
each of $R^4$ and $R^5$ independently is H, or
$R^4$ and $R^5$, taken together with the atoms to which they are bound, form a 5 to 6 membered ring, optionally containing one or more degree of unsaturation; and
each of $R^{6a}$, $R^{6b}$, and $R^{6c}$ independently is H or halogen, where at least one of $R^{6a}$, $R^{6b}$, and $R^{6c}$ is H,
or a pharmaceutically acceptable salt thereof,
wherein $C_{1-3}$ haloalkoxy is $—OCF_3$, $—OCF_2H$, $—OCFH_2$, $—OC_2F_5$, $—OC_2F_4H$, $—OC_2F_3H_2$, $—OC_2F_2H_3$, $—OC_2FH_4$, $—OC_3F_7$, $—OC_3F_6H$, $—OC_3F_5H_2$, $—OC_3F_4H_3$, $—OC_3F_3H_4$, $—OC_3F_2H_5$, or $—OC_3FH_6$;

In one embodiment, the variable "Pro" is selected from the group consisting of $C(O)R^{10}$ wherein $R^{10}$ is
an alkylamine-containing residue such as from the alkylamine-containing portions of the naturally-occurring L-amino acids or D-amino acids or
glycine; or
the alkylamine-containing portions of theanine or gabapentin or pregabalin; or
wherein $R^{10}$ is selected from a hydrolysable prodrug moiety such as found in a group with the structure: $—C(O)OL^1OC(O)R^{11}$; and
wherein $R^{11}$ is $C_1$-$C_{10}$ alkyl, Bn, t-Bu, other $C_3$-$C_{10}$ secondary or tertiary alkyl groups, substituted or unsubstituted; or Ar; and
$L^1$ is $C_1$-$C_{10}$ branched or chain alkylene wherein the two oxygen atoms on $L^1$ are on the same carbon atom within $L^1$ (i.e., divalent alkyl forming a ketal- or acetal-like moiety).

One embodiment of the present disclosure includes a compound of Formula I:

Formula I

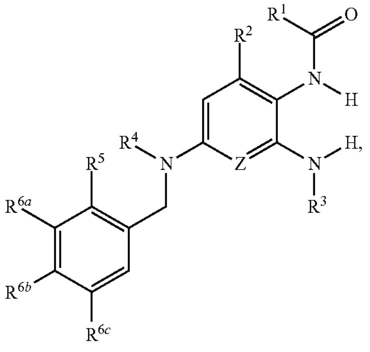

wherein
$R^1$ is $C_{1-6}$ alkyl, $C_{1-6}$ alkoxy, $C_{1-6}$ alkyl-$C_{3-6}$ cycloalkyl;
$R^2$ is H, $C_{1-3}$ alkyl, $C_{1-3}$ alkoxy, halogen, $C_{1-3}$ haloalkoxy;
Z is N or CH;
$R^3$ is "Pro" wherein "Pro" is selected from the group consisting of $C(O)R^{10}$;
$R^{10}$ is selected from the group consisting of:
a) an alkylamine-containing residue such as from the alkylamine-containing portions of the naturally-occurring L-amino acids or D-amino acids or
b) a glycine residue;
c) a theanine residue;
d) a gabapentin residue;
e) a pregabalin residue; and
f) selected from a hydrolysable prodrug moiety of the structure $C(O)OL^1OC(O)R^{11}$, where
$R^{11}$ is unsubstituted or substituted $C_1$-$C_{10}$ alkyl, aryl, $C_1$-$C_{10}$ aralkyl;
$L^1$ is $C_1$-$C_{10}$ alkylene, wherein the two oxygen atoms depicted as attached to $L^1$ are on the same carbon atom within $L^1$ (i.e., divalent alkyl forming a ketal- or acetal-like moiety)

Examples of $R^{10}$ as an alkylamine from naturally-occurring amino acids are:
$(CH_2)—NH_2$ from glycine,
$CH(CH_3)—NH_2$ from alanine,
$CH(CH(CH_3)_2)—NH_2$ from valine,
$CH(CH_2CH(CH_3)_2)—NH_2$ from leucine,
$CH(CH(CH_3)CH_2CH_3)—NH_2$ from isoleucine,
$CH(CH_2Ph)$-$NH_2$ from phenylalanine,
cyclo-$CHCH_2CH_2CH_2NH—$ from proline,
$CH(CH_2OH)—NH_2$ from serine,
$CH(CH(OH)CH_3)—NH_2$ from threonine,
$CH(CH_2(PhOH))—NH_2$ from tyrosine,
$CH(CH_2SH)—NH_2$ from cysteine,
$CH(CH_2CH_2SCH_3)—NH_2$ from methionine,
$CH(CH_2CH_2CH_2CH_2NH_2)—NH_2$ from lysine,
$CH(CH_2CH_2CH_2NHC(NH)NH_2)—NH_2$ from arginine,
$CH(CH_2(C_3N_2H_3))NH_2$ from histidine,
$CH(CH_2$-indole-3-yl$)NH_2$ from tryptophan,
$CH(CH_2CO_2H)—NH_2$ from aspartic acid,
$CH(CH_2CH_2CO_2H)—NH_2$ from glutamic acid,
$CH(CH_2CONH_2)—NH_2$ from asparagine, and
$CH(CH_2CH_2CONH_2)—NH_2$ from glutamine; or
$CH(CH_2CH_2CONHCH_2CH_3)—NH_2$ from theanine or
$CH_2C(—CH_2CH_2CH_2CH_2CH_2—)CH_2NH_2$ from gabapentin, or
$CH_2CH(CH_2CH(CH_3)_2)CH_2NH_2$ from pregabalin;

The alkylamine moieties from D or S-isomers of the above amino acids are also examples of alkylamine moieties from amino acids contemplated in the disclosure;
Each of $R^4$ and $R^5$ independently is H, or
$R^4$ and $R^5$, taken together with the atoms to which they are bound, form a 5 to 6 membered ring, optionally containing one or more degree of unsaturation; and
each of $R^{6a}$, $R^{6b}$, and $R^{6c}$ independently is H or halogen, where at least one of $R^{6a}$, $R^{6b}$, and $R^{6c}$ is H,
or a pharmaceutically acceptable salt thereof.

In a further exemplary embodiment, the disclosure provides prodrugs according to Formula III and more specifically Formula III-A and specifically Compound 3:

Formula III

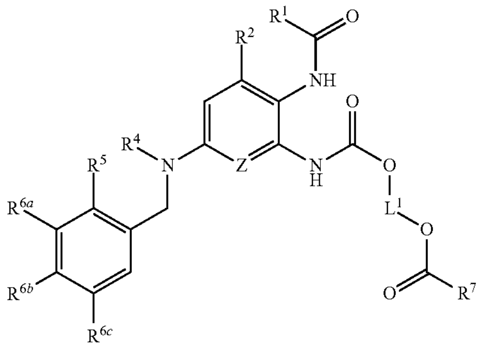

$R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is N or CH;

$R^3$ is Pro, a prodrug moiety as herein defined;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, $R^7$ is $C_{1-6}$ alkyl (as noted herein, includes branched or straight chain), phenyl, or $C_{1-2}$ alkyl-phenyl, or a pharmaceutically acceptable salt thereof.

One embodiment of the present disclosure includes

Formula III-A

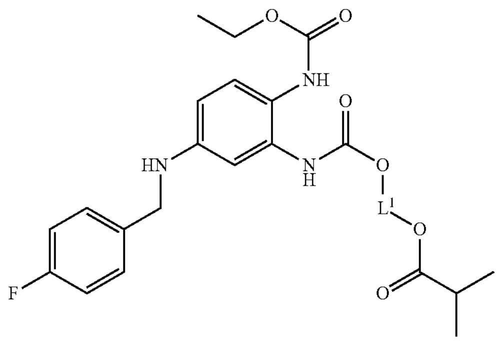

$L^1$ is $C_1$-$C_{10}$ branched or chain alkylene wherein the two oxygen atoms on $L^1$ are on the same carbon atom within $L^1$ (i.e., divalent alkyl forming a ketal- or acetal-like moiety)).

One embodiment of the present disclosure includes

Compound 3

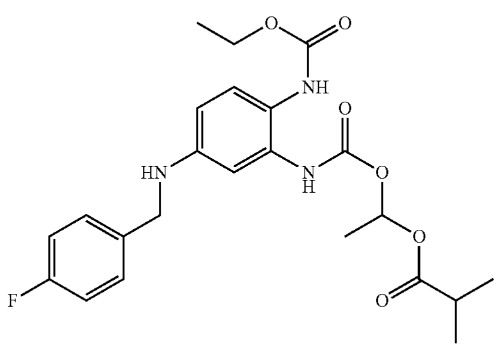

In a further exemplary embodiment, the disclosure provides the prodrug compounds having the Formula IV and more specifically Formula IV-A and specifically Compound 4:

Formula IV

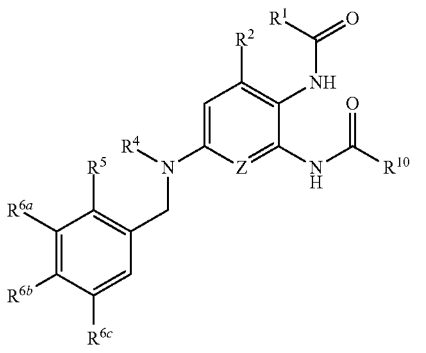

$R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is N or CH;

$R^3$ is "Pro," a prodrug moiety, as herein described;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, $R^{10}$ is as an alkylamine from naturally-occurring amino acids are: $-(CH_2)-NH_2$ from glycine, $-CH(CH_3)-NH_2$ from alanine, $-CH(CH(CH_3)_2)-NH_2$ from valine, $-CH(CH_2CH(CH_3)_2)-NH_2$ from leucine, $-CH(CH(CH_3)CH_2CH_3)-NH_2$ from isoleucine, $-CH(CH_2Ph)$-$NH_2$ from phenylalanine, cyclo-$CHCH_2CH_2CH_2NH-$ from proline, $-CH(CH_2OH)-NH_2$ from serine, $-CH(CH(OH)CH_3)-NH_2$ from threonine, $-CH(CH_2(PhOH))-NH_2$ from tyrosine, $-CH(CH_2SH)-NH_2$ from cysteine, $-CH(CH_2CH_2SCH_3)-NH_2$ from methionine, $-CH(CH_2CH_2CH_2CH_2NH_2)-NH_2$ from lysine, $-CH(CH_2CH_2CH_2NHC(NH)NH_2)-NH_2$ from arginine, $-CH(CH_2(C_3N_2H_3))NH_2$ from histidine, $CH(CH_2$-indole-3-yl)$NH_2$ from tryptophan, $-CH(CH_2CO_2H)-NH_2$ from aspartic acid, $-CH(CH_2CH_2CO_2H)-NH_2$ from glutamic acid, $-CH(CH_2CONH_2)-NH_2$ from asparagine, and —$CH(CH_2CH_2CONH_2)$—$NH_2$ from glutamine; or —$CH(CH_2CH_2CONHCH_2CH_3)$—$NH_2$ from theanine or —$CH_2C$(—$CH_2CH_2CH_2CH_2CH_2$—)$CH_2NH_2$ from gabapentin, or —$CH_2CH(CH_2CH(CH_3)_2)CH_2NH_2$ from pregabalin; the alkylamine moieties from D-isomers of the above amino acids are also examples of alkylamine moieties from amino acids contemplated in the disclosure; or a pharmaceutically acceptable salt thereof.

One embodiment of the present disclosure includes:

Formula IV-A

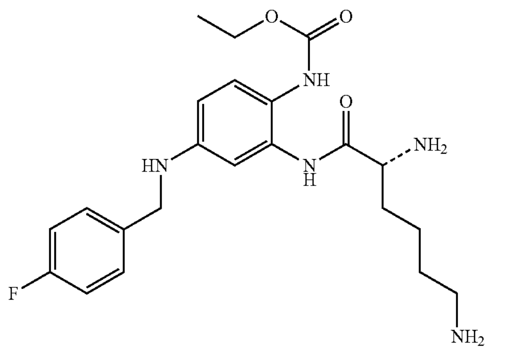

where the depicted dashed bond is either enantiomer.

One embodiment of the present disclosure includes a compound of a pharmaceutically acceptable salt thereof:

Compound 4

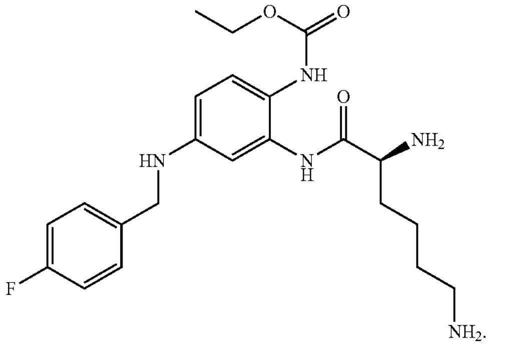

One embodiment of the present disclosure includes a compound or a pharmaceutically acceptable salt thereof:

Compound 6

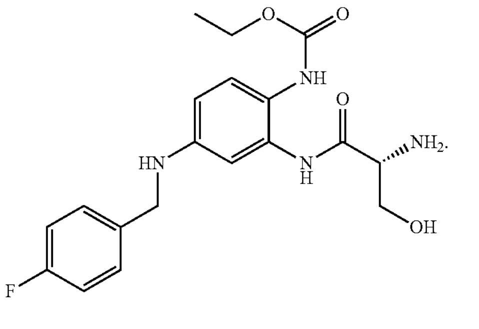

One embodiment of the present disclosure includes a compound or a pharmaceutically acceptable salt thereof:

Compound 29

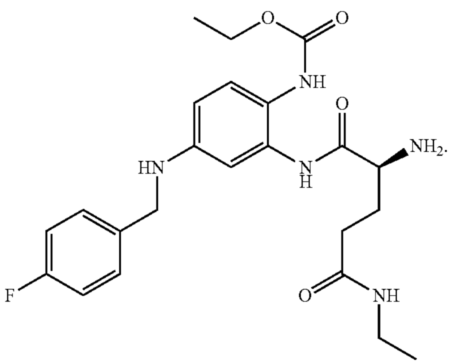

One embodiment of the present disclosure includes a compound wherein $R^{10}$ is $CH_2C$(—$CH_2CH_2CH_2CH_2CH_2$—)$CH_2NH_2$ from gabapentin, or $CH_2CH(CH_2CH(CH_3)_2)CH_2NH_2$ from pregabalin.

One embodiment of the present disclosure includes a compound or a pharmaceutically acceptable salt thereof:

Compound 28

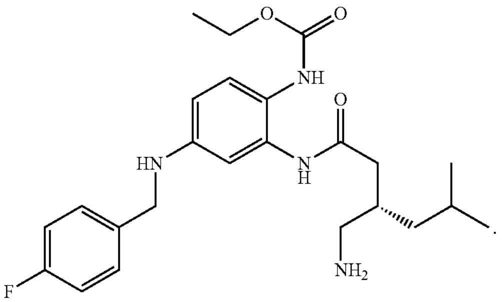

II. Assays for Modulators of Kv7 Channels

Kv7 channels were previously identified as KCNQ channels and are one in the same. Assays for determining the ability of active molecules to maintain Kv7 channels in higher probability within the open position, i.e. positive allosteric modulators, are generally known in the art. One of skill in the art is able to determine an appropriate assay for investigating the activity of a selected compound of the disclosure towards a particular ion channel. For simplicity, portions of the following discussion focus on Kv7.2 (KCNQ2) as a representative example, however, the discussion is equally applicable to other Kv7 subtype potassium ion channels.

KCNQ (Kv7) monomers as well as KCNQ alleles and polymorphic variants are subunits of potassium channels. The activity of a potassium channel comprising KCNQ subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising KCNQ. Such modulators of a potassium channel are useful for treating various disorders involving potassium channels, including but not limited to, for example, central and peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases, and can also be used as neuroprotective agents (e.g., to prevent stroke and the like). Such modulators are also useful for investigation of the channel diversity provided by KCNQ and the regulation/modulation of potassium channel activity provided by KCNQ. Prodrugs which are metabolized by amidases, esterases and other metabolic or hydrolytic mechanisms in a mammal, or cells are able to produce active modulators of channels comprising KCNQ. Some prodrugs, themselves, may also have weak activity as KCNQ channel modulators. But it is likely, any activity may be due to degradation in the test system to the active drug and in most of these cases that the metabolized prodrug produces a more active KCNQ modulator than the prodrug itself.

Modulators of the potassium channels are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Activation of channels comprising KCNQ2 is achieved when the potassium channel activity value relative to the control is 130%, more preferably 150%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and increasing the number or expression of channels. It is important in these experiments to have materials present in each of the experiments which are known to metabolize the prodrugs of the disclosure into the compounds active at the receptor sites of interest. Or one may perform these experiments using the actual drug compound itself and assume that the metabolized prodrug, once in the body of a mammal, will have a similar activity at the desired ion channel site.

The activity of the metabolites of these prodrug compounds of the disclosure can also be represented by $EC_{50}$. Preferred compounds of the disclosure release active molecules upon hydrolysis or metabolism which have an $EC_{50}$ in a potassium ion channel assay of from about 0.1 nM to about 1 mM, preferably from about 1 nM to about 10 μM, and more preferably from about 10 nM to about 2 μM.

Changes in ion flux may be assessed by determining changes in polarization (i.e., electrical potential) of the cell or membrane expressing an exemplary potassium channel such as KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., New Engl. J. Med. 336: 1575-1595 (1997)). Whole cell currents are conveniently determined using the standard methodology (see, e.g., Hamil et al., Pflugers. Archiv. 391: 85 (1981). Other known assays include: radiolabeled rubidium flux assays and fluorescence assays using voltage-sensitive dyes (see, e.g., Vestergarrd-Bogind et al., J. Membrane Biol. 88: 67-75 (1988); Daniel et al., J. Pharmacol. Meth. 25: 185-193 (1991); Holevinsky et al., J. Membrane Biology 137: 59-70 (1994)). Assays for compounds capable of inhibiting or increasing potassium flux through the channel proteins comprising KCNQ2 or heteromultimers of KCNQ subunits can be performed by application of the compounds to a bath solution in contact with and comprising cells having a channel of the present disclosure (see, e.g., Blatz et al., Nature 323: 718-720 (1986); Park, J. Physiol. 481: 555-570 (1994)). Generally, the compounds to be tested are present in the range from about 1 pM to about 1 mM, preferably from about 10 pM to about 100 μM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this disclosure.

III. Pharmaceutical Compositions of Potassium Channel Modulators

In another aspect, the present disclosure provides pharmaceutical compositions comprising a pharmaceutically acceptable excipient and a compound of Formula I provided above.

Formulation of the Compounds (Compositions)

The compounds of the present disclosure can be prepared and administered in a wide variety of oral, parenteral and topical dosage forms. Thus, the compounds of the present disclosure can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present disclosure can be administered transdermally, ocularly, intracochlearly or intrarectally. Accordingly, the present disclosure also provides pharmaceutical compositions comprising a pharmaceutically acceptable carrier or excipient and either a compound of Formula I, or a pharmaceutically acceptable salt thereof.

For preparing pharmaceutical compositions from the compounds of the present disclosure, pharmaceutically acceptable carriers can be either solid or liquid. Solid form preparations include powders, tablets, pills, capsules, cachets, suppositories, and dispersible granules. The solid form can be either an immediate release, sustained release, modified release or delayed release. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 85% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In one method for preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, pill, cachet, sachet or lozenge itself, or it can be the appropriate number of any of these in packaged form.

The quantity of active component in a unit dose preparation may be varied or adjusted from 0.1 mg to 10000 mg, more typically 1.0 mg to 5000 mg, most typically 20 mg to 1000 mg, according to the particular application and the potency of the active component. The composition can, if desired, also contain other compatible therapeutic agents.

IV. Effective Dosages

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat pain, epilepsy, depression, or anxiety, such compositions will contain an amount of active ingredient effective to achieve a clinically relevant degree of reduction in the condition being treated. Similarly, when the pharmaceutical composition is used to treat or prevent a central or peripheral nervous system disorder, e.g., Parkinson's disease a therapeutically effective amount will reduce one or more symptoms characteristic of the diseases (e.g., tremors) to below a predetermined pressure threshold. Determination of a therapeutically effective amount of a compound of the disclosure is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of modulating, e.g., activating or opening the KCNQ channel. In preferred embodiments, the KCNQ channel activity is altered by at least 5% at clinical effective free drug concentrations for certain diseases or treatments and at least 10% in other diseases or treatments. The percentage of alteration of the KCNQ channel in the patient with a prodrug of a Kv7 positive allosteric modulator can adjusted based on plasma drug concentration of the active, and the dosage can be adjusted upwards or downwards to achieve the desired therapeutic effect.

As is well known in the art, therapeutically effective amounts for use in humans can also be determined from animal models. For example, a dose for humans can be formulated to achieve a circulating concentration that has been found to be effective in animals. A particularly useful animal model for predicting anticonvulsant dosages is the maximal electroshock assay (Fischer R S, Brain Res. Rev. 14: 245-278 (1989)). The dosage in humans can be adjusted by monitoring KCNQ channel activation and adjusting the dosage upwards or downwards, as described above.

A therapeutically effective dose can also be determined from human data for compounds which are known to exhibit similar pharmacological activities, such as ezogabine (Rudnfeldt et al., Neuroscience Lett. 282: 73-76 (2000)).

Adjusting the dose to achieve maximal efficacy in humans based on the methods described above and other methods as are well-known in the art is well within the capabilities of the ordinarily skilled artisan.

By way of example, when a compound of the disclosure is used in the prophylaxis and/or treatment of an exemplary disease such as epilepsy and pain, a circulating concentration of administered compound of about 0.001 μM to 1 mM is considered to be effective, with about 0.01 μM to 100 μM being preferred.

Patient doses for oral administration of the compounds described herein, which is the preferred mode of administration for prophylaxis and for treatment of an exemplary disease such as epilepsy, typically range from about 1 mg/day to about 10,000 mg/day, more typically from about 10 mg/day to about 3,000 mg/day, and most typically from about 1 mg/day to about 1000 mg/day. Stated in terms of patient body weight, typical dosages range from about 0.01 to about 150 mg/kg/day, more typically from about 0.1 to about 50 mg/kg/day, and most typically from about 0.5 to about 25 mg/kg/day.

For other modes of administration, dosage amount and interval can be adjusted individually to provide plasma levels of the administered compound effective for the particular clinical indication being treated. For example, if acute epileptic seizures are the most dominant clinical manifestation, in one embodiment, a compound according to the disclosure can be administered in relatively high concentrations multiple times per day. Alternatively, if the patient exhibits only periodic epileptic seizures, migraines, or other acute onset clinical signs or symptoms from chronic or acute disease states on an infrequent, periodic or irregular basis, in one embodiment, it may be more desirable to administer a compound of the disclosure at minimal effective concentrations and to use a less frequent administration regimen. This will provide a therapeutic regimen that is commensurate with the severity of the individual's disease.

Utilizing the teachings provided herein, an effective prophylactic or therapeutic treatment regimen can be planned which does not cause substantial toxicity and yet is entirely effective to treat the clinical symptoms demonstrated by the particular patient.

This planning should involve the careful choice of active compound by considering factors such as compound potency, relative bioavailability, patient body weight, presence and severity of adverse side effects, preferred mode of administration and the toxicity profile of the selected agent. As examples, without limitation, an intranasal route of administration may be useful to treat migraine and an ocular route may be useful to treat one or more diseases of the eye. Thus, a particular route of administration may be selected based on the intended therapeutic indication of the compound of the present disclosure.

V. Compound Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p. 1, 1975. The exact formulation, route of administration and dosage can be chosen by the individual physician in view of the patient's condition and the particular method in which the compound is used.

VII. Methods for Treating Conditions Mediated by Voltage-Dependent Potassium Channels In still another aspect, the present disclosure provides a method for the treatment of a central or peripheral nervous system disorder or condition through modulation of a voltage-dependent potassium channel. In this method, a subject in need of such treatment is administered an effective amount of a compound having the formula provided above.

The compounds provided herein are useful prodrugs of potassium channel modulators and find therapeutic utility via modulation through improvements in pharmacokinetics, solubility, stability of molecules that are active on voltage-dependent potassium channels in the treatment of diseases or conditions. The potassium channels targets for the compounds of the disclosure are described herein as voltage-dependent potassium channels such as the KCNQ potassium channels. As noted above, these channels may include homomultimers and heteromultimers of KCNQ2, KCNQ3, KCNQ4, and KCNQ5. A heteromultimer of two proteins, e.g., KCNQ2 and KCNQ3 is referred to as, for example, KCNQ2/3, KCNQ3/5, etc. The conditions that can be treated with the compounds and compositions of the present disclosure may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety, and motor neuron diseases). The compounds and compositions of the present disclosure may also serve as neuroprotective agents (e.g., to prevent stroke, retinal degeneration, demyelinating diseases and the like). In a preferred embodiment, the condition or disorder to be treated is epilepsy or seizures, central or peripheral neuropathic pain, chronic pain, inflammatory pain. In another preferred embodiment, the condition or disorder is hearing loss or treatment of diseases associated with neuronal demyelination or neuronal hyperexcitability.

Thereafter, the dosage is increased by small increments until the optimum effect under circumstances is reached. For convenience, the total daily dosage may be divided and administered in portions during the day, if desired.

One embodiment of the present disclosure includes a method of treating, ameliorating, or preventing the progress of a disease or a disorder comprising seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorder, phobias, Pick's disease, psychosis, a bipolar disorder, Schizophrenia, (schizophrenia subtypes being the catatonic-subtype, the paranoid-subtype, the disorganized subtype or the residual subtype), Spinal cord damage, cardiomyopathia, cardiac arrhythmia, long QT Syndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, meta static tumor growth, a pneumoconiosis (such as aluminosis, anthracosis, asbestosis, chalicosis, ptilosis, Siderosis, Silicosis, tabacosis and by Sinosis), a chronic obstructive pulmonary disease (COPD), obesity, and disease associated hypertension.

One embodiment of the present disclosure includes a method of treating one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, and autism spectrum disorders. The following cited references may be incorporated by reference with regard to such teaching for the nexus of the mechanism to the applicable disease or disorder.

a. Seizures (L Greene, Epilepsia 2018; J Neurosci, Qiu. 2008).

Neurons from Kv7.2(S559A) knock-in mice showed normal basal M-currents. Knock-in mice displayed reduced M-current suppression when challenged by a muscarinic agonist, oxotremorine-M. Kv7.2(S559A) mice were resistant to chemoconvulsant-induced seizures with no mortality. Administration of XE991 transiently exacerbated seizures in knock-in mice equivalent to those of wildtype mice. After experiencing status epilepticus, Kv7.2(S559A) knock-in mice did not show seizure-induced cell death nor spontaneous recurring seizures.

Using M-channel blockers, we found that SST4 coupling to M-channels is critical to its inhibition of epileptiform activity. This is the first demonstration of an endogenous enhancer of IM that is important in controlling seizure activity. SST4 receptors could therefore be an important novel target for developing new antiepileptic and antiepileptogenic drugs.

b. Pain, Neuropathic Pain, Chronic Headache (J Pain, Li. 2019).

Paclitaxel-induced peripheral neuropathy and associated neuropathic pain are severe and resistant to intervention. The results of our study demonstrated that retigabine (a clinically available medicine) can be used to attenuate the development of paclitaxel-induced peripheral neuropathy.

c. Central Pain, Pain Related to Diabetic Neuropathy, Postherpetic Neuralgia and to Peripheral Nerve Injury, (Brown Br J Pharmacology, 2009; Epilepsia, Trenite. 2013).

Several drugs including flupirtine and retigabine enhance neural Kv7/M-channel activity, principally through a hyperpolarizing shift in their voltage gating. In consequence they reduce neural excitability and can inhibit nociceptive stimulation and transmission. Flupirtine is in use as a central analgesic; retigabine is under clinical trial as a broad-spectrum anticonvulsant and is an effective analgesic in animal models of chronic inflammatory and neuropathic pain ICA-105665 reduced the SPR in patients at single doses of 100 (one of four), 400 (two of four), and 500 mg (four of six). This is the first assessment of the effects of activation of Kv7 potassium channels in the photosensitivity proof of concept model. The reduction of SPR in this patient population provides evidence of central nervous system (CNS) penetration by ICA-105665, and preliminary evidence that engagement with neuronal Kv7 potassium channels has antiseizure effects.

d. Alzheimer's Disease, (Czuzcwar, Pharmacological Reports 2010).

The most prominent adverse effects due to retigabine combined with the existing antiepileptic treatment were dizziness, somnolence and fatigue. The preclinical data indicate that this antiepileptic drug may possibly be applied in patients with neuropathic pain and affective disorders. Initial clinical data suggest that retigabine may be also effective in Alzheimer's disease or stroke.

e. Anxiety, CNS Damage Caused by Neurodegenerative Illness or Diseases or Injury, Cognitive Deficits, Compulsive Behavior, Dementia, Depressions, Huntington's Disease, Dystonia, Mania, (Richter, Br J Pharmacology 2006; Aiba, Brain 2021; Boehm, Pain 2019; Maghera, Epilepsia 2020; De Jong, Physiological Reports 2018; Jakubowski, Epilepsy Behav 2013; Zizhen Wu, J Pharmacol Exp Ther 2020; J E Larsson, in Physiology 2020; Yadav, Saudi J Anaesth 2017; Garakani, Front Psychiatry 2020; Maljevic, J Physiol 2008; R. Brant, Gastroenterology 2017; Hui Sun, JCI Insight 2019; R Brant, Gastroenterology 2017; Ravi Misra, Gastroenterology 2017; Parreno, Front Physiol 2020; Blom, PLoS One. 2014) (Feng Neuroscience 2019) (E Redford, Physiol Biochem 2021) (J Gunthrope, Epilepsia 2012; Epilepsia, Villalba. 2018). Since Retigabine and Flupirtine are Well Tolerated in Humans, the Present Finding of Pronounced Antidystonic Efficacy in the Dtsz Mutant Suggests that Neuronal Kv7 Channel Activators are Interesting Candidates for the Treatment of Dystonia-Associated Dyskinesias and Probably of Other Types of Dystonias. The Established Analgesic Effects of Kv7 Channel Openers Might Contribute to Improvement of these Disorders which are Often Accompanied by Painful Muscle Spasms Retigabine was shown to delay spreading depolarization onset following submaximal OGD stimulation. Interestingly, Kv7.2 activators are neuroprotective in experimental ischaemia and brain trauma studies, and the anti-spreading depolarization properties of the activator may contribute to these neuroprotective effects.

Studies support the emerging roles of Kv7 channels in intrinsic and synaptic plasticity, and their contributions to cognition and behavior The voltage-gated potassium channels of the KV7 family (KV7.1-5) play important roles in controlling neuronal excitability and are therefore attractive targets for treatment of CNS disorders linked to hyperexcitability.

f. Cognitive Disorders, Memory Impairment, Memory Disorders, Memory Dysfunction, (Frontal Physiol, Baculis. 2020; Frontal Physoil, Vigil. 2020).

Considering that Kv7 channels are critical for development and inhibition of neonatal brain (Peters et al., 2005; Soh et al., 2014), the memory impairment in these genetic models could be attributed to abnormal hippocampal morphology and/or hyperexcitability (Peters et al., 2005; Milh et al., 2020). Kv7 channels also regulate multiple behaviors. Behavioral phenotyping of the global or conditional homozygous KCNQ2 knock-out mice has not been possible due to their early postnatal lethality or premature death, respectively (Watanabe et al., 2000; Soh et al., 2014).

However, heterozygous KCNQ2 knock-out mice are viable and display increased locomotor activity and exploratory behavior (Kim et al., 2020), consistent with behavioral hyperactivity induced by transgenic suppression of Kv7 currents (Peters et al., 2005) and amphetamine and XE991 (Sotty et al., 2009). These mice also show decreased sociability and increased repetitive and compulsive behavior (Kim et al., 2020), reminiscent of autism seen in some EE patients with dominant KCNQ2 mutations (Weckhuysen et al., 2012, 2013; Milh et al., 2013). International Kv7 symposium in Naples, Italy in 2019, show great translational promise. Animal research indicates M current to be a therapeutic target for multiple brain disorders, including those with no current treatments, such as TBI and psychostimulant addiction.

g. Schizophrenia, (Transl Psychiatry, Nielsen. 2017; Br J Pharmacol, Wang. 2020).

Genetic or pharmacological inhibition of neuronal Kv7 channels can alleviate PPI and cognitive deficits induced by NMDA antagonists, thus suggesting a therapeutic potential for such inhibition of Kv7 channels in the treatment of schizophrenia or cognitive deficit disorder h. Spinal Cord Damage (J Pharmacol, Wu. 2020).

Reducing the activity of neurons by opening KCNQ/Kv7 channels may protect spinal neurons and axons from degeneration after SCI, thereby promoting recovery of motor and sensory function. Repeated application of retigabine to open these channels at the acute stage promotes neurobehavioral recovery after SCI.

i. Cardiomyopathia, Cardiac Arrhythmia (Front Physiol, Iarsson. 2020; J Physoil, Maljevic. 2008; Lee, Microcirculation. 2015).

Because of their important role in physiology, dysfunctional KV7 channels are often linked to disorders characterized by abnormal potassium ion conductance, including cardiac arrhythmia, hearing impairment, epilepsy, pain, and hypertension Mouse Kv7 channels may contribute differently to regulating the functional properties of cerebral and coronary arteries. Such heterogeneity has important implications for developing novel therapeutics for cardiovascular dysfunction.

h. Long QT Syndrome, (J Physoil, Maljevic. 2008; Acta Pyhsoil. Skarsfeldt. 2020: Acta Physoil, Bahannon. 2019).

Polyunsaturated fatty acids with double bonds closer to the head group had higher apparent affinity for IKs channels and increased IKs current more; shifting the bonds further away from the head group reduced apparent binding affinity for and effects on the IKs current. Interestingly, we found that ω-6 and ω-9 PUFAs, with the first double bond closer to the head group, left-shifted the voltage dependence of activation the most. These results allow for informed design of new therapeutics targeting IKs channels in Long QT Syndrome KV7 channels present interesting targets for new therapeutic approaches to diseases caused by neuronal hyperexcitability, such as epilepsy, neuropathic pain, and migraine. The molecular mechanism of KV7 activation by retigabine, which is in phase Ill clinical testing to treat pharmacoresistant focal epilepsies, has been recently elucidated as a stabilization of the open conformation by binding to the pore region i. Bowel Disorder, an Inflammatory Disease, Ulcerative Colitis, Crohn's Disease, (J Neurosci, Linley. 2008).

Further experiments demonstrated that M current inhibition required concurrent rises in cytosolic Ca 2 concentration and depletion of membrane phosphatidylinositol 4,5-bisphosphate (PIP2). We propose that PLC- and Ca 2/PIP2-mediated inhibition of M current in sensory neurons may represent one of the general mechanisms underlying pain produced by inflammatory mediators, and may therefore open up a new therapeutic window for treatment of this major clinical problem j. Creutzfeid-Jacobs disease, (Acta Pharmacol Sin, Teng. 2016).

A modified QO58 compound (QO58-lysine) can specifically activate Kv7.2/7.3/M-channels. Oral or intraperitoneal administration of QO58-lysine, which has improved bioavailability and a half-life of approximately 3 h in plasma, can reverse inflammatory pain in rodent animal models.

k. Progressive Hearing Loss or Tinnitus (J Physiol, Maljevic. 2008; Br J Pharmacol, Leithner. 2014; J Neurosci, Kalappa. 2015).

Stabilizing the KCNQ4-mediated conductance in OHCs, chemical channel openers can protect against OHC degeneration and progression of hearing loss in DFNA2.

Behavioral studies demonstrated that SF0034 was a more potent and less toxic anticonvulsant than retigabine in rodents. Furthermore, SF0034 prevented the development of tinnitus in mice. We propose that SF0034 provides, not only a powerful tool for investigating ion channel properties, but, most importantly, it provides a clinical candidate for treating epilepsy and preventing tinnitus.

l. Diabetes, (Front Cardivasc Med, Fosmo. 2017).

Kv7 channel activity may contribute to the development of the cardiovascular risk factors such as hypertension, diabetes, and obesity. Questions and hypotheses regarding previous and future research have been raised. Alterations in the Kv7 channel may contribute to the development of cardiovascular disease (CVD). Pharmacological modification of Kv7 channels may represent a possible treatment for CVD in the future.

m. Chronic Obstructive Pulmonary Disease (COPD)(Front Physiol, Mondejar-Parreno. 2020).

The functional role of Kv7 channels may vary depending on the cell type. Several studies have demonstrated that the impairment of Kv7 channel has a strong impact on pulmonary physiology contributing to the pathophysiology of different respiratory diseases such as cystic fibrosis, asthma, chronic obstructive pulmonary disease, chronic coughing, lung cancer, and pulmonary hypertension. Kv7 channels are now recognized as playing relevant physiological roles in many tissues, which have encouraged the search for Kv7 channel modulators with potential therapeutic use in many diseases including those affecting the lung. Modulation of Kv7 channels has been proposed to provide beneficial effects in a number of lung conditions. Therefore, Kv7 channel openers/enhancers or drugs acting partly through these channels have been proposed as bronchodilators, expectorants, antitussives, chemotherapeutics and pulmonary vasodilators.

n. Movement Disorder Selected from Primary Dystonia (a Richter Br J Pharmacol 2006).

These data indicate that dysfunctions of neuronal Kv7 channels deserve attention in dyskinesias. Since retigabine and flupirtine are well tolerated in humans, the present finding of pronounced antidystonic efficacy in the dtsz mutant suggests that neuronal Kv7 channel activators are interesting candidates for the treatment of dystonia-associated dyskinesias and probably of other types of dystonias. The established analgesic effects of Kv7 channel openers might contribute to improvement of these disorders which are often accompanied by painful muscle spasms o. Autism, Autism Spectrum Disorders, Comprising Administering a Compound of the Present Disclosure. (Gilling, Front Genet. 2013; Guglielmi, Front Cell Neurosci. 2015).

One embodiment of the present disclosure includes a method of delivering a broad spectrum Kv7.2-7.5 active molecule to systemic circulation and releasing said active Kv channel opener in an effective concentration at therapeutic concentrations to treat one or more susceptible disease or disorder comprising administering a compound of the present disclosure. In one aspect, release of the active molecule is provided under one or more of: enhanced by increased absorption.

Since retigabine and flupirtine are well tolerated in humans, the present finding of pronounced antidystonic efficacy in the dtsz mutant suggests that neuronal Kv7 channel activators are interesting candidates for the treatment of dystonia-associated dyskinesias and probably of other types of dystonias Mutations in neuronal Kv7 (KCNQ) potassium channels can cause episodic neurological disorders. Paroxysmal dyskinesias with dystonia are a group of movement disorders which are regarded as ion channelopathies, but the role of Kv7 channels in the pathogenesis and as targets for the treatment have so far not been examined.

Our results suggest that dysfunction of the heteromeric KV7.3/5 channel is implicated in the pathogenesis of some forms of autism spectrum disorders, epilepsy, and possibly other psychiatric disorders and therefore, KCNQ3 and KCNQ5 are suggested as candidate genes for these disorders.

EXAMPLES

In the examples below, unless otherwise stated, temperatures are given in degrees Celsius (° C.). Operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1H$-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Unless otherwise specified, all solvents (HPLC grade) and reagents were purchased from suppliers and used without further purification. Analytical thin layer chromatography (TLC) was performed on Whatman Inc. 60 silica gel plates (0.25 mm thickness). Compounds were visualized under UV lamp (254 nM) or by developing with $KMnO_4$/KOH, ninhydrin or Hanessian's solution. Flash chromatography was done using silica gel from Selectro Scientific (particle size 32-63). $^1H$ NMR, $^{19}F$ NMR and $^{13}C$ NMR spectra were recorded on a Varian 300 machine at 300 MHz, 282 MHz and 75.7 MHz, respectively. Melting points were recorded on an Electrothermal IA9100 apparatus and were uncorrected.

The following examples are offered to illustrate, but not to limit the claimed disclosure. The general procedures of Examples 1 and 2 can be modified by those skilled in the art to employ for the syntheses of compounds comprised in Formula III by proper substitution of other starting materials for ezogabine, flupirtine and acylating agents in appropriate amounts.

One skilled in the art will further recognize that human clinical trials including first-in-human, dose ranging and efficacy trials, in healthy patients and/or those suffering from a given disorder, may be completed according to methods well known in the clinical and medical arts.

The present disclosure explicitly encompasses those compounds presented below, including salt forms thereof. The present disclosure also encompasses those compounds presented below, including stereoisomers thereof. A composition comprising a therapeutically acceptable amount of any of these compounds is also within the scope of the disclosure. The composition may further comprise a pharmaceutically acceptable excipient, diluent, carrier, or mixture thereof. Such a composition may be administered to a subject in need thereof to treat or control a disease or disorder mediated, in whole or in part, directly or indirectly, by one or more voltage-dependent potassium channels. The compositions may further comprise an additional active agent, as described herein.

The following examples provide a more detailed description of the process conditions for preparing compounds of the present disclosure. It is to be understood, however, that the disclosure, as fully described herein and as recited in the claims, is not intended to be limited by the details of the following schemes or modes of preparation.

Certain abbreviations may be used in describing the examples of the present disclosure. The abbreviations are believed to be used consistently within commonly accepted use of those skilled in the art.

The compounds of the present disclosure may be prepared from commercially available reagents using the synthetic methods and reaction schemes described herein, or using other reagents and conventional methods well known to those skilled in the art.

In the following schemes, general substituent groups are represented with assignments that may not align with the formulae of the present disclosure. The following schemes provide a key for such substituent groups that should be followed for the schemes and not applied to the formulae of the present disclosure.

Schemes

General Scheme 1

Prodrug Synthesis from a Kv7-Active Drug Molecule

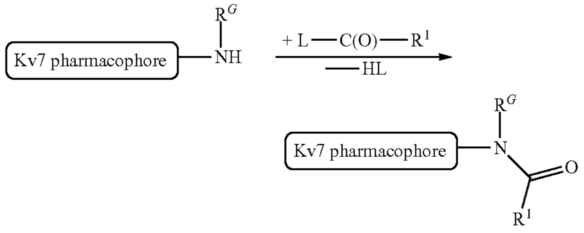

In General Scheme 1, the Kv7 pharmacophore is a drug moiety active at Kv7 potassium ion channels. The reagent L-C(O)—$R^1$, represents an activated carbonyl reagent or intermediate and L is a leaving group. $R^G$ represents H or a variety of substituent groups and $R^1$ is as used herein. The resulting product is a hydrolyzable prodrug that forms a Kv7-active drug upon hydrolysis.

Example 1

General Procedure for Preparation of Acetal/Ketal Diester Prodrugs of Ezogabine:

In a 500 mL round bottom flask equipped with a magnetic stirbar is placed 200 mL of dichloromethane at room temperature. Stirring is started and the following materials are added in order: Ezogabine (10.0 g, 33.00 mmol; 1.0 eq; 303.33 g/mol; [CAS #150812-12-7]), triethylamine (6.68 g; 66.00 mmol; 2.0 eq; 101.19 g/mol), the desired 1-(((4-Nitrophenoxy)carbonyl)oxy)alkyl carboxylate (34.62 mmol; 1.05 eq; and HOBt (0.446 g; 3.30 mmol; 0.1 eq; 135.12 g/mol). The flask is flushed with nitrogen gas and sealed with a septum. A nitrogen atmosphere is maintained using a needle attached to a nitrogen line at ~1 atm $N_2$ and the reaction progress is monitored by TLC. When no ezogabine remains by TLC, the reaction is worked up by adding 100 mL of water and stirring for 10 minutes under nitrogen. The contents of the flask are transferred to a separatory funnel and the layers are separated. The organic layer is washed two times with 0.1M sodium hydroxide solution and is dried over sodium sulfate. The volatiles are removed under vacuum and the residue is purified by column chromatography or recrystallisation to give the desired ezogabine-derived prodrug.

Example 2

General Procedure for Preparation of Acetal/Ketal Diester Prodrugs of Flupirtine:

In a 500 mL round bottom flask equipped with a magnetic stirbar is placed 200 mL of dichloromethane at room temperature. Stirring is started and the following materials are added in order: Flupirtine (10.0 g, 33.00 mmol; 1.0 eq; 303.33 g/mol; [CAS #56995-20-1]), triethylamine (6.68 g; 66.00 mmol; 2.0 eq; 101.19 g/mol), the desired 1-(((4-Nitrophenoxy)carbonyl)oxy)alkyl carboxylate (34.62 mmol; 1.05 eq) and HOBt (0.446 g; 3.30 mmol; 0.1 eq; 135.12 g/mol). The flask is flushed with nitrogen gas and sealed with a septum. A nitrogen atmosphere is maintained using a needle attached to a nitrogen line at ~1 atm $N_2$ and the reaction progress is monitored by TLC. When no flupirtine remains by TLC, the reaction is worked up by adding 100 mL of water and stirring for 10 minutes under nitrogen. The contents of the flask are transferred to a separatory funnel and the layers are separated. The organic layer is washed two times with 0.1M sodium hydroxide solution and is dried over sodium sulfate. The volatiles are removed under vacuum and the residue is purified by column chromatography or recrystallisation to give the desired flupirtine-derived prodrug.

The general procedures of Examples 3 and 4 can be modified by those skilled in the art to employ for the syntheses of compounds comprised in Formula IV by proper substitution of other starting materials for ezogabine, flupirtine and acylating agents in appropriate amounts.

Example 3

General Procedure for Preparation of Amino Acid Prodrugs of Ezogabine:

Step 1: In a 500 mL round bottom flask equipped with a magnetic stirbar is placed dichloromethane (200 mL) at room temperature. Stirring is started and the following materials are added in order: Ezogabine (10.0 g, 33.00 mmol; 1.0 eq; 303.33 g/mol; [CAS #150812-12-7]), triethylamine (6.68 g; 66.00 mmol; 2.0 eq; 101.19 g/mol), the desired Boc-protected amino acid O-succinimide ester (34.62 mmol; 1.05 eq) and HOBt (0.446 g; 3.30 mmol; 0.1 eq; 135.12 g/mol). The flask is flushed with nitrogen gas and sealed with a septum. A nitrogen atmosphere is maintained using a needle attached to a nitrogen line at ~1 atm $N_2$ and the reaction progress is monitored by TLC. When no ezogabine remains by TLC, the reaction is worked up by adding 100 mL of water and stirring for 10 minutes under nitrogen. The contents of the flask are transferred to a separatory funnel and the layers are separated. The organic layer is washed two times with 0.1M sodium hydroxide solution and is dried over sodium sulfate. The volatiles are removed under vacuum and the residue is purified by column chromatography or recrystallisation to give the BOC-protected form of the desired prodrug.

Step 2: The product from Step 1 is added to a stirred solution of 25% trifluoroacetic acid in dichloromethane (100 mL) at room temperature. The flask is flushed with nitrogen gas and sealed with a septum. A nitrogen atmosphere is maintained using a needle attached to a nitrogen line at ~1 atm $N_2$ and the reaction progress is monitored by TLC. When no starting material or intermediates remain by TLC, the reaction is worked up by removing the volatile solvents under vacuum. The crude product is obtained as a mixture of the trifluoroacetate salts of the desired prodrug freebase. The material is purified either by recrystallization or by reverse phase HPLC to give the desired prodrug material.

Example 4

General Procedure for Preparation of Amino Acid Prodrugs of Flupirtine:

Step 1: In a 500 mL round bottom flask equipped with a magnetic stirbar is placed dichloromethane (200 mL) at room temperature. Stirring is started and the following materials are added in order: Flupirtine (10.0 g, 33.00 mmol; 1.0 eq; 303.33 g/mol; [CAS #56995-20-1]), triethylamine (6.68 g; 66.00 mmol; 2.0 eq; 101.19 g/mol), the desired Boc-protected amino acid O-succinimide ester (34.62 mmol; 1.05 eq) and HOBt (0.446 g; 3.30 mmol; 0.1 eq; 135.12 g/mol). The flask is flushed with nitrogen gas and sealed with a septum. A nitrogen atmosphere is maintained using a needle attached to a nitrogen line at ~1 atm $N_2$ and the reaction progress is monitored by TLC. When no flupirtine remains by TLC, the reaction is worked up by adding 100 mL of water and stirring for 10 minutes under nitrogen. The contents of the flask are transferred to a separatory funnel and the layers are separated. The organic layer is washed two times with 0.1M sodium hydroxide solution and is dried over sodium sulfate. The volatiles are removed under vacuum and the residue is purified by column chromatography or recrystallisation to give the BOC-protected form of the desired prodrug.

Step 2: The product from Step 1 is added to a stirred solution of 25% trifluoroacetic acid in dichloromethane (100 mL) at room temperature. The flask is flushed with nitrogen gas and sealed with a septum. A nitrogen atmosphere is maintained using a needle attached to a nitrogen line at ~1 atm $N_2$ and the reaction progress is monitored by TLC. When no starting material or intermediates remain by TLC, the reaction is worked up by removing the volatile solvents under vacuum. The crude product is obtained as a mixture of the trifluoroacetate salts of the desired prodrug freebase. The material is purified either by recrystallization or by reverse phase HPLC to give the desired prodrug material.

Example 5

Synthesis of Acetal Prodrug of Ezogabine.

Step 1:

Zinc oxide (44.73 g, 0.55 mol) was added to a solution of toluene (1800 mL) and 2-methylpropanoic acid (450 mL) and the flask was heated at 120° C. The water created in this process was removed by Dean Stark trap. After 5 h of heating, the temperature was lowered to 70° C. and then (1-chloroethyl) (4-nitrophenyl) carbonate (45 g, 0.18 mol) together with NaI (43.97 g, 0.29 mol) was added. The reaction mixture was stirred for 36 h at 70° C. After completion, the mixture was evaporated and the residue was dissolved in EtOAc, washed with saturated $NaHCO_3$ solution and then with brine. The organic layer was concentrated under reduced pressure and purified by silica gel column chromatography (petroleum ether:EtOAc=50:1) to give desired product as yellow solid (32.6 g, yield 55.68%).

Step 2:

To a stirred solution of ethyl N-(2-amino-4-{[(4-fluorophenyl)methyl]amino}phenyl) carbamate (24 g, 0.079 mol) in dichloromethane (480 mL) was added triethylamine (16.01 g, 0.16 mol), 1-[(4-nitrophenoxycarbonyl)oxy]ethyl 2-methylpropanoate (30.57 g, 0.10 mol), 1-Hydroxybenzotrizole (1.07 g, 0.007 mol) and stirred at 25° C. under nitrogen atmosphere for 24 h. After completion, the mixture was worked up by adding 300 mL of water and stirring for 10 minutes under nitrogen. The contents of the flask were transferred to a separatory funnel and the layers were separated. The organic layer was washed two times with 0.1M sodium hydroxide solution and was dried over sodium sulfate. The volatiles were removed under vacuum and the residue was purified by column chromatography (petroleum ether:EtOAc=6:1) to give Compound 3 as yellow solid (3.4 g, yield 9.3%).

$^1$H-NMR: (DMSO-$d_6$): δ (ppm): (multiplicity; J (Hz); Integral): 8.8-8.7 (bs, 1H), 8.3-8.2 (bs, 1H), 7.4 (m, 2H), 7.1 (m, 2H), 7.0-6.9 (bs, 1H), 6.8 (bs, 1H), 6.7 (q, 1H), 6.3 (m, 2H), 4.2 (m, 2H), 4.0 (m, 2H), 2.5 (m, 1H), 1.4 (m, 3H), 1.2 (m, 3H), 1.1 (m, 6H).

$^{13}$C-NMR: (DMSO-$d_6$): δ (ppm): 174.9, 162.7, 160.3, 152.0, 146.8, 136.7, 136.7, 129.3, 118.9, 115.5, 115.3, 109.0, 107.2, 89.5, 60.6, 46.3, 39.6, 33.6, 20.0, 19.0, 18.9, 15.0 ppm.

LCMS $R_t$=1.38 min; [M+H]=462

Example 6

Step 1:

To a stirred solution of ethyl N-(2-amino-4-{[(4-fluorophenyl)methyl]amino}phenyl) carbamate (10 g, 0.033 mol) in dichloromethane (200 mL) was added triethylamine (6.68 g, 0.066 mol), 2,5-dioxopyrrolidin-1-yl N2,N6-bis(tert-butoxycarbonyl)-L-lysinate (15.34 g, 0.035 mol), and 1-Hydroxybenzotrizole (0.44 g, 0.003 mol). The solution was stirred at 25° C. under a nitrogen atmosphere for 24 h. After completion, the mixture was worked up by adding 100 mL of water and stirring for 10 minutes under nitrogen. The contents of the flask were transferred to a separatory funnel and the layers were separated. The organic layer was washed two times with 0.1M sodium hydroxide solution and was dried over sodium sulfate. The volatiles were removed under vacuum and the residue was purified by column chromatography (petroleum ether:EtOAc=2:1) to give desired product as white solid (12.6 g, yield 60.5%).

General Scheme A

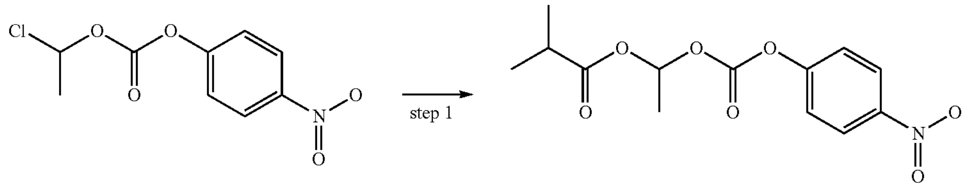

A1 A2

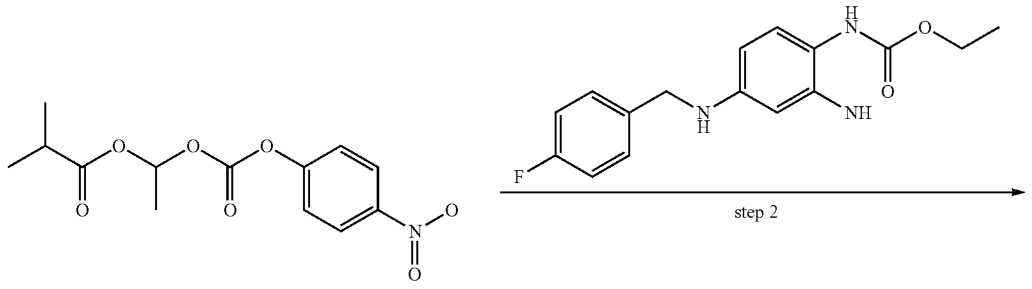

A2

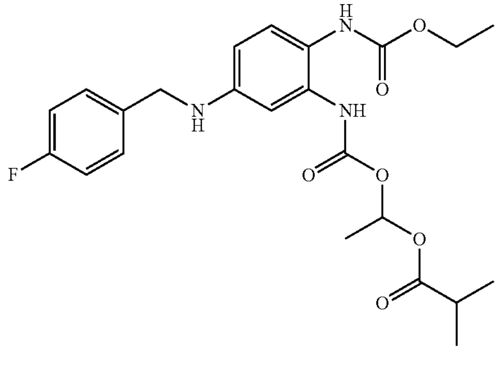

A3

Step 2:

A mixture of tert-butyl N-(5-{[(tert-butoxy)carbonyl] amino}-5-({2[(ethoxycarbonyl) amino]-5-{[(4 fluorophenyl)methyl]amino}phenyl}carbamoyl) pentyl)carbamate (8.67 g, 0.014 mol), and HCl (in dioxane)(17.5 mL, 0.069 mol) was prepared in dichloromethane (86 mL). The mixture was continuously stirred at R.T. for 18 h. After completion, the mixture was filtered and the filter cake was washed with dichloromethane and dried under reduced pressure to afford Compound 4 as a white solid (6.3 g, yield 98.1%).

$^1$H-NMR: (DMSO-$d_6$): δ (ppm); (multiplicity; J (Hz); Integral): 10.0-10.2 (bs, 1H), 8.5-8.4 (bs, 3H), 8.1-7.9 (bs, 3H), 7.4 (m, 2H), 7.2 (m, 3H), 7.1 (bs, 1H), 6.7 (bs, 1H), 4.3-4.2 (bs, 2H), 4.1 (m, 3H), 2.7 (bm, 2H), 1.8 (bm, 2H), 1.6 (m, 2H), 1.4 (m, 2H), 1.2 (m, 3H).

$^{13}$C-NMR: (DMSO-$d_6$): δ (ppm): 168.3, 161.2, 154.6, 132.3, 125.4, 115.7, 115.5, 61.0, 52.8, 38.7, 30.7, 26.8, 21.6, 15.0 ppm.

LCMS $R_t$=0.94 min; [M+H]=432

General Scheme B

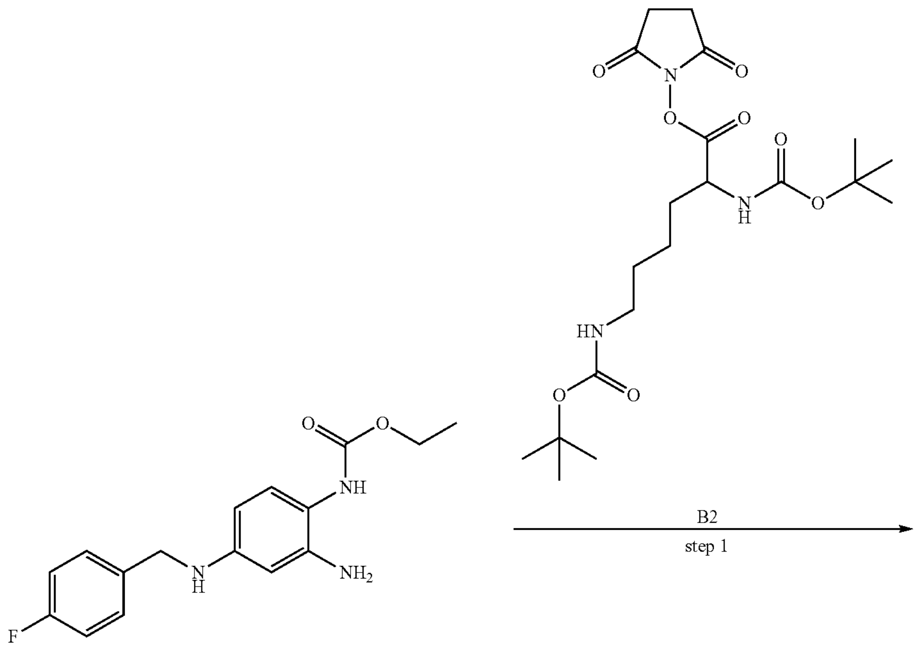

B1

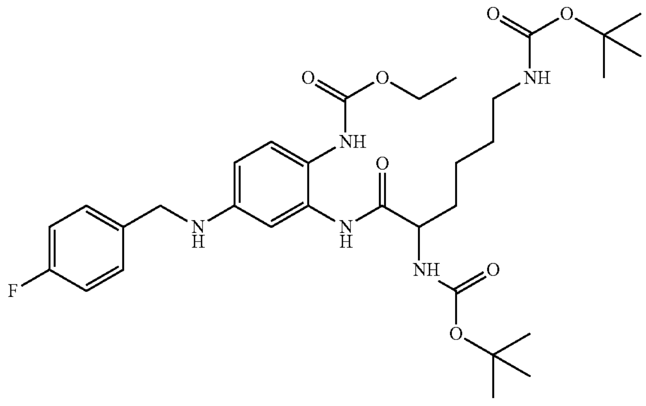

B3

-continued

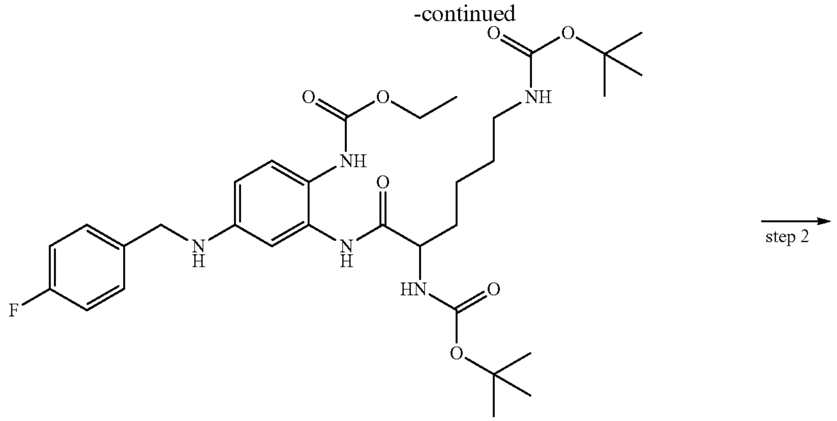

B3

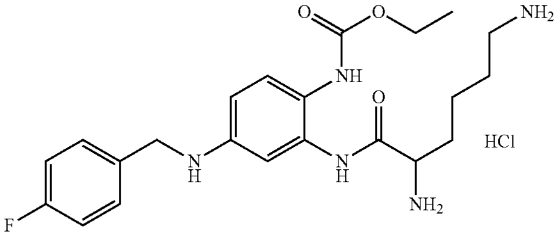

Example 7

Aqueous and Organic Solubility and Stability Studies of Ezogabine Prodrug Examples A study was undertaken to evaluate the solubility of 2 prodrugs of ezogabine (Compound 1) in different aqueous and organic media and assess their stability for up to 7 days by measuring UV absorption at 230 nm by HPLC-UV/Vis with mass spectrometer detection for confirmation of mass. The solubility of Compound 1 is known and presented in Table 1. Compound 1 solubility in solvent row 0.1N $Na_2HPO_4$ was determined in 0.1N $K_2HPO_4$.

Compound 3 and Compound 4 were evaluated in various solvents to compare their solubility to Compound 1. Compounds were weighed and placed into a 4 dram vials and solvents were added to the target concentration. Compounds were vortex and visually inspected for particulates and considered soluble if clear upon visual inspection with and without magnification. Solubility was reported as either greater than (>) or less than (<) from the prepared concentration. Compound 4 was evaluated for solubility at a maximum concentration of 20 mg/mL in water and 0.1N HCl and was freely soluble. It was evaluated at 10 mg/mL in 0.1 N NaCl and was freely soluble. It was evaluate at 1 mg/mL in 0.1 N NaOH and 0.1 N $Na_2HPO_4$ and was freely soluble. In ethanol and methanol it was freely soluble at a concentration of 75 mg/mL.

Compound 3 was not freely soluble at 1 mg/mL, by visual inspection, in 0.1 N HCl, 0.1 N NaOH, 0.1 N NaCl, water, 0.1 N $Na_2HPO_4$. It was freely soluble at 75 mg/mL in methanol and ethanol. It was soluble at 1 mg/mL in 1N HCl.

Both prodrug compounds are more soluble in alcohols than Compound 1. Compound 3 potentially has similar absolute solubility in aqueous media to Compound 1 while Compound 4 is superior in its solubility in aqueous solvents. For in vivo studies, Compound 4 has been formulated as a freely soluble solution in 0.9% w/v NaCl at a concentration of 150 mg/mL.

TABLE 1

Solvent Solubility Assessment of Ezogabine Prodrugs

| Solvents | Compound 4 Solubility (g/L) | Compound 3 Solubility (g/L) | Compound 1 Solubility (g/L) |
|---|---|---|---|
| Water | >20 | <1 | 0.05 |
| 0.1N HCl | >20 | <1 | 16 |
| 1N HCl | ND | >1 | ND |
| 0.1N NaOH | >1 | <1 | 0.04 |
| 0.1N NaCl | >10 | <1 | 0.04 |
| 0.1 Na2HPO4 | >1 | <1 | 0.18 |
| Methanol | >75 | >75 | 54 |
| Ethanol | >75 | >75 | 20 |

ND - not determined

Compounds in solvent were left on the benchtop exposed to light for up to 7 days since it is known that Compound 1 will degrade with light within 3-7 days.

Stability was assessed by taking an aliquot from the solubility vials at each test day. A single replicate was injected for each test condition. Samples from Compound 4 were diluted with water to a test concentration of 100 µg/mL. Samples from the alcohols from Compound 3 were diluted with methanol to 200 µg/mL and then further diluted with water to 100 µg/mL. The samples from the aqueous solvents from Compound 3 were diluted with methanol to 500 µg/mL.

Samples were injected onto an HPLC system with an aqueous mobile phase and acetonitrile organic phase and compounds were separated on a C8 50×2 mm column. Wavelength 230 nm was monitored for absorption and integrated for peak area while the mass spectrometer was used to confirm mass. Samples were tested on Day 1 and on subsequent days through Day 7.

Figure 1:
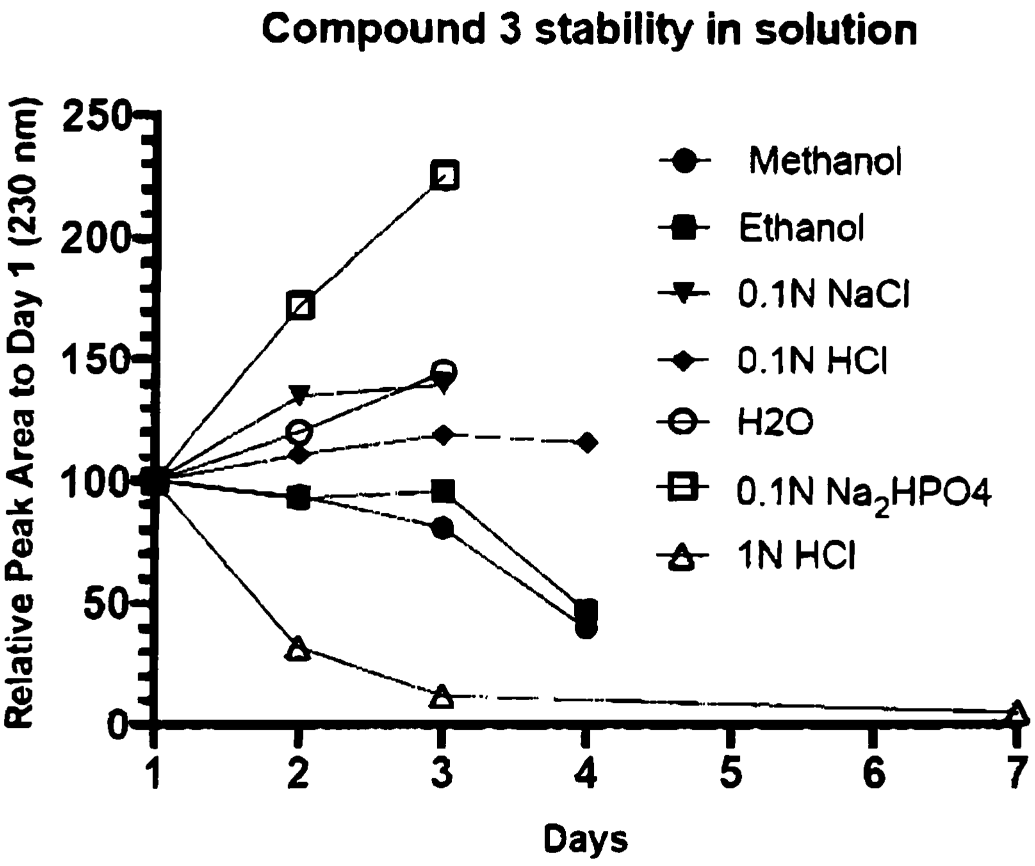
FIG. 1 is a graphical illustration of Compound 3 testing for Stability and Solubility over 3 to 7 Days.

Compound 3 stability and increase in solubility is presented in FIG. 1. Compound 3 increases in solubility over time with 0.1N $Na_2HPO_4$, $H_2O$, 0.1N NaCl from Day 1 to Day 3. Compound 3 appears to be stable over 4 days in 0.1 N HCl and is not stable in 1 N HCl over 7 days. Compound 3 is soluble and stable through 3 days in ethanol and methanol, while on Day 4 it exhibits degradation.

Figure 2:
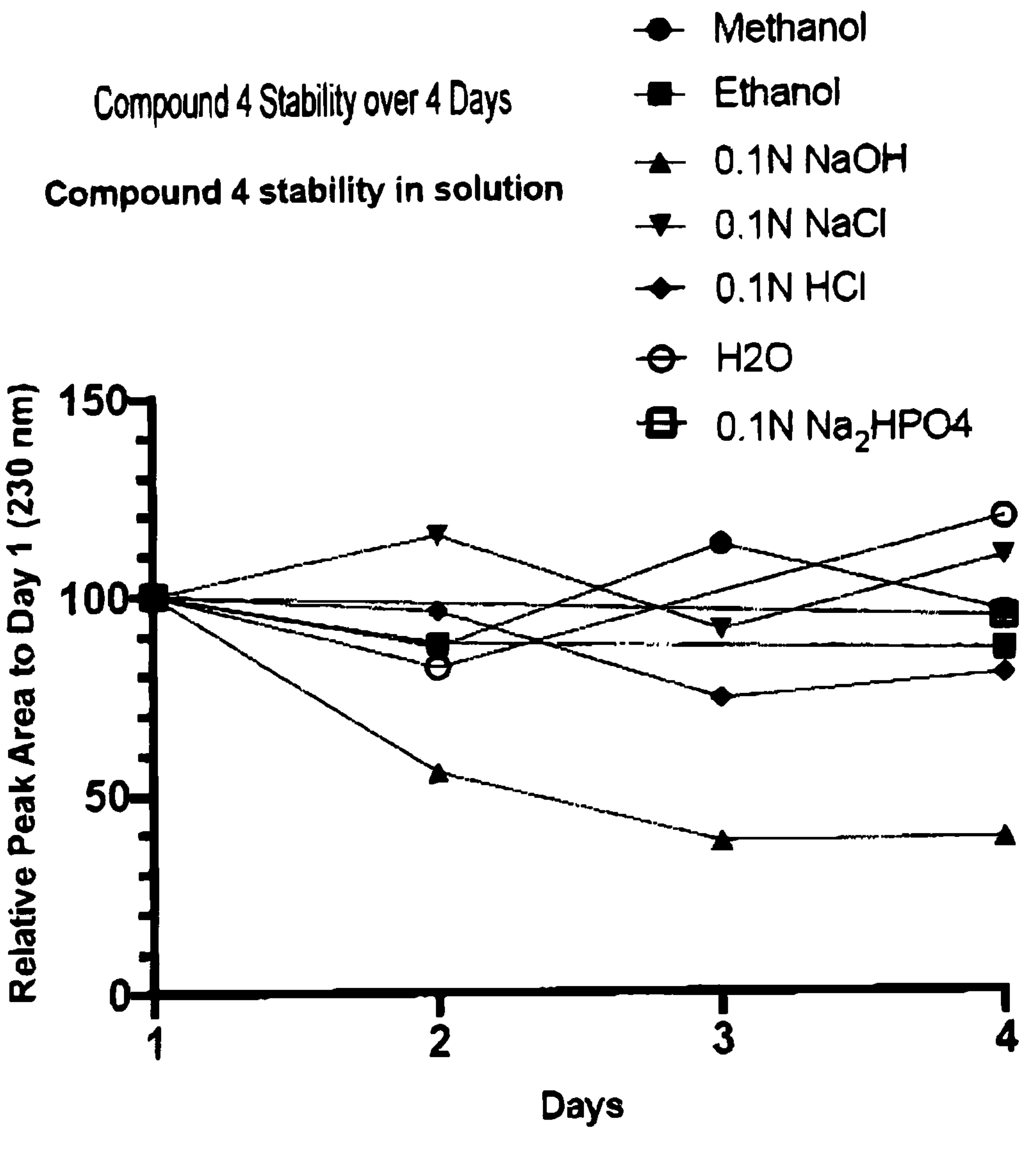
FIG. 2 is a graphical illustration of Compound 4 testing for Stability over 4 Days.

Compound 4 stability is presented in FIG. 2. Compound 4 appears stable in all test conditions except 0.1 N NaOH over 4 days. There is general variability of the peak area integration of +/−20% that suggest a trend of stability for all solvents except 0.1N NaOH, where Compound 4 has reduced in peak area by >50%.

Together, these results suggest greater solubility in alcohols for Compounds 3 and 4 over Compound 1 and greater solubility for Compound 4 in aqueous solvents over Compound 1. Except in select solvents, both prodrugs of Ezogabine are stable in solvents through 3 days.

FIG. 1 illustrates Stability and Solubility for Compound 3 over 3 to 7 Days. FIG. 2 illustrates Stability for Compound 4 over 4 Days Example 8

Plasma Stability Studies of Ezogabine Prodrug Examples

A study was undertaken to evaluate the stability of 2 prodrugs of ezogabine (Compound 1) in vitro in mouse and rat plasma at 37° C. for up to 23 hours.

Dry Compound #3 and Compound #4 were dissolved in dimethyl sulfoxide (DMSO) to a concentration 1 mg/mL and kept frozen at −20° C.

Plasma was collected by the biomaterial vendor and kept frozen at −20° C.

The 1 mg/mL DMSO solutions of Compound 3 and Compound 4 were diluted in rat and mouse plasma to a final concentration of 1000 ng/mL, vortexed and an aliquot was immediately removed, and plasma was precipitated with 4 volumes of acetonitrile with tolbutamide as an internal standard for mass spectrometer detection. The remaining was incubated for up to 23 h at 37° C. Samples were arrested at times points 0 min, 5 min, 30 min, 1 h, 2 h, 4 h, 6 h, and 23 h with a solution of ACN and tolbutamide (Internal Standard). The samples were analyzed by HPLC separation and mass spectrometry detection for prodrug amount, relative to a baseline time 0 control sample. Triplicate samples were generated at each time point and the peak area response was averaged and converted to a percent of baseline control.

Figure 3:
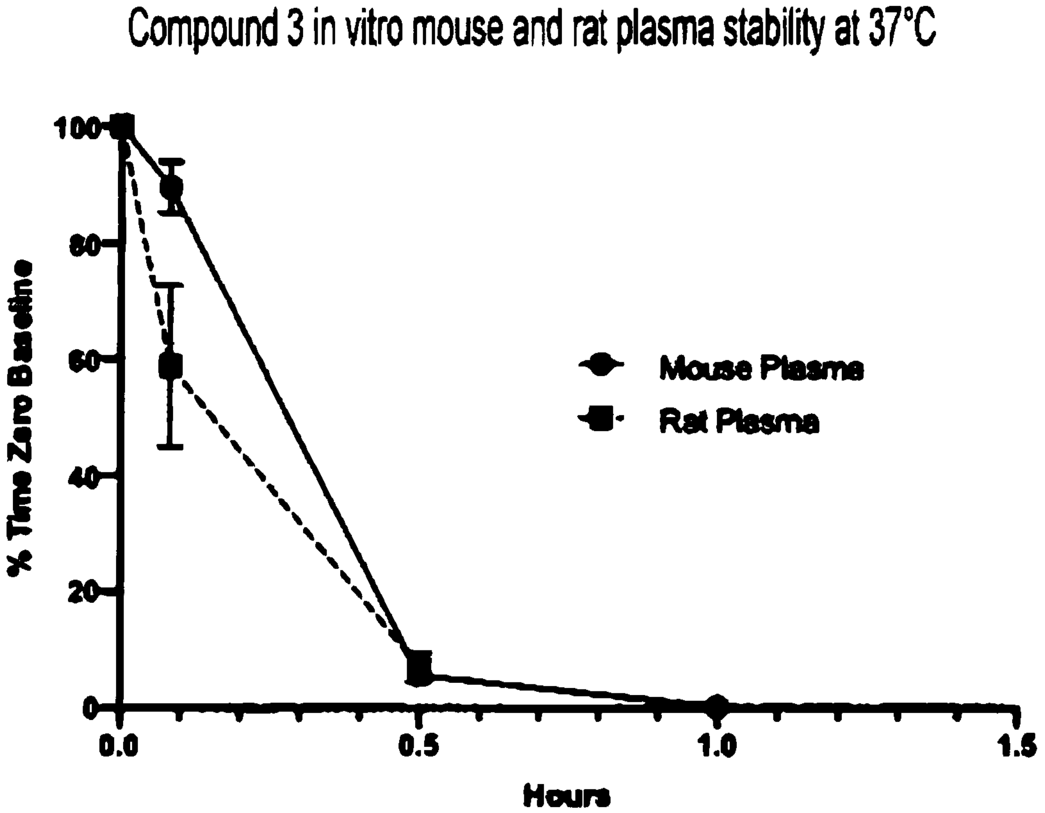
FIG. 3 is a graphical illustration of Compound 3 testing within in vitro mouse and rat plasma stability at 37° C.

Compound 3 is not stable in mouse and rat plasma, exhibiting full degradation in vitro by 1 h, FIG. 3. Compound 4 degrades by 6 hours in mouse plasma, however is stable through 6 hours in rat plasma and then is below 50% remaining at 23 h, FIG. 4. The ezogabine prodrugs elicit different stability profiles in plasma in vitro, which suggest that they may have different release kinetics in vivo.

Figure 4:
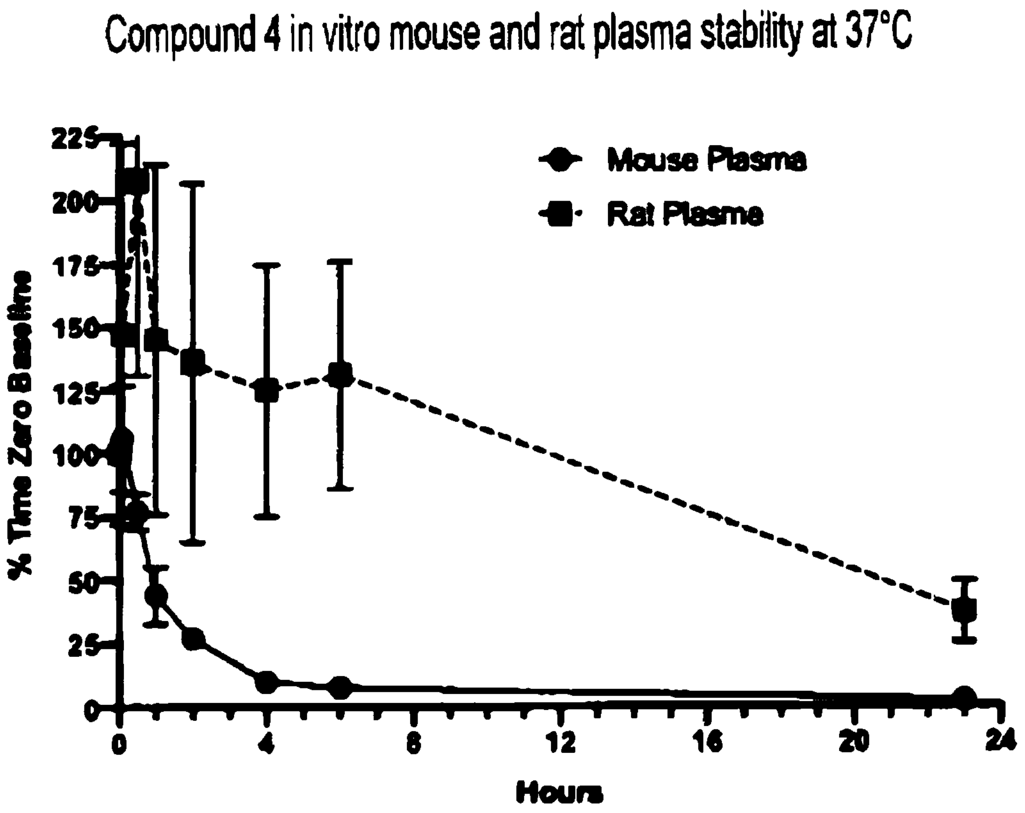
FIG. 4 is a graphical illustration of Compound 4 testing within in vitro mouse and rat plasma stability at 37° C.

FIG. 3 illustrates Compound 3 in in vitro mouse and rat plasma stability at 37° C. FIG. 4 illustrates Compound 4 in in vitro mouse and rat plasma stability at 37° C.

Example 9

The Pharmacokinetics of Ezogabine Prodrugs in Mouse.

Bioanalytical methods were developed on an API 4000 MS/MS system coupled to an Agilent 1100 HPLC and CTC PAL autosampler set a 4° C. for detection of Compound 1, its primary metabolite the N-acetyl metabolite and either Compound 3 or Compound 4. Separation by HPLC was achieved with a 50×2 mm C8 column with the HPLC operating in reverse phase. Blood was collected by cardiac stick with a 25 G ¾ length needle attached to a 1 mL syringe and transferred to $K_2EDTA$ tubes containing either 500 mM Citric Acid in water for studies conducted with Compound 4 or 500 mM Citric Acid containing 50 mM Dichlorvos for studies conducted with Compound 3. Blood was diluted by 10% with these stabilizers. These solutions were identified to stabilize compound 3 and Compound 4 from a set of experiments to determine the best method of preserving the Ezogabine prodrugs in plasma before extraction.

Extraction of the molecules was conducted by taking a 50 uL aliquot of plasma and adding 200 uL of acetonitrile containing 200 ng/mL tolbutamide as the internal standard. Samples were precipitated in a 96 well plate, centrifuges and an aliquot transferred to a new plate, dried down under heat and nitrogen and then reconstituted in the initial mobile phase conditions of the LC-MS/MS method. A standard curve was prepared for Compound 1, with or without the N-acetyl metabolite, separate from the prodrug. A standard curve was prepared from 5000 ng/mL to 1 ng/mL for each analyte. Concentration data from the bioanalytical run was analyzed by Phoenix Winnonlin version 8 for noncompartmental sparse sampling PK analysis, plotting of concentration time curves and tabulation of PK parameters.

Male mice 20-25 g of weight were administered either Compound 1, Compound 3 or Compound 4 by the subcutaneous or oral routes of administration with 4 mice at each time point. Animals were asphyxiated by carbon dioxide gas, blood was collected by cardiac stick and they were euthanized by cervical dislocation. Compound 4 was administered subcutaneously at a solution dose of 100 mg/kg in saline solution at a volume of 10 mL/kg. Time points for concentration analysis of Compound 1 and Compound 4 were collected at 0.083, 0.25, 0.5, 1, 2, 4, 8, 24 h (N=4/time point). FIG. 5 presents the mean (standard deviation) for Compound 4 after subcutaneous (SC) administration. Compounds 1, 3 and 4 were dosed to male mice at close to equimolar doses of Compound 1 by the oral route of administration. Compound 1 was dosed at 20 mg/kg while Compounds 3 and 4 were dosed at 30 mg/kg in a solution at a volume of 10 mL/kg. Compound 1 and Compound 3 were formulated in 5% ethanol: 20% Cremophor EL and 75% saline. Compound 4 was formulated in saline. The concentration in plasma for Compound 1 and the N-acetyl metabolite were assessed at 0.5, 1, 1.5, 2, 4 and 6 h. The concentration in plasma for Compound 1 after oral administration of either Compound 1, 3, and 4 is presented in FIG. 6 and the concentration of the metabolite is presented in FIG. 7.

The sparse sampling noncompartmental pharmacokinetic (PK) parameters are from these two studies are summarized in Table 2. Compound 3 and 4 delivered more Compound 1 to systemic circulation after oral administration through 6 h than compound 1 administered by itself, based on AUClast on a similar molar dose. Compound 4 delivers a lower Cmax compared to Compound 1, which may impart a reduced adverse event profile in clinical testing due to the lower Cmax and later Tmax. The metabolite is formed to at similar exposure levels regardless of prodrug or ezogabine but on a ratio basis, is produced less when Compound 1 is administered as Compound 3. Compound 1 has a slightly longer MRTlast (mean residence time through 6 h when administered as a prodrug and long half-life in a mouse when administered by subcutaneous administration as compound 4. The SC route of administration delivers more compound 1 when administered as compound 4 than the PO route based on AUClast/D.

TABLE 2

Noncompartmental PK parameters of Compound 1 (Ezogabine), metabolite and Prodrug after Oral (PO) or SC administration.

| Route/ Dose | Dosed | Analyte | Half-life (h) | Tmax (h) | Cmax (ng/mL) | Cmax/D (ng/mL/mg/kg) | AUClast (h*ng/mL) | AUClast/D (h*ng/mL/mg/kg) | MRTlast (h) |
|---|---|---|---|---|---|---|---|---|---|
| SC | Cmpd 4 | Cmpd 4 | 4.99 | 0.083 | 35450 | NC | 56750 | NC | NC |
| 100 mg/kg | | Cmpd 1 | 9.34 | 2.0 | 17200 | 257 | 117470 | 1753 | NC |
| PO | Cmpd 1 | NAM | NC | 0.50 | 99.6 | 4.98 | 121 | 6.06 | 2.21 |
| 20 mg/kg | | Cmpd 1 | NC | 0.50 | 2960 | 148 | 3800 | 190 | 2.39 |
| PO | Cmpd 3 | NAM | NC | 0.50 | 92.1 | 4.60 | 293 | 14.7 | 2.81 |
| 30 mg/kg | | Cmpd 1 | NC | 0.50 | 5670 | 283 | 15800 | 792 | 2.71 |
| 30 mg/kg | Cmpd 4 | NAM | NC | 1.0 | 37.5 | 1.87 | 144 | 7.18 | 2.87 |
| | | Cmpd 1 | NC | 4.0 | 1080 | 53.9 | 5210 | 261 | 3.17 |

Cmpd - compound, NAM - N-acetyl metabolite, NC - not calculated, PO - oral, SC - subcutaneous, AUClast for PO route is 6 h and 24 h for SC route.

FIGS. 5A and 5B illustrate Linear and Semilog Plot of Compound 1 and Compound 4 after administration of Compound 4 SC at 100 mg/kg in male mice. FIG. 6 illustrates a Semilog Plot of Compound 1 after administration of either Compound 1 at 20 mg/kg, Compound 3 at 30 mg/kg or Compound 4 at 30 mg/kg in male mice by the oral route. FIG. 7 illustrates a Semilog Plot of N-acetyl metabolite after administration of either Compound 1 at 20 mg/kg, Compound 3 at 30 mg/kg or Compound 4 at 30 mg/kg in male mice by the oral route.

Example 10

The Pharmacokinetics of Ezogabine Prodrugs in Rat

Bioanalytical methods were developed on an API 4000 MS/MS system coupled to an Agilent 1100 HPLC and CTC PAL autosampler set a 4° C. for detection of Compound 1, its primary metabolite the N-acetyl metabolite and either Compound 3 or Compound 4. Separation by HPLC was achieved with a 50×2 mm C8 column with the HPLC operating in reverse phase. Blood was collected by cardiac stick with a 25 G ¾ length needle attached to a 1 mL syringe and transferred to K2EDTA tubes containing either 500 mM Citric Acid in water for studies conducted with Compound 4 or 500 mM Citric Acid containing 50 mM Dichlorvos for studies conducted with Compound 3. Blood was diluted by 10% with these stabilizers. These solutions were identified to stabilize compound 3 and Compound 4 from a set of experiments to determine the best method of preserving the Ezogabine prodrugs in plasma before extraction.

Extraction of the molecules was conducted by taking a 50 uL aliquot of plasma and adding 200 uL of acetonitrile containing 200 ng/mL tolbutamide as the internal standard. Samples were precipitated in a 96 well plate, centrifuges and an aliquot transferred to a new plate, dried down under heat and nitrogen and then reconstituted in the initial mobile phase conditions of the LC-MS/MS method. A standard curve was prepared for Compound 1, with or without the N-acetyl metabolite, separate from the prodrug. A standard curve was prepared from 5000 ng/mL to 1 ng/mL for each analyte. Concentration data from the bioanalytical run was analyzed by Phoenix Winnonlin version 8 for noncompartmental PK analysis, plotting of concentration time curves and tabulation of PK parameters.

Male Sprague Dawley Rats 225-250 g of weight were jugular cannulated for IV administration and/or blood sample collection. Rats were administered either Compound 1, Compound 3 or Compound 4 by the intravenous, intramuscular or oral routes of administration with 2 rats for each dose group. 150 uL of blood were collected at predesignated time points. At completion of the study animals were asphyxiated by carbon dioxide gas and exsanguinated for euthanasia. Compound 1 and 3 were formulated in 5% ethanol: 20% Cremophor EL and 75% saline. Compound 4 was formulated in saline. Compounds 3 and 4 were administered at a dose of 5 mg/kg by IV bolus in a volume of 4 mL/kg. Compound 4 was administered at a dose of 75 mg/kg in a volume of 0.5 mL/kg by IM in the upper hind limb with 4 rats per time point. Compounds 1, 3 and 4 were dosed at equimolar doses of Compound 1 by the oral route of administration. Compound 1 was dosed at 20 mg/kg while Compounds 3 and 4 were dosed at 30 mg/kg in a solution at a volume of 5 mL/kg.

FIG. 8 presents the mean (standard deviation) for Compound 4 after intramuscular (IM) administration. The concentration in plasma for Compound 1 after oral administration of either Compound 1, 3, and 4 is presented in FIG. 9 and the concentration of the metabolite is presented in FIG. 10.

The noncompartmental pharmacokinetic (PK) parameters were generated from the individual rats and averaged for each study, which are summarized in Table 3. Compound 3 delivered more Compound 1 to systemic circulation after oral administration through 24 h than compound 1 administered by itself, based on AUClast on a similar molar dose and a lower Cmax. Compound 4 delivered a lower Cmax and an equivalent AUClast through 24 h for Compound 1 compared to itself, however, it may have been higher since there were no time points between 6 and 24 hour and Compound 1 had not started to clear. The rate of formation of Compound 1 was slowed in the prodrugs compared to the rate of absorption of Compound 1 administered as itself. This led to a later Tmax, which may reduce early onset treatment emergent adverse events. The longer the half-life of the prodrug the longer the half-life of compound 1. The IM route of administration delivers more Compound 1 when administered as Compound 4 than the oral route based on AUClast/D. Compound 1 has a slightly longer MRTlast (mean residence time through 24 h when administered as a prodrug and long half-life in a rat when administered compared to administration of itself. There was very little exposure of Compound 3 in systemic circulation after PO dosing (not reported) while Compound 4 was slightly more detectable in systemic circulation after PO dosing (not reported).

TABLE 3

Noncompartmental Mean PK parameters of Compound 1 (Ezogabine), metabolite and Prodrug after Oral (PO), IV or IM administration.

| Route/ Dose | Dosed | Analyte | Half-life (h) | Tmax (h) | Cmax (ng/mL) | Cmax/D (ng/mL/mg/kg) | AUClast (h*ng/mL) | AUClast/D (h*ng/mL/mg/kg) | MRTlast (h) |
|---|---|---|---|---|---|---|---|---|---|
| IV | Cmpd 3 | Cmpd 3 | 4.59 | 0.05 | 7920 | NC | 2000 | NC | 2.16 |
| 5 mg/kg | | Cmpd 1 | 2.88 | 0.5 | 384 | 1145 | 417 | 124 | 3.05 |
| IV | Cmpd 4 | Cmpd 4 | 11.2 | 0.05 | 8280 | NC | 2840 | NC | 3.06 |
| 5 mg/kg | | Cmpd 1 | 16.2 | 5.0 | 255 | 76 | 282 | 84 | 7.23 |
| IM | Cmpd 4 | Cmpd 4 | 4.20 | 0.083 | 32900 | NC | 51100 | NC | 3.73 |
| 75 mg/kg | | Cmpd 1 | 4.63 | 3.5 | 7640 | 153 | 54400 | 1090 | 7.51 |
| PO | Cmpd 1 | NAM | 10.5 | 0.75 | 207 | 10.4 | 1220 | 61.0 | 8.23 |
| 20 mg/kg | | Cmpd 1 | 6.28 | 0.16 | 897 | 44.8 | 5590 | 280 | 7.31 |
| PO | Cmpd 3 | NAM | NC | 15 | 59.8 | 2.99 | 1010 | 50.7 | 14.8 |
| 30 mg/kg | | Cmpd 1 | NC | 13 | 742 | 37.1 | 13800 | 689 | 12.7 |
| 30 mg/kg | Cmpd 4 | NAM | NC | 6.0 | 154 | 7.70 | 2130 | 106 | 11.3 |
| | | Cmpd 1 | NC | 4 | 465 | 23.3 | 5240 | 262 | 9.53 |

Cmpd - compound, NA - Not applicable, NAM - N-acetyl metabolite, NC - not calculated, PO - oral, IM - intramuscular, IV- intravenous, AUClast is 24 h.

FIG. 8 illustrates a Semilog Plot of Compound 1 and Compound 4 after administration of Compound 4 IM at 75 mg/kg in male rat. FIG. 9 illustrates a Semilog Plot of Compound 1 after administration of either Compound 1 at 20 mg/kg, Compound 3 at 30 mg/kg or Compound 4 at 30 mg/kg in male Sprague Dawley Rat by the oral route. FIG. 10 illustrates a Semilog Plot of N-acetyl metabolite after administration of either Compound 1 at 20 mg/kg, Compound 3 at 30 mg/kg or Compound 4 at 30 mg/kg in male mice by the oral route.

Example 11

Ezogabine Prodrugs are Inactive on the Molecular Target Kv7.2/7.3

Human Kv7.2/7.3 cells are harvested, counted and seeded in black, clear-bottomed 96 well plates at a density of 50,000 cells per well in 100 μl volume and incubated overnight. The following day, media was removed and 40 μl of loading buffer (4.895 mL HBSS:HEPES, 50 μL probenecid, 50 μL power load, 5 μl FluxOR reagent) was added and incubated at room temperature for 30 minutes. After incubation loading buffer was removed and 40 μl of assay buffer added (4.45 ml HBSS:HEPES, 500 μl FluxOR assay buffer and 50 μL probenecid) and incubated for 10 minutes. FLIPR then added 10 μl of stimulus buffer along with either vehicle, test compound or reference agonist and fluorescence was monitored for 5 minutes at ex/em: 488 nm/510-570 nm. Compound 3 and Compound 4 were tested in replicate in a 7 point concentration response from 0.03 to 30 μM and Ezogabine was tested from 0.01 to 10 μM in replicate and the relative fluorescence unit (R.F.U.) was plotted against concentration. Compound 3 and Compound 4 are inactive against the primary target of Kv7.2/7.3. Compound 1 has an $EC_{50}$ of 1.6 μM in this assay.

FIG. 11 illustrates an In vitro Screen of Kv7.2/7.3 Voltage Gated Potassium Channels Example 11

Ezogabine Prodrugs Deliver Effective Concentrations of Ezogabine in vivo to block Maximal Electroshock (MES) in Mouse.

CF-1 male mice (N=8) were treated IP with vehicle, Compound 3, Compound 4, Compound 1, Phenytoin, or Diazepam (0, 150, 100, 100, 8, and 20 mg/kg, respectively) and then administered a 60 Hz corneal stimulation (50 mA). All treatments were administered 30 minutes prior to MES, except for Phenytoin which was administered 1 h prior.

All mice in vehicle group showed colonic seizure after a few seconds of receiving MES. Mice that were treated with the remaining treatments generally reached the 6 second maximal time limit without showing signs of a seizure.

FIG. 12 illustrates a CF-1 Mouse Maximal Electroshock (MES) Test

CF-1 mice (N=8) were treated with Compound 1, Compound 3 and Compound 4 (150, 100, and 100 mg/kg, respectively) via IP administration had blood collected after MES for Compound 1 concentration analysis. The concentration of Compound 1 present in plasma is greater after administration of Compound 3 or Compound 4 than with Compound 1 alone, FIG. 13. Compound 1 from Compound 3 was 5.5-fold higher and Compound 1 from Compound 4 was 9-fold.

FIG. 13 illustrates a CF-1 Mouse Concentration of Compound 1.

Example 12

Ezogabine Prodrugs Deliver Effective Concentrations of Ezogabine In Vivo to Block Maximal Electroshock (MES) in Rat.

SD Rats (N=4) were treated IM with Compound 4 (75 mg/kg) and administered a 60 Hz corneal stimulation (100 mA). All treatments were at 0.083, 0.25, 0.5, 1, 2, 4, and 8 hours prior to the administration of MES test, where 6 seconds where 6 seconds without a seizure was considered protected.

Rats showed an increase of protection from seizures as time increased, were almost fully protected at 1 h and were fully protected from 2 through 8 hours post dose. FIG. 14 summarized the mean (SD) group mean time to seizure.

FIG. 14 illustrates a SD Rat Protection of Compound 4 after IM administration to MES Induced Seizures Example 13

Compound 3 was tested for reversal of mechanical hypersensitivity to the pin prick test for hindlimb paw withdraw and the von Frey hairs for gram force mechanical allodynia in the CCI model of neuropathic pain. Male Sprague Dawley rats (n=8/group) were tested for baseline sensitivity on Day 1 (ipsilateral and contralateral paws) and administered XYG-203 orally; 40 mg/kg on Day 1, 20 mg/kg Day 3, 10 mg/kg Day 5, 5 mg/kg Day 7, 1 mg/kg Day 10 and baseline on Day 12. Mechanical hypersensitivity was tested 1 h after pretreatment. Data (mean±SD) were analyzed with a repeated measures ANOVA with Dunnet's adjustment for multiple comparisons. At 5 mg/kg for Compound 3 the 95% confidence intervals did not cross the baseline mean and 40 mg/kg reduced the latency of neuropathic ipsilateral paw withdrawal by 9.2 seconds (p=0.0003) and increased the gram force to paw lift significantly. There was no significant difference between Day 0 and Day 12 baseline values for either ipsilateral and contralateral hind paws indicating that there was no learned behavior and no accumulation of drug effect on the ipsilateral paw. In addition, the contralateral paw response did not change significantly over the course of the study. The results are shown in FIGS. 15, 16 and 17.

Compound 3 was dosed at an equimolar dose to Ezogabine (20 mg/kg) with the same formulation (0.5% methylcellulose in water) in male jugular vein cannulated rats. Blood samples were collected at the same time points over 24 hours to generate a concentration time profile. Two male rats were dosed per group. Plasma samples were analyzed by LC/MS/MS and the resulting concentration time profiles and PK parameters are provided. Cmpd 3 provided >2-fold the total exposure of ezogabine on a given molar dose than ezogabine. There is also essentially no detectable compound 3 in systemic circulation.

| Dosed | Analyte | Tmax (h) | Cmax (ng/mL) | AUClast (h*ng/mL) | Cmax/D (ng/mL/ mg/kg) | AUClast/D (h*ng/mL/ mg/kg) |
|---|---|---|---|---|---|---|
| Cmpd 3 | Cmpd 3 | 2.00 | 0.545 | 0.273 | 0.0273 | 0.0136 |
| | Ezogabine | 24.0 | 636 | 13800 | 31.8 | 690 |
| Ezogabine | Ezogabine | 0.160 | 897 | 5620 | 44.8 | 281 |

Compound 4 was assessed in the rat formalin inflammatory model. The number of flicks/licks of a male CD-1 mouse in the acute phase 0-10 minute and the inflammatory phase from 15-40 min after intraplantar administration of 50 µL of 5% formalin was recorded. Saline or Compound 4 (100 mg/kg in water) were administered SC 5 mL/kg 30 minutes before application of formalin (n=8/group). A 50% reduction in behavioral response was observed for compound 4 compared to vehicle in both phases. Data is presented over the duration of the observation periods in 2 minute bins. Compound 4 demonstrates a reduction in inflammatory pain. The results are shown in FIG. 18.

Compound 6

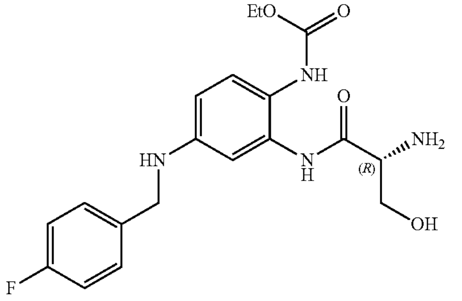

Chemical Formula: $C_{19}H_{23}FN_4O_4$
Exact Mass: 390.17
Molecular Weight: 390.42

Compound 4, 6 and 29 were dosed at an equimolar dose to Ezogabine (20 mg/kg) with the same formulation (0.5% methylcellulose in water) in male jugular vein cannulated rats. Blood samples were collected at the same time points over 24 hours to generate a concentration time profile. Two male rats were dosed per group. Plasma samples were analyzed by LC/MS/MS and the resulting concentration time profiles and PK parameters are provided. Cmpd 4, 6 and 29 delivered similar dose normalized AUC total exposure ezogabine as ezogabine itself. However cmpd 4 exhibited the lowest exposure of itself in plasma then Cmpd 4 followed by Cmpd 29. Cmpd 4 and 29 delivered an ezogabine Cmax that was about ½ of ezogabine itself, whereas Cmpd 6 delivered an ezogabine Cmax that was approximately 2-fold higher than ezogabine itself.

| Dosed | Analyte | Tmax (h) | Cmax (ng/mL) | AUClast (h*ng/mL) | Cmax/ D (ng/ml/ mg/kg) | AUClast/ D (h*ng/ml/ mg/kg) |
|---|---|---|---|---|---|---|
| Cmpd 4 | Cmpd 4 | 1.00 | 46.8 | 125 | 2.34 | 6.26 |
| | Ezogabine | 6.00 | 403 | 5240 | 20.2 | 262 |
| Cmpd 6 | Cmpd 6 | 0.160 | 4660 | 3970 | 233 | 199 |
| | Ezogabine | 0.160 | 1640 | 4930 | 82.0 | 246 |
| Cmpd 29 | Cmpd 29 | 0.160 | 883 | 6110 | 44.2 | 305 |
| | Ezogabine | 0.160 | 466 | 6180 | 23.3 | 309 |
| Ezogabine | Ezogabine | 0.160 | 897 | 5620 | 44.8 | 281 |

The results are shown in FIG. 19.

Compound 28

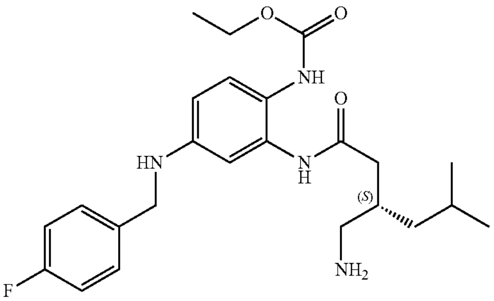

Chemical Formula: $C_{24}H_{33}FN_4O_3$
Exact Mass: 444.25
Molecular Weight: 444.55

Compound 28 was tested in the maximal electroshock assay in CF-1 mice 30 minutes after drug administration by the IP route to determine its ability to release ezogabine and provide protection to the assay. Drug concentration analysis of compound 28, ezogabine, and pregabalin were determined by LC/MS/MS assay in plasma and brain. Compound 28 was evaluated in a dose response in maximal electroshock at Vehicle, 1.5, 3, 6, 12 and 24 mg/kg. Drug levels of ezogabine and compound 28 were evaluated. An additional group at 24 mg/kg was evaluated for exposure of compound 28, ezogabine and pregabalin in plasma and brain. None of the doses showed complete protection against MES induced seizures. At 12 mg/kg 1 of 9 animals, and at 24 mg/kg 3 of 9 animals were protected from MES induced seizures. However, there was a clear increase in protection with the increase of ezogabine concentrations. Compound 28 was also present at higher concentrations than ezogabine, indicating that it still had not fully released ezogabine. The results are shown in FIGS. 20 and 21.

Compound 28 was also dosed at an equimolar dose to Ezogabine (20 mg/kg) with the same formulation (0.5% methylcellulose in water) in male jugular vein cannulated rats. Blood samples were collected at the same time points over 24 hours to generate a concentration time profile. Two male rats were dosed per group. Plasma samples were analyzed by LC/MS/MS and the resulting concentration time profiles and PK parameters are provided. Cmpd 28 provided lower exposure of ezogabine on a given molar dose than ezogabine. Both Ezogabine and Compound 28 were present at similar concentration in the rat.

| Dosed | Analyte | Tmax (h) | Cmax (ng/mL) | AUClast (h*ng/mL) | Cmax/D (ng/ml/mg/kg) | AUClast/D (h*ng/ml/mg/kg) |
|---|---|---|---|---|---|---|
| Cmpd 28 | Cmpd 28 | 2.00 | 186 | 1660 | 9.31 | 83.0 |
| | Ezogabine | 2.00 | 172 | 1210 | 8.58 | 60.7 |
| Ezogabine | Ezogabine | 0.160 | 897 | 5620 | 44.8 | 281 |

The results are also shown in FIG. 22.

Compound 29

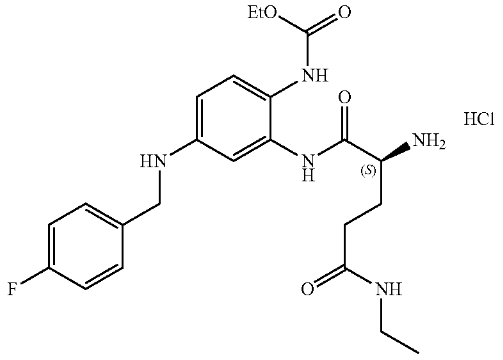

Chemical Formula: $C_{23}H_{30}FN_5O_4$
Molecular Weight: 459.52

Compound 29 was evaluated in the mouse maximal electroshock (MES) assay for efficacy at an oral dose of 30 mg/kg. Blood samples were collected for plasma analysis of Compound 29 and Ezogabine by LC/MS/MS after completion of the assay. Each male CF-1 mouse provided one data point in the MES assay and one data point in the concentration analysis. There were 8 mice per time point. Exposure of ezogabine was very high in plasma and was present in brain and reduced in concentration over the three time points, 0.25, 0.5 and 1 h. Pharmacological response reduced in tandem to the decrease in brain concentrations. The results are shown in FIG. 23.

Example 14

Acid and Organic Solution Stability of Ezogabine and Prodrugs.

Ezogabine is not soluble at neutral pH but is soluble at low pH. However at low pH (1 N HCl) and in simulated gastric fluid (hydrochloric acid, sodium chloride and pepsin) it degrades and forms a chromophore dimer. An HPLC-UV Vis method was developed using 0.1% Formic acid in water as mobile phase A and 0.1% Formic acid in acetonitrile as mobile Phase B. A gradient method was developed ramping from 10% A to 90% B over 8 minutes and then returning to 10% A at 8.5 minutes on a 4.6×50 mm Zorbax C-18 column. Injections of 10 uL of stability solutions were injected for analyte detection.

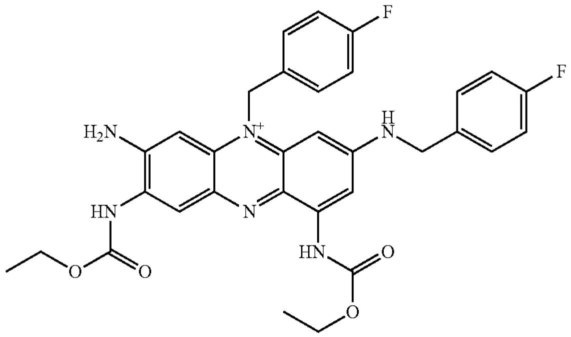 [SMILES: CCOC(=O)Nc1cc2nc3c(NC(=O)OCC)cc(NCc4ccc(F)cc4)cc3[n+](Cc3ccc(F)cc3)c2cc1N]

When ezogabine is prepared at 8 mg/mL in simulated gastric fluid (SGF) and stored at 38° C., concentrations of the dimer over 8 hours increase to 1980 ng/mL in solution, see table below for % conversion to dimer and concentration. The structure of the dimer is presented.

| Test Condition and Time | % Conversion to dimer | Concentration of dimer |
|---|---|---|
| SGF Blank | 0 | 0.00 ng/ml |
| SGF Time 0 | 0 | 0.00 ng/ml |
| SGF Time 1 h | 0.250% | 19.5 ng/ml |
| SGF Time 4 h | 7.95% | 623 ng/ml |
| SGF Time 8 h | 25.2% | 1980 ng/ml |

Ezogabine at 5 mg/mL was prepared in a weak acid (0.1 N HCl), methanol and acetonitrile and evaluated for degradation for up to 2 weeks at room temperature. Aliquots were collected at serial time points and then diluted to a nominal concentration of 100 ug/mL for injection to the HPLC and 250 nm monitored by the diode array detector. Data at approximately 10 days is presented. The acid solutions were turning light purple (indicating degradation) by Day 2, while the organic solvent solutions did not begin turning purple until Day 7.

| Test Condition (room temp., normal light) | Ezogabine Retention Time (min) | Baseline Area (mAU) | Stability Time Point (h) | Area (mAU) | % Remaining |
|---|---|---|---|---|---|
| 0.1N HCl | 4.4 | 6005 | 267 | 3046 | 50.7% |
| 1N HCl | 4.4 | 6517 | 267 | 4442 | 68.2% |
| Methanol | 4.4 | 6517 | 267 | 2690 | 41.3% |
| Acetonitrile | 4.4 | 3191 | 219 | 1434 | 44.9% |

Compound 3 at 5 mg/mL was prepared in acidic solution (0.1 N and 1.0 N HCl), ethanol, methanol and acetonitrile and evaluated for degradation for up to 3 weeks at room temperature. Aliquots were collected at serial time points and then diluted to a nominal concentration of 100 ug/mL for injection to the HPLC and 250 nm monitored by the diode array detector. Compound 3 at 0.1 N HCl turned a light tan, while at 1 N HCl turned a golden yellow by Day 9. The organic solvents were clear and colorless through Day 18. Compound 3 converts to ezogabine under acidic conditions but does not in organic solvent.

| Test Condition (room temp., normal light) | Cmpd 3 Retention Time (min) | Stability Time Point (h) | Cmpd 3 Baseline Area (mAU) | Cmpd 3 Area (mAU) | % Re-maining | Ezogabine Area (mAU) |
|---|---|---|---|---|---|---|
| 0.1N HCl | 6.0 | 433 | 1577 | 186 | 11.8% | 400 |
| 1N HCl | 6.0 | 97 | 2637 | 47 | 1.78% | 2881 |
| Ethanol | 6.0 | 390 | 2403 | 2345 | 97.6% | 43 |
| Methanol | 6.0 | 435 | 2140 | 2025 | 94.6% | 41 |
| Acetonitrile | 6.0 | 435 | 1858 | 1680 | 90.4% | 51 |

Compound 4 at 5 mg/mL was prepared in acidic solution (0.1N, 1N, 2N HCl), phosphate buffered saline (PBS), and methanol and evaluated for degradation for up to 3 weeks at room temperature. It was also evaluated at 2 N HCl at 37° C. Aliquots were collected at serial time points and then diluted to a nominal concentration of 100 ug/mL for injection to the HPLC and 250 nm monitored by the diode array detector. Compound 4 remained clear and colorless through Day 18. Compound 4 exhibits very little degradation to ezogabine and thus does not form the dimer under acidic conditions.

| Test Condition (room temp., normal light) | Cmpd 4 Retention Time (min) | Stability Time Point (h) | Cmpd 4 Baseline Area (mAU) | Cmpd 4 Area (mAU) | % Re-maining | Ezogabine Area (mAU) |
|---|---|---|---|---|---|---|
| 0.1N HCl | 3.5 | 269 | 5674 | 5912 | 104.2% | 0 |
| 1N HCl | 3.5 | 269 | 4962 | 5099 | 102.8% | 0 |
| 2N HCl | 3.5 | 269 | 4913 | 4936 | 100.5% | 38 |
| 2N HCl 37C | 3.5 | 436 | 4606 | 4373 | 94.9% | 167 |
| PBS | 3.5 | 435 | 3757 | 3726 | 99.2% | 0 |
| Methanol | 3.5 | 437 | 1567 | 1544 | 98.5% | 0 |

Compound 6 at 5 mg/mL was prepared in acidic solution (1 N, 2N HCl), and methanol and evaluated for degradation for up to 3 weeks at room temperature. It was also evaluated at 2 N HCl at 37° C. Aliquots were collected at serial time points and then diluted to a nominal concentration of 100 ug/mL for injection to the HPLC and 250 nm monitored by the diode array detector. Compound 6 remained clear and colorless through Day 18. Compound 6 exhibits very little degradation to ezogabine and thus has low probability to form the dimer under acidic conditions.

| Test Condition (room temp., normal light) | Cmpd 6 Retention Time (min) | Stability Time Point (h) | Cmpd 6 Baseline Area (mAU) | Cmpd 6 Area (mAU) | % Re-maining | Ezogabine Area (mAU) |
|---|---|---|---|---|---|---|
| 1N HCl | 3.9 | 437 | 6957 | 5838 | 83.9% | 58 |
| 2N HCl | 3.9 | 437 | 6263 | 6591 | 105.2% | 177 |
| 2N HCl 37C | 3.9 | 437 | 7768 | 6430 | 82.8% | 461 |
| Methanol | 3.9 | 437 | 3375 | 2288 | 67.7% | 184 |

Compound 28 at 5 mg/mL was prepared in acidic solution (0.1 N, 1N, 2N HCl), and methanol and evaluated for degradation for up to 3 weeks at room temperature. It was also evaluated at 2 N HCl at 37° C. Aliquots were collected at serial time points and then diluted to a nominal concentration of 100 ug/mL for injection to the HPLC and 250 nm monitored by the diode array detector. Compound 28 remained clear and colorless through Day 11 for the acidic solutions and acetonitrile and through Day 7 for methanol. Compound 28 exhibits degradation to ezogabine with increasing strength of the acidic solution.

| Test Condition (room temp., normal light) | Cmpd 28 Retention Time (min) | Stability Time Point (h) | Cmpd 28 Baseline Area (mAU) | Cmpd 28 Area (mAU) | % Re-maining | Ezogabine Area (mAU) |
|---|---|---|---|---|---|---|
| 0.1N HCl | 4.3 | 440 | 5856 | 3964 | 67.7% | 0 |
| 1N HCl | 4.3 | 440 | 5026 | 4552 | 90.5% | 568 |
| 2N HCl | 4.3 | 440 | 5926 | 3764 | 63.5% | 1462 |
| 2N HCl 37C | 4.3 | 440 | 5180 | 1770 | 34.2% | 3593 |
| Methanol | 4.3 | 440 | 2593 | 2385 | 92.0% | 0 |
| Acetonitrile | 4.3 | 440 | 2368 | 1836 | 77.5% | 248 |

Compound 29 at 5 mg/mL was prepared in acidic solution (0.1 N, 1N, 2N HCl), acetonitrile and methanol and evaluated for degradation for up to 3 weeks at room temperature. It was also evaluated at 2 N HCl at 37° C. Aliquots were collected at serial time points and then diluted to a nominal concentration of 100 ug/mL for injection to the HPLC and 250 nm monitored by the diode array detector. Compound 28 remained clear and colorless through Day 18 for the acidic solutions and through Day 3 for methanol. Compound 29 exhibits degradation under acidic conditions and also conversion to ezogabine and thus may form the dimer under acidic conditions.

| Test Condition (room temp., normal light) | Cmpd 29 Retention Time (min) | Stability Time Point (h) | Cmpd 29 Baseline Area (mAU) | Cmpd 29 Area (mAU) | % Remain-ing | Ezogabine Area (mAU) |
|---|---|---|---|---|---|---|
| 0.1N HCl | 4.1 | 441 | 5779 | 2731 | 47.3% | 0 |
| 1N HCl | 4.1 | 441 | 5419 | 2082 | 38.4% | 1241 |
| 2N HCl | 4.1 | 441 | 5681 | 1747 | 30.7% | 1659 |
| 2N HCl 37C | 4.1 | 441 | 5047 | 35 | 0.69% | 1755 |
| Methanol | 4.1 | 441 | 2234 | 1692 | 75.7% | 0 |

All publications, patents, and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

What is claimed is:

1. A compound of Formula I:

Formula I

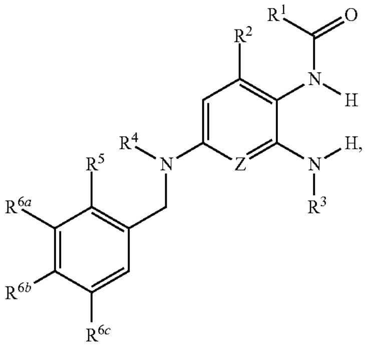

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is CH;

$R^3$ is "Pro" wherein "Pro" is selected from the group consisting of $C(O)R^{10}$;

$R^{10}$ is a hydrolysable prodrug moiety of the structure $OL^1OC(O)R^{11}$, where $R^{11}$ is unsubstituted or substituted $C_1$-$C_{10}$ alkyl, aryl, $C_1$-$C_{10}$ aralkyl;

$L^1$ is $C_1$-$C_{10}$ alkylene, wherein the two oxygen atoms depicted as attached to $L^1$ are on the same carbon atom within $L^1$;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, or a pharmaceutically acceptable salt thereof.

2. A compound of Formula III:

Formula III

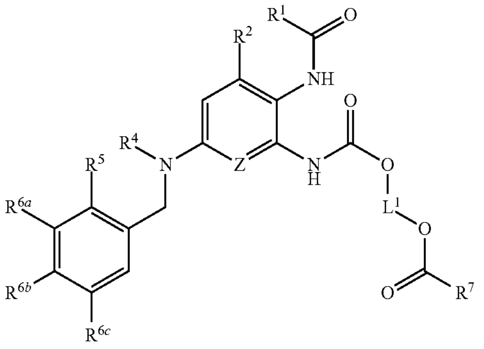

wherein $R^1$ is $C_{1-6}$ alkyl, $C_{1-6}$ alkoxy, $C_{1-6}$ alkyl-$C_{3-6}$ cycloalkyl;

$R^2$ is H, $C_{1-3}$ alkyl, $C_{1-3}$ alkoxy, halogen, $C_{1-3}$ haloalkoxy;

Z is CH;

each of $R^4$ and $R^5$ independently is H, or $R^4$ and $R^5$, taken together with the atoms to which they are bound, form a 5 to 6 membered ring, optionally containing one or more degree of unsaturation; and each of $R^{6a}$, $R^{6b}$, and $R^{6c}$ independently is H or halogen, where at least one of $R^{6a}$, $R^{6b}$, and $R^{6c}$ is H, $R^7$ is $C_{1-6}$ alkyl, phenyl, or $C_{1-2}$ alkyl-phenyl, and $L^1$ is $C_1$-$C_{10}$ alkylene, wherein the two oxygen atoms depicted as attached to $L^1$ are on the same carbon atom within $L^1$, or a pharmaceutically acceptable salt thereof.

3. The compound of claim 2, wherein the compound is of Formula III-A:

Formula III-A

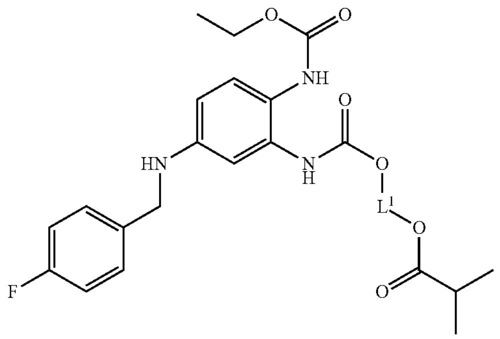

wherein $L^1$ is $C_1$-$C_{10}$ alkylene wherein the two depicted oxygen atoms on $L^1$ are on the same carbon atom within $L^1$, or a pharmaceutically acceptable salt thereof.

4. A compound or a pharmaceutically acceptable salt thereof:

Compound 3

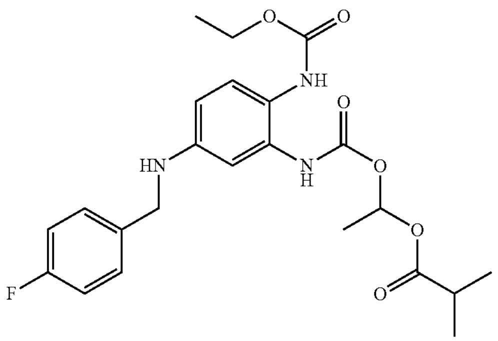

.

5. A pharmaceutical composition comprising a compound of claim 2 and one or more pharmaceutically acceptable excipient.

6. A method of eliciting one or more of an anti-epileptic, muscle relaxing, fever reducing, peripherally analgesic, or anticonvulsive effect in a patient in need thereof comprising administering an effective amount of a compound of claim 2.

7. A method of treating one or more of depression, depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, manic depressive illness with mixed episodes and manic depressive illness with depressive episodes, seasonal affective disorder, bipolar depression BP I, bipolar depression BP II, or major depression with dysthymia; dysthymia; phobias, agoraphobia, social phobia or simple phobias; eating disorders, anorexia nervosa or bulimia nervosa; chemical dependencies, addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, dementia in Parkinson's disease, neuroleptic-induced parkinsonism or tardive dyskinesias; headache, headache associated with vascular disorders; withdrawal syndrome; age-associated learning and mental disorders; apathy; bipolar disorder; chronic fatigue syndrome; chronic or acute stress; conduct disorder; cyclothymic disorder; somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; posttraumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders, Tourette's disease, comprising administering a compound of claim 2.

8. A method of treating or ameliorating the progress of a disease or a disorder selected from the group consisting of seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorders, phobias, Pick's disease, psychosis, a bipolar disorder, Schizophrenia, schizophrenia subtypes being the catatonic-subtype, the paranoid-subtype, the disorganized subtype or the residual subtype, Spinal cord damage, cardiomyopathie, cardiac arrhythmia, long QTSyndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, or meta Static tumor growth, a pneumoconiosis, aluminosis, anthracosis, asbestosis, chalicosis, ptilosis, Siderosis, Silicosis, tabacosis and by Sinosis, and a chronic obstructive pulmonary disease (COPD), and obesity and disease associated hypertension, comprising administering a compound of claim 2.

9. A method of treating one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, autism spectrum disorders, comprising administering a compound of claim 2.

10. A method of delivering a broad spectrum Kv7.2-7.5 active molecule to systemic circulation and releasing said active Kv channel opener in an effective concentration at therapeutic concentrations to treat one or more susceptible disease or disorder comprising administering a compound of claim 2.

11. The method of claim 10, where release of the active molecule is provided under one or more of:

enhanced by increased absorption;

delayed in the time to onset to improve treatment emergent adverse events; and increase the half-life or residence time through delayed circulation and release, thus negating the need for development of a modified, sustained, delayed, or extended release formulation.

12. The method of claim 10, where release of the active molecule is provided under one or more of:

enhanced by increased absorption;

delayed in the time to onset to improve treatment emergent adverse events; and increase the half-life or residence time through delayed circulation and release, thus negating the need for development of a modified, sustained, delayed, or extended release formulation.

13. A pharmaceutical composition comprising a compound of claim 4 and one or more pharmaceutically acceptable excipient.

14. A method of eliciting one or more of an anti-epileptic, muscle relaxing, fever reducing, peripherally analgesic, or anticonvulsive effect in a patient in need thereof comprising administering an effective amount of a compound of claim 4.

15. A method of treating one or more of depression, depression in cancer patients, depression in Parkinson's patients, post-myocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, manic depressive illness with mixed episodes and manic depressive illness with depressive episodes, seasonal affective disorder, bipolar depression BP I, bipolar depression BP II, or major depression with dysthymia; dysthymia; phobias, agoraphobia, social phobia or simple phobias; eating disorders, anorexia nervosa or bulimia nervosa; chemical dependencies, addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, dementia in Parkinson's disease, neuroleptic-induced parkinsonism or tardive dyskinesias; headache, headache associated with vascular disorders; withdrawal syndrome; age-associated learning and mental disorders; apathy; bipolar disorder; chronic fatigue syndrome; chronic or acute stress; conduct disorder; cyclothymic disorder; somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; posttraumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders, Tourette's disease, comprising administering a compound of claim 4.

16. A method of treating or ameliorating the progress of a disease or a disorder selected from the group consisting of seizures, pain, neuropathic pain, chronic headache, central pain, pain related to diabetic neuropathy, to postherpetic neuralgia and to peripheral nerve injury, drug addiction, affective disorders, Alzheimer's disease, anxiety, CNS damage caused by neurodegenerative illness or diseases or injury, cognitive deficits, compulsive behavior, dementia, depressions, Huntington's disease, dystonia, mania, cognitive disorders, memory impairment, memory disorders, memory dysfunction, motion disorders, motor disorders, neurodegenerative diseases, Parkinson's disease, Parkinson-like motor disorders, phobias, Pick's disease, psychosis, a bipolar disorder, Schizophrenia, schizophrenia subtypes being the catatonic-subtype, the paranoid-subtype, the disorganized subtype or the residual subtype, Spinal cord damage, cardiomyopathie, cardiac arrhythmia, long QTSyndrome, a motion disorder, or a motor disorder, myasthenia gravis, migraine, tension headache, a bowel disorder, an inflammatory disease, ulcerative colitis, Crohn's disease, Creutzfeid-Jacobs disease, an ophthalmic condition, progressive hearing loss or tinnitus, fever, Multiple Sclerosis, diabetes, or meta Static tumor growth, a pneumoconiosis, Such as aluminosis, anthracosis, asbestosis, chalicosis, ptilosis, Siderosis, Silicosis, tabacosis and by Sinosis, and a chronic obstructive pulmonary disease (COPD), and obesity and disease associated hypertension, comprising administering a compound of claim 4.

17. A method of treating one or more movement disorder selected from primary dystonia, paroxysmal dystonia, secondary dystonia, drug induced dystonia/dyskinesia, tardive dystonia, neuroleptics induced dystonia, treatment induced dystonia/dyskinesia in Parkinson's disease patients, heredodegenerative dystonia, dystonia in Huntington's disease patients, dystonia in Tourette's syndrome patients, dystonia in Restless Leg syndrome patients, dystonia like symptoms in patients with Tics, dystonia-associated dyskinesias, paroxysmal dyskinesias, paroxysmal non-kinesigenic dyskinesia, paroxysmal dystonic choreoathetosis, paroxysmal kinesigenic dyskinesia, paroxysmal kinesigenic choreoathetosis, the exertion-induced dyskinesia, hypnogenic paroxysmal dyskinesia, drug-induced dyskinesia, myokymia, neuromyotonia, autism, autism spectrum disorders, comprising administering a compound of claim 4.

18. A pharmaceutical composition comprising a compound of claim 1 and one or more pharmaceutically acceptable excipient.

19. A method of eliciting one or more of an anti-epileptic, muscle relaxing, fever reducing, peripherally analgesic, or anticonvulsive effect in a patient in need thereof comprising administering an effective amount of a compound of claim 1.

20. A method of delivering a broad spectrum Kv7.2-7.5 active molecule to systemic circulation and releasing said active Kv channel opener in an effective concentration at therapeutic concentrations to treat one or more susceptible disease or disorder comprising administering a compound of claim 1.

* * * * *